United States Patent
Blonder et al.

(10) Patent No.: US 8,790,869 B2
(45) Date of Patent: Jul. 29, 2014

(54) RENAL CELL CARCINOMA BIOMARKERS

(75) Inventors: Josip Blonder, Frederick, MD (US);
Bih-Rong Wei, Rockville, MD (US);
Donald J. Johann, Bethesda, MD (US);
Timothy D. Veenstra, Jefferson, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 107 days.

(21) Appl. No.: 13/257,580

(22) PCT Filed: Mar. 20, 2009

(86) PCT No.: PCT/US2009/037855
§ 371 (c)(1),
(2), (4) Date: Sep. 19, 2011

(87) PCT Pub. No.: WO2010/107443
PCT Pub. Date: Sep. 23, 2010

(65) Prior Publication Data
US 2012/0009201 A1   Jan. 12, 2012

(51) Int. Cl.
*G01N 33/574* (2006.01)
*G01N 33/50* (2006.01)
*G01N 33/68* (2006.01)

(52) U.S. Cl.
CPC .............. *G01N 33/574* (2013.01); *G01N 33/50* (2013.01); *G01N 33/68* (2013.01); *G01N 33/6842* (2013.01); *G01N 33/6848* (2013.01)
USPC .......................................................... 435/4

(58) Field of Classification Search
CPC ................... G01N 33/57438; G01N 30/7233; G01N 30/72; G01N 30/00; G01N 33/50; G01N 2800/56; G01N 33/574; G01N 33/68; G01N 33/6842; G01N 33/6848; C12Q 1/6886; C12Q 2600/158
See application file for complete search history.

(56) References Cited

U.S. PATENT DOCUMENTS

| | | |
|---|---|---|
| 2005/0014687 A1 | 1/2005 | Anderson et al. |
| 2006/0134708 A1 | 6/2006 | Yang |
| 2008/0008699 A1 | 1/2008 | Li et al. |

FOREIGN PATENT DOCUMENTS

| | | |
|---|---|---|
| EP | 1930426 | 6/2008 |
| WO | WO 03/080856 | 10/2003 |
| WO | WO 2006/044779 | 4/2006 |

OTHER PUBLICATIONS

Blonder et al., "Identification of membrane proteins from mammalian cell/tissue using methanol-facilitated solubilization and tryptic digestion coupled with 2D-LC-MS/MS," *Nat. Protoc.*, vol. 1, No. 6, pp. 2784-2790, 2006.

Creighton et al., "Analysis of Tumor-Host Interactions by Gene Expression Profiling of Lung Adenocarcinoma Xenografts Identifies Genes Involved in Tumor Formation," *Mol. Cancer Res.*, vol. 3, No. 3, pp. 119-129, 2005.

Dalgin et al., "Identification of Novel Epigenetic Markers for Clear Cell Renal Cell Carcinoma," *J. Urol.*, vol. 180, No. 3, pp. 1126-1130, 2008.

Dieguez-Acuna et al., "Characterization of Mouse Spleen Cells by Subtractive Proteomics," *Molecular & Cellular Proteomics*, vol. 4, pp. 1459-1470, 2005.

Johann and Blonder, "Biomarker discovery: tissues versus fluids versus both," *Expert Rev. Mol. Diagn.*, vol. 7, No. 5, pp. 473-475, 2007.

Junker et al., "Identifizierung von Biomarkern and therapeutischen Targets beim Nierenzellkarzinom mittels ProteinChip-Technologie," *Urologe*, vol. 45, No. 3, pp. 305-315, 2006.

Kolch et al., "The molecular make-up of a tumour: proteomics in cancer research," *Clinical Science*, vol. 108, pp. 369-383, 2005.

Kuick et al., "Discovery of cancer biomarkers through the use of mouse models," *Cancer Letters*, vol. 249, No. 1, pp. 40-48, 2007.

Lam et al., "Development and validation of a spectral library searching method for peptide identification from MS/MS," *Proteomics*, vol. 7, No. 5, pp. 655-667, 2007.

Oremek et al., "The Pyruvate Kinase Isoenzyme Tumor M2 (Tu M2-PK) as a Tumor Marker for Renal Carcinoma," *Anticancer Research*, vol. 19, pp. 2599-2602, 1999.

Prandini et al., "The human VE-cadherin promoter is subjected to organ-specific regulation and is activated in tumour angiogenesis," *Oncogene*, vol. 24, pp. 2992-3001, 2005.

Prieto et al., "Concurrent Proteomic Profiling of Human Tissues and Peripheral Blood Specimens for Cancer Biomarker Discovery," *J. Amer. Soc. Mass Spect.*, vol. 19, No. 5, S1, A1-A26, S13-S21, 2008.

(Continued)

*Primary Examiner* — Ruixiang Li
(74) *Attorney, Agent, or Firm* — Klarquist Sparkman, LLP

(57) ABSTRACT

Disclosed herein is a method of identifying a tumor biomarker. In one example, a tumor biomarker is identified by obtaining a peripheral biological fluid sample from a subject with a tumor as well as a tumor sample and an adjacent non-tumor sample from such subject. A protein expression profile is detected in the peripheral biological fluid sample, tumor sample and adjacent non-tumor sample. The protein expression profiles of the peripheral biological fluid sample, tumor sample and adjacent non-tumor sample are then compared, wherein an increase in expression of a specific protein in the tumor sample and peripheral biological fluid sample but not in the adjacent non-tumor sample indicates that the specific protein is a biomarker of the tumor. Also disclosed herein is a gene profiling signature that can be used to diagnosis a subject with renal cell carcinoma (RCC) or to identify agents with therapeutic potential to treat RCC. Thus, methods of diagnosing a subject with RCC are disclosed. Methods are also provided for identifying agents that alter an activity of a RCC biomarker.

11 Claims, 6 Drawing Sheets

(56) References Cited

OTHER PUBLICATIONS

Ramburan et al., "Expression of E-cadherin, cadherin-11, alpha-, beta- and gamma-catenins in nephroblastomas: relationship with clinicopathological parameters, prognostic factors and outcome," *Pathology*, vol. 38, No. 1, pp. 39-44, 2006.

Seliger et al., "Candidate biomarkers in renal cell carcinoma," *Proteomics*, vol. 7, pp. 4601-4612, 2007.

Seliger et al., "Detection of renal cell carcinoma-associated markers via proteome- and other 'ome'-based analyses," *Briefings in Functional Genomics and Proteomics*, vol. 2, No. 3, pp. 194-212, 2003.

Shioi et al., "Vascular Cell Adhesion Molecule 1 Predicts Cancer-Free Survival in Clear Cell Renal Carcinoma Patients," *Clinical Cancer Research*, vol. 12, No. 24, pp. 7339-7346, 2006.

Urakami et al., "Wnt Antagonist Family Genes as Biomarkers for Diagnosis, Staging, and Prognosis of Renal Cell Carcinoma Using Tumor and Serum DNA," *Clinical Cancer Research*, vol. 12, No. 23, pp. 6989-6997, 2006.

Wechsel et al., "Marker for renal cell carcinoma (RCC): the dimeric form of pyruvate kinase type M2 (Tu M2-PK)," *Anticancer Research*, vol. 19, No. 4A, pp. 2583-2590, 1999 (Abstract Only).

Yamanaka et al., "BIGH3 is overexpressed in clear cell renal cell carcinoma," *Oncol. Rep.*, vol. 19, No. 4, pp. 865-874, 2008 (Abstract Only).

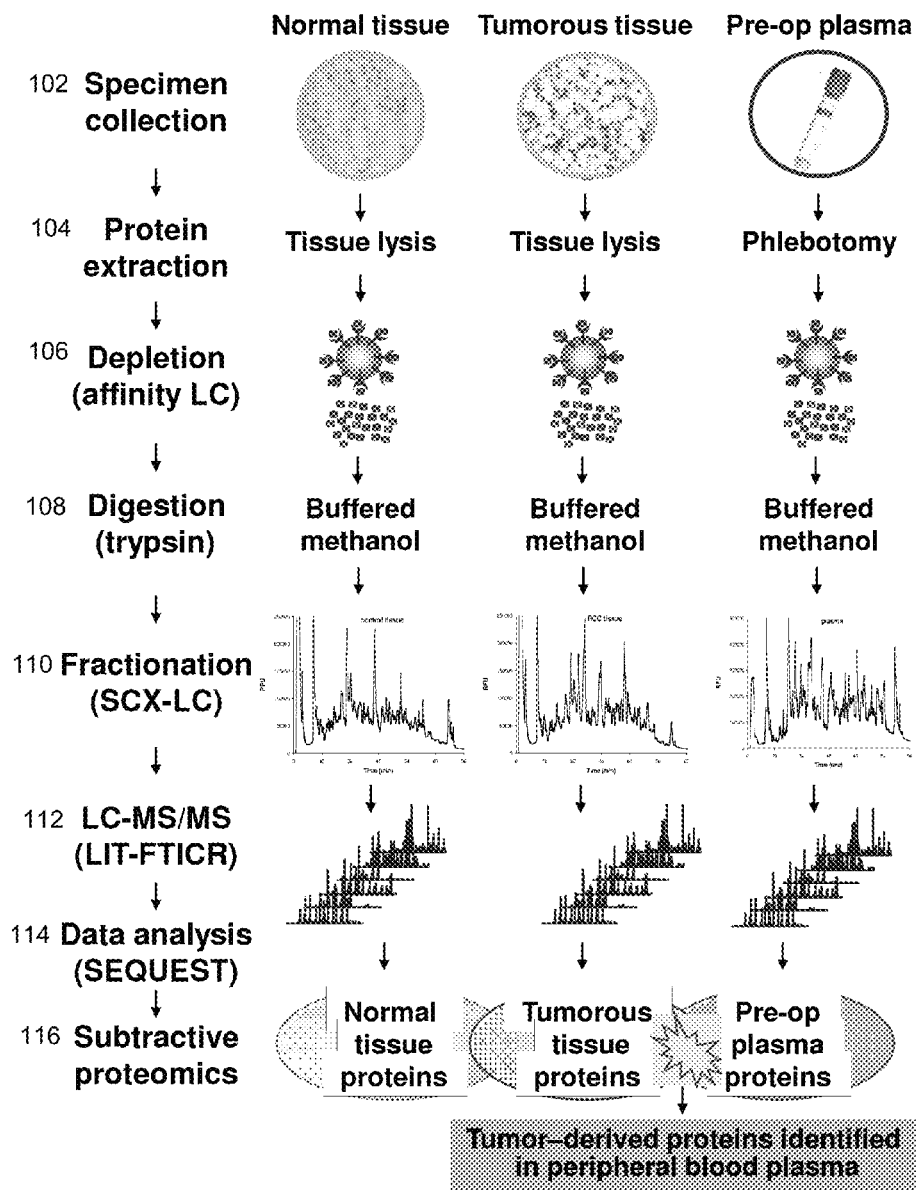

RENAL CELL CARCINOMA BIOMARKERS

CROSS REFERENCE TO RELATED APPLICATION

This is the U.S. National Stage of International Application No. PCT/US2009/037855, filed Mar. 20, 2009, which was published in English under PCT Article 21(2).

FIELD

This disclosure relates to the field of tumor biomarkers and in particular, to methods of identifying (e.g., diagnostic, prognostic, therapeutic and follow up/monitoring) tumor biomarkers for diagnosing specific tumors, such as renal cell carcinoma (RCC), identifying treatment modalities, making prognosis and follow-up for subjects with such conditions.

BACKGROUND

Cancer is the second leading cause of death in the United States. There is an acute need for cancer biomarkers that can be detected from clinically relevant samples and used for early diagnosis, therapeutic follow-up, and prognosis of malignant diseases. Proteins are principal regulators and effectors of physiologic and pathophysiologic processes. As such, proteomics is expected to play a role in clinical biomarker discovery.

Clinical proteomics is an emerging area of proteome research. For example, to identify cancer biomarkers by analyzing clinically relevant specimens routinely procured from an individual/subject. The ultimate goal of clinical oncoproteomics is to characterize proteins within a tumor environment, as well as peripheral biofluid(s) in specimens obtained from a newly diagnosed cancer subject. Individualized approaches to cancer management demand detailed and robust analyses of that subject's tumor phenotype, for necessary insights to what has been deranged (i.e., key signaling pathways, essential molecular elements). So far, the translation of proteomic assays to applicable diagnostic and/or prognostic tests in clinical oncology has been disappointing.

A number of factors currently hinder MS-based cancer biomarker research/discovery. For example, heterogeneity or variations in specific disease/cancer processes as well as the human population (in general) may introduce biases into complex proteomic datasets hindering subsequent bioinformatic and statistical analyses. Moreover, according to findings reported by the Human Proteome Organization, the dynamic range of the human plasma protein concentration is in the order of $10^{10}$ while the dynamic range of contemporary MS instrumentation is $10^4$ at best resulting in a formidable mismatch between the dynamic range of MS instrumentation and the dynamic range of human specimens. Additionally, the majority of the MS-proteomic derived "potential" cancer biomarkers are not directly germane to the tumor under study. Many of these proteins fall into the categories of acute-phase reactants and are not specific to the patho-biology under study. Moreover, some cancers may secrete a protein that is detectable within a fluid sample, while others may only manifest themselves by markers that are detectable within (or in the immediate vicinity of) the tumor. Thus, one type of sample method cannot be used to detect all types of cancer. Therefore, a need exists for oncoproteomic methodologies to rectify these issues and facilitate proteomic profiling of clinical specimens in the context of personalized medicine.

SUMMARY OF THE DISCLOSURE

There is an urgent need for methods that can facilitate cancer biomarker discovery from clinically relevant specimens. Described herein is a proteomic approach for tumor biomarker discovery, which represents a major step toward routine detection of tumor-originated proteins that can be utilized to diagnosis a subject with a particular type of cancer, such as renal cell carcinoma (RCC). For example, the disclosed method not only allows low-abundant tumor proteins to be confidentially detected in plasma, but the identification of a panel of proteins that can be specifically linked to a particular tumor type. The generated molecular protein profile identification that includes including posttranslational modifications (PTMs) and corresponding gene profile signature can then be used to diagnosis a subject with the identified tumor type or to identify agents capable of altering the biomarker expression or activity, thereby revealing possible therapeutic agents to treat the specific tumor type.

A method of identifying a tumor biomarker is disclosed herein. In one example, a tumor biomarker is identified by obtaining a peripheral biological fluid sample (such as serum or plasma) from a subject with a tumor as well as a tumor sample and an adjacent non-tumor sample from such subject. A protein expression profile is detected in the peripheral biological fluid sample, tumor sample and adjacent non-tumor sample, such as by mass spectrometry. The protein expression profiles of the peripheral biological fluid sample, tumor sample and adjacent non-tumor sample are then compared, wherein an increase in expression of a specific protein in the tumor sample and peripheral biological fluid sample but not in the adjacent non-tumor sample indicates that the specific protein is a biomarker of the tumor. In some examples, the tumor sample is renal cancer. In certain examples, the method further includes developing a consensus protein profile for diagnosing the tumor. In one example, the method also includes purifying proteins within the biological sample prior to detecting a protein expression profile. For example, purifying proteins within the biological sample can include applying samples to an affinity column, collecting flow-through, digesting flow-through, collecting digestates and fractionating resultant digestates by chromatography.

The disclosed methods revealed a molecular protein profile and corresponding gene signature that can be used to diagnose RCC. As such, a protein and corresponding gene profiling signature for RCC is disclosed herein. In one example, a molecular protein profile and corresponding gene profiling signature indicative of RCC, includes at least two of the following protein and corresponding gene RCC biomarkers: cadherin-5 precursor (CDH5); cadherin-11 precursor (CDH11); vascular cell adhesion protein 1 precursor (VCAM1); pyruvate kinase isozymes M1/M2 (PKM2); probable ATP-dependent RNA helicase (DDX23); nuclear receptor coactivator 6 (NCOA6); WW and C2 domain containing 1 (WWC1); and chromodomain-helicase-DNA-binding protein 4 (CHD4).

The disclosed protein and corresponding gene expression signature has significant implications for the diagnosis, prognosis treatment and monitoring of renal cancer, such as RCC. For example, the protein profile and corresponding gene signature can be used to diagnose a subject with renal cancer in which upregulation of one or more of the disclosed RCC biomarkers indicates that the subject has RCC. As such, methods of diagnosing a subject with renal cancer, such as RCC, are provided. In one example, the methods include detecting expression of at least two of gene products including: CDH5, CDH11, VCAM1, PKM2, DDX23, WWC1, NCOA6 and CHD4 molecules, in a biological sample obtained from a subject with renal cancer, such as RCC, or suspected of having this cancer. An increase in expression of at least two or more of these molecules indicates that the subject has renal cancer. In some examples, the methods include detecting expression of RCC biomarkers at either the nucleic acid/gene level or gene product level/protein level. In another example, the methods include determining whether a gene expression profile from the subject indicates renal cancer by using an array of molecules. In one example, the array includes oligonucleotides complementary to all of the RCC biomarkers listed in Table 1. In one example, the array includes antibodies capable of binding to one or more of the RCC biomarkers listed in Table 1.

The disclosed protein panel and corresponding gene expression signature also has significant implications for the treatment of renal cancer, such as RCC. For example, the RCC biomarkers identified by the protein molecular profile and corresponding gene profile signature can serve as targets for specific molecular therapeutic molecules that can be used to treat renal cancer, such as RCC. Thus, methods are disclosed for identifying an agent that alters the activity of a RCC biomarker, such as, CDH5, CDH11, VCAM1, PKM2, DDX23, WWC1, NCOA6 and CHD4. Such identified agents can be used in renal cancer treatments.

In an example, a method of identifying an agent that alters an activity of an RCC marker includes contacting a renal cancer cell with one or more test agents under conditions sufficient for the one or more test agents to alter the activity (such as increase or decrease the expression level) of one or more, such as at least two of the disclosed RCC biomarkers. The expression of the RCC biomarker in the presence of the one or more test agents is compared with expression in the absence of such agents. The presence of differential expression of the RCC biomarker indicates that the test agent alters the activity of the one or more RCC biomarkers and thus may have therapeutic potential and can be selected for further analysis.

The disclosed methods can further include administering to the subject a therapeutically effective treatment for RCC by administering a therapeutically effective amount of a composition, such as a specific binding agent that preferentially binds to one or more of the disclosed RCC biomarkers. For instance, the specific binding agent can be an inhibitor of one or more of the RCC biomarkers, such as a siRNA. Such inhibitors may be useful for treatment of RCC expressing disclosed biomarkers.

Also disclosed are kits, including arrays, for diagnosing RCC. For example, an array can include one or more of the disclosed RCC biomarkers, such as CDH5, CHD11, VCAM1, PKM2, DDX23, WWC1, NCOA6 and CHD4 or agents that can detect such biomarkers. Arrays can include other molecules, such as positive and negative controls.

The foregoing and other features of the disclosure will become more apparent from the following detailed description of several embodiments which proceeds with reference to the accompanying figures.

BRIEF DESCRIPTION OF THE FIGURES

FIG. 1 is a schematic diagram illustrating an exemplary proteomic workflow for cancer biomarker discovery in the context of personalized medicine. In an exemplary embodiment, a method 100 encompasses the following: 102 Specimen collection; 104 Protein extraction; 106 Depletion; 108 Digestion; 110 Fractionation; 112 LC-MS/MS analysis; 114 Data processing; and 116 Subtractive proteomics. The delineation of the tumorous tissue proteome was achieved by subtractive proteomics that relies on differences between normal and tumorous tissue proteome to depict a subset of proteins identified exclusively in tumorous-tissue. Subsequently, proteins detected exclusively in tumorous tissue were compared with proteins identified in peripheral blood plasma to elucidate tumor-derived proteins. Only overlapping protein species exhibiting higher total peptide count (abundance) in tumorous tissue were considered genuine tumor-derived proteins and potential cancer biomarkers.

FIG. 2A is a Venn diagram illustrating subtractive proteomic analysis used to reveal identities of tumorous-specific proteins from a total of 1,281 protein species identified in normal adjacent tissue (NAT) and 1,275 proteins identified in tumorous tissue (TT). A total of 202 proteins were identified by at least two protein specific peptides in any of the peptide fractions from tumorous tissue but not in any of the technical replicates from normal adjacent tissue (kidney) specimen and were considered as genuine tumor proteins. FIG. 2B is a Venn diagram illustrating subtractive proteomic analysis used to reveal identities of tumorous tissue-derived proteins in peripheral blood plasma of the patient diagnosed with RCC by subtracting proteins identified exclusively in tumorous tissue (TT, 202) and those identified in peripheral blood plasma (PL, 179). Subtractive analysis revealed a total of 8 tumor-specific proteins detected in plasma exhibiting higher total peptide count in tumorous tissue, denoting them as authentic tumor-derived proteins detectable in plasma.

SEQUENCE LISTING

Figure 2A:
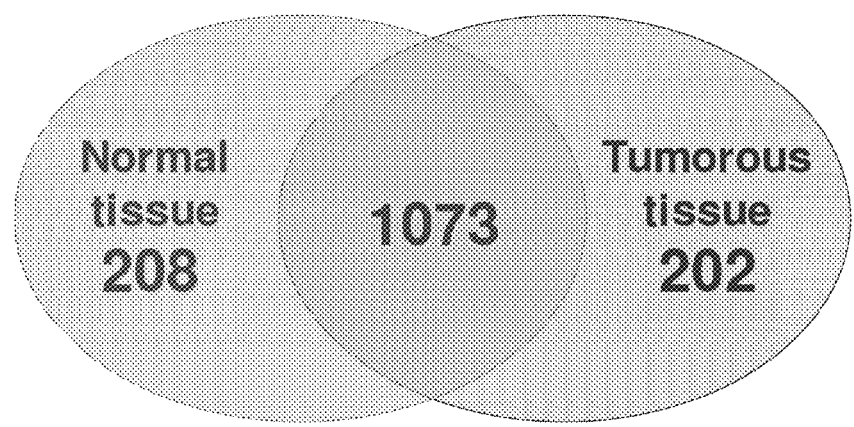
FIGS. 2A and 2B are Venn diagrams depicting subtractive proteomic analysis employed for identification of tumor-specific proteins and their detection in peripheral blood from the patient diagnosed with RCC.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NOs: 1-4 are amino acid sequences of cadherin-5 peptides detected in RCC samples as a product of CDH5 gene expression.

SEQ ID NOs: 5-9 are amino acid sequences of cadherin-11 peptides detected in RCC samples as a product of CD11 gene expression.

SEQ ID NOs: 10-12 are amino acid sequences of chromodomain-helicase-DNA-binding protein 4 peptides detected in RCC samples as a product of CHD4 gene expression.

SEQ ID NOs: 13-16 are amino acid sequences of nuclear receptor coactivator 6 peptides detected in RCC samples as a product of NCOA6 gene expression.

SEQ ID NOs: 17-19 are amino acid sequences of probable ATP-dependent RNA helicase peptides detected in RCC samples as a product of DDX23 gene expression.

SEQ ID NOs: 20-22 are amino acid sequences of pyruvate kinase isozymes M1/M2 peptides detected in RCC samples as a product of PKM2 gene expression.

SEQ ID NOs: 23-28 are amino acid sequences of vascular cell adhesion protein 1 precursor peptides detected in RCC samples as a product of VCAM1 gene expression.

SEQ ID NOs: 29-32 are amino acid sequences of WW and C2 domain containing 1 peptides detected in RCC samples as a product of WWC1 gene expression.

DETAILED DESCRIPTION OF SEVERAL EMBODIMENTS

I. Introduction

Solid tumors are heterogeneous. Essentially, they include tumor cells proper along with complex stromal elements, which form a microenvironment that nurtures the malignant process. Active interaction/signaling between different cell types constitute an integral part of tumor biology. Hence, the ability to effectively profile tumor proteomes is of interest since the proteomes of cultured cancer cells may not accurately resemble those in situ (Stein et al., *Canc. Res.*, 64: 2805-2816, 2004; Sandberg et al., *PNAS*, 102: 2052-2057, 2005).

Currently, most cancer treatments are categorically assigned based on results of population-based statistics, specifically survival functions. Therapy is not rationally assigned based on the specific molecular derangement of a subject's particular tumor. Thus, if the cancer recurs or is resistant to initial treatment, or if unacceptable toxicities occur, there is not a rational means based on the evolving molecular phenotype of the tumor to be considered for the needed therapy revision. For that reason, tendencies toward individual treatment plans, also known as personalized medicine, are increasingly contemplated in clinical oncology.

To this aim, the inventors developed a method for cancer biomarker discovery that relies on subtractive shot-gun proteomics of tumorous and non-tumorous tissues for detection of tumor-specific proteins, followed by identification of these proteins in peripheral blood plasma. The generated protein molecular profile and corresponding gene signatures can then be used for diagnosis, prognosis, therapy prediction and disease monitoring of a subject with the identified tumor type or to identify agents capable of altering the biomarker expression or activity, thereby revealing possible therapeutic agents to treat the specific tumor type. For example, the disclosed method allows detection of low-abundant tumor proteins in plasma, including a panel of proteins that can be specifically linked to RCC biology. Although specific examples are provided using RCC, one skilled in the art will appreciate that the same methods can be used to identify markers for other types of tumors, using the appropriate samples.

II. Abbreviations and Terms a. Abbreviations

CDH5: cadherin-5 precursor
CDH11: cadherin-11 precursor
CHD4: chromodomain-helicase-DNA-binding protein 4
DDX23: probable ATP-dependent RNA helicase
FRET: Förster resonance energy transfer
FTICR: fourier transform ion cyclotron resonance
HPLC: high pressure liquid chromatography
HUVEC: human umbilical vein endothelial cells
LIT: linear ion trap
MARS: multiple affinity removal system
MS: mass spectrometry
NCOA6: nuclear receptor coactivator 6
NFRPLC: nano-flow reversed phase liquid chromatography
PKM2: pyruvate kinase isozymes M1/M2
PCR: polymerase chain reaction
PTM: post-translational modification
RCC: renal cell carcinoma
VCAM1: vascular cell adhesion molecule 1
WWC1: WW and C2 domain containing 1 b. Terms

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a nucleic acid molecule" includes single or plural nucleic acid molecules and is considered equivalent to the phrase "comprising at least one nucleic acid molecule." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Unless explained otherwise, all technical and scientific terms used herein have the same meaning as commonly understood to one of ordinary skill in the art to which this disclosure belongs. All GenBank and UniProtKB Accession Nos. mentioned herein are incorporated by reference in their entirety for the sequence present on Mar. 20, 2009. Although methods and materials similar or equivalent to those described herein can be used in the practice or testing of the present disclosure, suitable methods and materials are described below. The materials, methods, and examples are illustrative only and not intended to be limiting.

Administration: To provide or give a subject an agent, such as a composition that targets/inhibits one or more of the disclosed tumor biomarkers, by any effective route. Exemplary routes of administration include, but are not limited to, injection (such as subcutaneous, intramuscular, intradermal, intraperitoneal, and intravenous), oral, sublingual, rectal, transdermal, intranasal, vaginal and inhalation routes.

Amplifying a nucleic acid molecule: To increase the number of copies of a nucleic acid molecule, such as a gene or fragment of a gene, for example a region of a gene that encodes a tumor biomarker, such as a RCC tumor biomarker. The resulting products are called amplification products.

An example of in vitro amplification is the polymerase chain reaction (PCR). Other examples of in vitro amplification techniques include quantitative real-time PCR, strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

A commonly used method for real-time quantitative polymerase chain reaction involves the use of a double stranded DNA dye (such as SYBR Green I dye). For example, as the amount of PCR product increases, more SYBR Green I dye binds to DNA, resulting in a steady increase in fluorescence. Another commonly used method is real-time quantitative TaqMan PCR (Applied Biosystems). This type of PCR has reduced the variability traditionally associated with quantitative PCR, thus allowing the routine and reliable quantification of PCR products to produce sensitive, accurate, and reproducible measurements of levels of gene expression. The 5' nuclease assay provides a real-time method for detecting only specific amplification products. During amplification, annealing of the probe to its target sequence generates a substrate that is cleaved by the 5' nuclease activity of Taq DNA polymerase when the enzyme extends from an upstream primer into the region of the probe. This dependence on polymerization ensures that cleavage of the probe occurs only if the target sequence is being amplified. The use of fluorogenic probes makes it possible to eliminate post-PCR processing for the analysis of probe degradation. The probe is an oligonucleotide with both a reporter fluorescent dye and a quencher dye attached. While the probe is intact, the proximity of the quencher greatly reduces the fluorescence emitted by the reporter dye by Förster resonance energy transfer (FRET) through space. Probe design and synthesis has been simplified by the finding that adequate quenching is observed for probes with the reporter at the 5' end and the quencher at the 3' end.

Antibody: A polypeptide ligand comprising at least a light chain or heavy chain immunoglobulin variable region which specifically recognizes and binds an epitope of an antigen, such as a tumor protein, including an RCC tumor protein, or a fragment thereof. Antibodies are composed of a heavy and a light chain, each of which has a variable region, termed the variable heavy (VH) region and the variable light (VL) region. Together, the VH region and the VL region are responsible for binding the antigen recognized by the antibody. This includes intact immunoglobulins and the variants and portions of them well known in the art, such as Fab' fragments, F(ab)'2 fragments, single chain Fv proteins ("scFv"), and disulfide stabilized Fv proteins ("dsFv"). The term also includes recombinant forms such as chimeric antibodies (for example, humanized murine antibodies), heteroconjugate antibodies (such as, bispecific antibodies). See also, Pierce Catalog and Handbook, 1994-1995 (Pierce Chemical Co., Rockford, Ill.); Kuby, Immunology, 3rd Ed., W.H. Freeman & Co., New York, 1997.

Antisense oligonucleotide: As used herein, an "antisense oligonucleotide" is a single-stranded antisense compound that is a nucleic acid-based oligomer. An antisense oligonucleotide can include one or more chemical modifications to the sugar, base, and/or internucleoside linkages. Generally, antisense oligonucleotides are "DNA-like" such that when the antisense oligonucleotide hybridizes to a target mRNA, the duplex is recognized by RNase H (an enzyme that recognizes DNA:RNA duplexes), resulting in cleavage of the mRNA.

Array: An arrangement of molecules, such as biological macromolecules (such as peptides or nucleic acid molecules) or biological samples (such as tissue sections), in addressable locations on or in a substrate. A "microarray" is an array that is miniaturized so as to require or be aided by microscopic examination for evaluation or analysis. Arrays are sometimes called DNA chips or biochips.

The array of molecules ("features") makes it possible to carry out a very large number of analyses on a sample at one time. In certain example arrays, one or more molecules (such as an antibody or peptide) will occur on the array a plurality of times (such as twice), for instance to provide internal controls. The number of addressable locations on the array can vary, for example from at least one, to at least 2, to at least 3, at least 4, at least 5, at least 6, at least 10, at least 20, at least 30, at least 50, at least 75, at least 100, at least 150, at least 200, at least 300, at least 500, least 550, at least 600, at least 800, at least 1000, at least 10,000, or more. In some examples, arrays include positive and/or negative controls, such as housekeeping markers. In particular examples, an array includes nucleic acid molecules, such as oligonucleotide sequences that are at least 15 nucleotides in length, such as about 15-40 nucleotides in length. In particular examples, an array includes oligonucleotide probes or primers which can be used to detect nucleotides that encode tumor biomarker sequences (including RCC biomarkers), such as at least two of those listed in Table 1, including 3, 4, 5, 6, 7, or all 8 of the biomarkers listed in Table 1. In an example, the array is a commercially available array such as Human Genome GeneChip® arrays from Affymetrix® (Santa Clara, Calif.).

Within an array, each arrayed sample is addressable, in that its location can be reliably and consistently determined within at least two dimensions of the array. The feature application location on an array can assume different shapes. For example, the array can be regular (such as arranged in uniform rows and columns) or irregular. Thus, in ordered arrays the location of each sample is assigned to the sample at the time when it is applied to the array, and a key may be provided in order to correlate each location with the appropriate target or feature position. Often, ordered arrays are arranged in a symmetrical grid pattern, but samples could be arranged in other patterns (such as in radially distributed lines, spiral lines, or ordered clusters). Addressable arrays usually are computer readable, in that a computer can be programmed to correlate a particular address on the array with information about the sample at that position (such as hybridization or binding data, including for instance signal intensity). In some examples of computer readable formats, the individual features in the array are arranged regularly, for instance in a Cartesian grid pattern, which can be correlated to address information by a computer.

Protein-based arrays include probe molecules that are or include proteins, or where the target molecules are or include proteins. In some examples, an array contains antibodies to tumor biomarkers, such as the disclosed RCC biomarkers, such as any combination of those listed in Table 1, such as at least 2, including 3, 4, 5, 6, 7, or all 8 of the proteins listed in Table 1.

Binding or stable binding: An association between two substances or molecules, such as the association of an antibody with a peptide, nucleic acid to another nucleic acid, or the association of a protein with another protein or nucleic acid molecule. Binding can be detected by any procedure known to one skilled in the art, such as by physical or functional properties of the target:oligonucleotide complex. For example, binding can be detected functionally by determining whether binding has an observable effect upon a biosynthetic process such as expression of a gene, DNA replication, transcription, translation, and the like.

Physical methods of detecting the binding of complementary strands of nucleic acid molecules, include but are not limited to, such methods as DNase I or chemical footprinting, gel shift and affinity cleavage assays, Northern blotting, dot blotting and light absorption detection procedures. For example, one method involves observing a change in light absorption of a solution containing an oligonucleotide (or an analog) and a target nucleic acid at 220 to 300 nm as the temperature is slowly increased. If the oligonucleotide or analog has bound to its target, there is a sudden increase in absorption at a characteristic temperature as the oligonucleotide (or analog) and target disassociate from each other, or melt. In another example, the method involves detecting a signal, such as a detectable label, present on one or both nucleic acid molecules (or antibody or protein as appropriate).

The binding between an oligomer and its target nucleic acid is frequently characterized by the temperature ($T_m$) at which 50% of the oligomer is melted from its target. A higher ($T_m$) means a stronger or more stable complex relative to a complex with a lower ($T_m$).

Biomarker: Molecular, biological or physical attributes that characterize a physiological state and can be objectively measured to detect or define disease progression or predict or quantify therapeutic responses. For instance, a substance used as an indicator of a biologic state. It is a characteristic that is objectively measured and evaluated as an indicator of normal biologic processes, pathogenic processes, or pharmacologic responses to a therapeutic intervention. In one example, a biomarker is a protein or nucleic acid sequence of a corresponding gene that is indicator of a tumor, such as RCC.

Cadherins: Genes and gene product molecules including PTMs that mediate cell adhesion and play a role in cell development. Cadherins participate in the maintenance of proper cell-cell contacts. Cadherins typically consist of five tandem repeated extracellular domains, a single membrane-spanning segment and a cytoplasmic region. Cadherins depend on calcium for their function: removal of calcium abolishes adhesive activity and renders cadherins vunerable to proteases. Cadherins are synthesized as a precursor polypeptides. The precursor polypeptide/s undergoes a series of post-translational modifications (glycosylation, phosphorylation and proteolytic cleavage) to form a protein which is typically between 723 and 748 amino acids in length. The extracelluar domain contains 3-5 internal repeats of approximately 110 amino acids. Repeats 1-3 contain a putative $Ca^{2+}$ binding site motif, such as DXD. The N-terminal 113 amino acids which contain a conserved HAV sequence have been shown to be involved in ligand binding and specificity. The extracellular domain is anchored to the cell membrane by a transmembrane domain of approximately 24 amino acids. The short cytoplasmic domain is the most highly conserved region of homology between cadherins and is involved in cadherin function.

Cadherin-5 (CDH5): CDH5 is also known as vascular endothelial (VE)-cadherin, CD144 or 7B4 antigen. Cadherin-5 protein is a calcium-dependent cell-cell adhesion glycoprotein possessing five extracellular cadherin repeats, a transmembrane region and a highly conserved cytoplasmic tail. Cadherin-5 imparts to cells the ability to adhere in a homophilic manner and may play a role in endothelial cell biology through control of the cohesion and organization of the intercellular junctions.

In particular examples, expression of CDH5 gene or its product molecules, including cadherin-5 and corresponding PTMs, is increased in RCC. The term cadherin-5 includes CDH5 genes, cDNAs, mRNAs, proteins or protein's PTMs that are expressed at elevated levels in a RCC biological sample relative to a control (such as a non-tumor sample or a standard value).

Cadherin-5 protein amino acid sequence and nucleic acid sequence for CDH5 gene are publicly available. For example, UniProtKB/Swiss-Prot Accession No. P33151 (CADH5_HUMAN) discloses cadherin-5 protein sequence, GenBank Accession Nos.: NM_001795 and NM_001795.3 disclose CDH5 nucleic acid sequences. GenPept Accession Nos.: NP_001786 and NP_001786.1 also disclose protein sequences, all of which are incorporated by reference as listed on UniProtKB/Swiss-Prot, GenBank and GenPept on Mar. 20, 2009.

In one example, CDH5 includes a full-length wild-type (or native) sequence, as well as CDH5 allelic variants that retain CDH5 activity (such as adhesive activity). In certain examples, CDH5 has at least 80% sequence identity, for example at least 85%, 90%, 95%, or 98% sequence identity to CDH5 and retains CDH5 activity.

Cadherin-11 (CDH11): A protein that mediates homophilic cell-cell adhesion. CDH11 gene has been shown to be constitutively expressed in stromal and osteoblastic cells in bone marrow and has been suggested to be involved in bone development and maintenance.

In particular examples, expression of CDH11 is increased in RCC. The term CDH11 includes CADH11 genes, cDNAs, mRNAs, proteins or protein PTMs that are expressed at elevated levels in a RCC biological sample relative to a control (such as a non-tumor sample or a standard value).

Cadherin-11 protein amino acid sequence and nucleic acid sequence for CDH11 gene are publicly available. For example, UniProtKB/Swiss-Prot Accession No. P55287 (CAD11_HUMAN) discloses cadherin-11 protein sequence, GenBank Accession Nos.: NM_001797 and NM_001797.2 disclose CDH11 nucleic acid sequences, GenPept.: NP_001788, and NP_001788.2 also disclose cadherin-11 protein sequences, all of which are incorporated by reference as listed on UniProtKB/Swiss-Prot, GenBank and GenPept on Mar. 20, 2009.

In one example, CDH11 includes a full-length wild-type (or native) sequence, as well as CDH11 allelic variants that retain CDH11 activity (such as adhesive activity). In certain examples, CDH11 has at least 80% sequence identity, for example at least 85%, 90%, 95%, or 98% sequence identity to CDH11 and retains CDH11 activity.

Cancer: A disease or condition in which abnormal cells divide without control and are able to invade other tissues. Cancer cells spread to other body parts through the blood and lymphatic systems. Cancer is a term for many diseases, there are more than 100 different types of cancer in humans. Most cancers are named after the organ in which they start, for instance, a cancer that begins in the colon is called a colon cancer. Cancer is a malignant tumor characterized by abnormal or uncontrolled cell growth. Other features often associated with cancer include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc. "Metastatic disease" refers to cancer cells that have left the original tumor site and migrate to other parts of the body for example via the bloodstream or lymph system.

The "pathology" of cancer includes all phenomena that compromise the well-being of the subject. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

cDNA (complementary DNA): A piece of DNA lacking internal, non-coding segments (introns) and regulatory sequences which determine transcription. cDNA can be synthesized by reverse transcription from messenger RNA extracted from cells.

Chemotherapeutic agent or Chemotherapy: Any chemical agent with therapeutic usefulness in the treatment of diseases characterized by abnormal cell growth. Such diseases include tumors, neoplasms, and cancer as well as diseases characterized by hyperplastic growth. In one embodiment, a chemotherapeutic agent is an agent of use in treating cancer, such as RCC. In one example, a chemotherapeutic agent is a radioactive compound. One of skill in the art can readily identify a chemotherapeutic agent of use (see for example, Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology 2nd ed., 2000 Churchill Livingstone, Inc; Baltzer and Berkery. (eds): Oncology Pocket Guide to Chemotherapy, 2nd ed. St. Louis, Mosby-Year Book, 1995; Fischer Knobf, and Durivage (eds): The Cancer Chemotherapy FDA approved regimens for treating RCC include the following:

| Regimen | Literature Reference |
|---|---|
| High-dose IL-2 | Yang J C et al., *JCO* 2003; 21: 3127-32 |
| Subcutaneous low-dose IL-2 | " |
| Interferon Alpha-2A | Negrier S et al.; *NEJM* 1998; 338: 1272-78 |
| Fluorouracil + Gemcitabine | Rini B I et al., *JCO* 2000; 18: 2419-26 |
| Sorafenib | Escudier B et al., (abstract LBA4510) *Proceedings Am Soc Clin Onc,* 2005; 23 (16S, Part I), 380S |
| Sunitinib | Motzer R J et al., (abstract 4508) *Proceedings Am Soc Clin Onc,* 2005, 23 (16S, Part I) 380S |

Combination chemotherapy is the administration of more than one agent to treat cancer.

Chromodomain-helicase-DNA-binding protein 4 (CHD4): A protein containing a central portion with 7 motifs, including a DEAD/H box, that are characteristic of helicases, a putative chromatin-binding region and multiple potential nuclear targeting signals, N-glycosylation sites, N-myristoylation sites, and phosphorylation sites. CHD4 has been previously associated with dermatomyositis.

In particular examples, expression of CHD4 is increased in RCC. The term CHD4 includes CHD4 genes, cDNAs, mRNAs, proteins or protein post-translational medication (PTMs) that are expressed at elevated levels in a RCC biological sample relative to a control (such as a non-tumor sample or a standard value).

Chromodomain-helicase-DNA-binding protein 4 amino acid sequence and nucleic acid sequences for CHD4 gene are publicly available. For example, UniProtKB/Swiss-Prot Accession No. Q14839 (CHD4_HUMAN) discloses chromodomain-helicase-DNA-binding protein 4 sequence, GenBank Accession Nos.: NM_001273 and NM_001273.2 disclose CHD4 nucleic acid sequences, GenPept.: NP_001264 and NP_001264.2 also disclose cadherin-11 protein sequences, all of which are incorporated by reference as listed on UniProtKB/Swiss-Prot, GenBank and GenPept on Mar. 20, 2009.

In one example, CHD4 includes a full-length wild-type (or native) sequence, as well as CHD4 allelic variants that retain CHD4 activity (e.g., helicase activity or elevated expression in RCC samples). In certain examples, CHD4 has at least 80% sequence identity, for example at least 85%, 90%, 95%, or 98% sequence identity to CHD4 and retains CHD4 activity.

Complementarity and percentage complementarity: Molecules with complementary nucleic acids form a stable duplex or triplex when the strands bind, (hybridize), to each other by forming Watson-Crick, Hoogsteen or reverse Hoogsteen base pairs. Stable binding occurs when an oligonucleotide molecule remains detectably bound to a target nucleic acid sequence under the required conditions.

Complementarity is the degree to which bases in one nucleic acid strand base pair with the bases in a second nucleic acid strand. Complementarity is conveniently described by percentage, that is, the proportion of nucleotides that form base pairs between two strands or within a specific region or domain of two strands. For example, if 10 nucleotides of a 15-nucleotide oligonucleotide form base pairs with a targeted region of a DNA molecule, that oligonucleotide is said to have 66.67% complementarity to the region of DNA targeted.

In the present disclosure, "sufficient complementarity" means that a sufficient number of base pairs exist between an oligonucleotide molecule and a target nucleic acid sequence (such as a nucleic acid sequence that encodes any of the RCC biomarkers listed in Table 1) to achieve detectable binding. When expressed or measured by percentage of base pairs formed, the percentage complementarity that fulfills this goal can range from as little as about 50% complementarity to full (100%) complementarity. In general, sufficient complementarity is at least about 50%, for example at least about 75% complementarity, at least about 90% complementarity, at least about 95% complementarity, at least about 98% complementarity, or even at least about 100% complementarity.

A thorough treatment of the qualitative and quantitative considerations involved in establishing binding conditions that allow one skilled in the art to design appropriate oligonucleotides for use under the desired conditions is provided by Beltz et al. *Methods Enzymol.* 100:266-285, 1983, and by Sambrook et al. (ed.), *Molecular Cloning: A Laboratory Manual,* 2nd ed., vol. 1-3, Cold Spring Harbor Laboratory Press, Cold Spring Harbor, N.Y., 1989.

Consists essentially of: In the context of the present disclosure, "consists essentially of" indicates that the expression of additional tumor marker genes can be evaluated, but not more than ten additional tumor marker genes. In some examples, "consists essentially of" indicates that no more than 5 other molecules are evaluated, such as no more than 4, 3, 2, or 1 other molecules. In some examples, fewer than the recited molecules are evaluated, but not less than 4, 3, 2 or 1 fewer molecules. In some examples, the expression of one or more controls is evaluated, such as a housekeeping protein or rRNA (such as 18S RNA, beta-microglobulin, GAPDH, and/or β-actin). In this context "consists of" indicates that only the expression of the stated molecules are evaluated; the expression of additional molecules is not evaluated.

Contacting: Placement in direct physical association, including both a solid and liquid form. Contacting can occur in vitro with isolated cells or tissue or in vivo by administering to a subject.

Decrease: To reduce the quality, amount, or strength of something. In one example, a therapy decreases a tumor (such as the size of a tumor, the number of tumors, the metastasis of a tumor, or combinations thereof), or one or more symptoms associated with a tumor, for example as compared to the response in the absence of the therapy (such as a therapy administered to affect tumor size via administration of a binding agent capable of binding to one or more of the RCC biomarkers listed in Table 1). In a particular example, a therapy decreases the size of a tumor, the number of tumors, the metastasis of a tumor, or combinations thereof, subsequent to the therapy, such as a decrease of at least 10%, at least 20%, at least 50%, or even at least 90%. Such decreases can be measured using the methods disclosed herein. In additional examples, the presence of at least one of the disclosed RCC biomarkers decreases a subject's chance of survival.

Determining expression, such as detecting expression of a gene product: Detection of a level of expression in either a qualitative or quantitative manner, for example by detecting nucleic acid or protein by routine methods known in the art. Detecting expression, such as detection of expression of a gene product: Detection of a level of expression in either a qualitative or quantitative manner, for example by detecting nucleic acid or protein by routine methods known in the art.

Diagnosis: The process of identifying a disease by its signs, symptoms and results of various tests. The conclusion reached through that process is also called "a diagnosis." Forms of testing commonly performed include blood tests, medical imaging, urinalysis, and biopsy.

Differential expression or altered expression: A difference, such as an increase or decrease, in the amount of messenger RNA, the conversion of mRNA to a protein, or both. In some examples, the difference is relative to a control or reference value, such as an amount of gene expression in tissue not affected by a disease, such as from sample isolated from a cell or tissue that is not tumorous or from a different subject who does not have a tumor, such as RCC. Detecting differential expression can include measuring a change in gene or protein expression, such as a change in expression of one or more genes or proteins, such as the proteins listed in Table 1. See also, "downregluated" and "upregulated," below.

DNA (deoxyribonucleic acid): A long chain polymer which includes the genetic material of most living organisms (some viruses have genes including ribonucleic acid, RNA). The repeating units in DNA polymers are four different nucleotides, each of which includes one of the four bases, adenine, guanine, cytosine and thymine bound to a deoxyribose sugar to which a phosphate group is attached. Triplets of nucleotides, referred to as codons, in DNA molecules code for amino acid in a polypeptide. The term codon is also used for the corresponding (and complementary) sequences of three nucleotides in the mRNA into which the DNA sequence is transcribed.

Downregulated or inactivation: When used in reference to the expression of a nucleic acid molecule, such as a gene, refers to any process which results in a decrease in production of a gene product. A gene product can be RNA (such as mRNA, rRNA, tRNA, and structural RNA) or protein. Therefore, gene downregulation or deactivation includes processes that decrease transcription of a gene or translation of mRNA.

Examples of processes that decrease transcription include those that facilitate degradation of a transcription initiation complex, those that decrease transcription initiation rate, those that decrease transcription elongation rate, those that decrease processivity of transcription and those that increase transcriptional repression. Gene downregulation can include reduction of expression above an existing level. Examples of processes that decrease translation include those that decrease translational initiation, those that decrease translational elongation and those that decrease mRNA stability.

Gene downregulation includes any detectable decrease in the production of a gene product. In certain examples, production of a gene product decreases by at least 2-fold, for example at least 3-fold or at least 4-fold, as compared to a control (such an amount of gene expression in a normal cell). In one example, a control is a relative amount of gene expression or protein expression in a biological sample taken from a subject who does not have cancer, such as RCC.

Expression: The process by which the coded information of a gene is converted into an operational, non-operational, or structural part of a cell, such as the synthesis of a protein. Gene expression can be influenced by external signals. For instance, exposure of a cell to a hormone may stimulate expression of a hormone-induced gene. Different types of cells can respond differently to an identical signal. Expression of a gene also can be regulated anywhere in the pathway from DNA to RNA to protein. Regulation can include controls on transcription, translation, RNA transport and processing, degradation of intermediary molecules such as mRNA, or through activation, inactivation, compartmentalization or degradation of specific protein molecules after they are produced.

The expression of one nucleic acid molecule can be altered relative to a nucleic acid molecule, such as a normal (wild type) nucleic acid molecule. Alterations in gene expression, such as differential expression, include but are not limited to: (1) overexpression; (2) underexpression; or (3) suppression of expression. Alternations in the expression of a nucleic acid molecule can be associated with, and in fact cause, a change in expression of the corresponding protein.

Protein expression can also be altered in some manner to be different from the expression of the protein in a normal (wild type) situation. This includes but is not necessarily limited to: (1) a mutation in the protein such that one or more of the amino acid residues is different; (2) a short deletion or addition of one or a few (such as no more than 10-20) amino acid residues to the sequence of the protein; (3) a longer deletion or addition of amino acid residues (such as at least 20 residues), such that an entire protein domain or sub-domain is removed or added; (4) expression of an increased amount of the protein compared to a control or standard amount; (5) expression of a decreased amount of the protein compared to a control or standard amount; (6) alteration of the subcellular localization or targeting of the protein; (7) alteration of the temporally regulated expression of the protein (such that the protein is expressed when it normally would not be, or alternatively is not expressed when it normally would be); (8) alteration in stability of a protein through increased longevity in the time that the protein remains localized in a cell; and (9) alteration of the localized (such as organ or tissue specific or subcellular localization) expression of the protein (such that the protein is not expressed where it would normally be expressed or is expressed where it normally would not be expressed), each compared to a control or standard. Controls or standards for comparison to a sample, for the determination of differential expression, include samples believed to be normal (in that they are not altered for the desired characteristic, for example a sample from a subject who does not have cancer, such as RCC) as well as laboratory values, even though possibly arbitrarily set, keeping in mind that such values can vary from laboratory to laboratory.

Laboratory standards and values may be set based on a known or determined population value (e.g., a value representing expression of a gene for a particular parameter, such as expression of a gene that encodes a disclosed RCC biomarker) and can be supplied in the format of a graph or table that permits comparison of measured, experimentally determined values.

Gene expression profile (or fingerprint): Differential or altered gene expression can be measured by changes in the detectable amount of gene expression (such as cDNA or mRNA) or by changes in the detectable amount of proteins expressed by those genes. A distinct or identifiable pattern of gene expression, for instance a pattern of high and low expression of a defined set of genes or gene-indicative nucleic acids such as ESTs; in some examples, as few as one or two genes provides a profile, but more genes can be used in a profile, for example at least 2, at least 3, at least 4, at least 5, at least 6, at least 7, at least 8, at least 10, at least 20, at least 25, at least 30, at least 50, at least 80, at least 120 or more. A gene expression profile (also referred to as a fingerprint) can be linked to a tissue or cell type (such as the kidney or an epithelial cell), to a particular stage of normal tissue growth or disease progression (such as advanced renal cancer), or to any other distinct or identifiable condition that influences gene expression in a predictable way. Gene expression profiles can include relative as well as absolute expression levels of specific genes, and can be viewed in the context of a test sample compared to a baseline or control sample profile (such as a sample from a subject who does not have RCC). In one example, a gene expression profile in a subject is read on an array (such as a nucleic acid or protein array). For example, a gene expression profile is performed using a commercially available array such as Human Genome GeneChip® arrays from Affymetrix® (Santa Clara, Calif.).

Hybridization: To form base pairs between complementary regions of two strands of DNA, RNA, or between DNA and RNA, thereby forming a duplex molecule. Hybridization conditions resulting in particular degrees of stringency will vary depending upon the nature of the hybridization method and the composition and length of the hybridizing nucleic acid sequences. Generally, the temperature of hybridization and the ionic strength (such as the $Na^+$ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). The following is an exemplary set of hybridization conditions and is not limiting:

Very High Stringency (Detects Sequences that Share at Least 90% Identity)
 Hybridization: 5×SSC at 65° C. for 16 hours
 Wash twice: 2×SSC at room temperature (RT) for 15 minutes each
 Wash twice: 0.5×SSC at 65° C. for 20 minutes each
High Stringency (Setects Sequences that Share at Least 80% Identity)
 Hybridization: 5×-6×SSC at 65° C.-70° C. for 16-20 hours
 Wash twice: 2×SSC at RT for 5-20 minutes each
 Wash twice: 1×SSC at 55° C.-70° C. for 30 minutes each Low Stringency (Detects Sequences that Share at Least 50% Identity)
 Hybridization: 6×SSC at RT to 55° C. for 16-20 hours
 Wash at least twice: 2×-3×SSC at RT to 55° C. for 20-30 minutes each.

Inhibitor: Any chemical compound, nucleic acid molecule, peptide such as an antibody, specific for a gene product that can reduce activity of a gene product or directly interfere with expression of a protein, such as those proteins listed in Table 1 that are upregulated in RCC. An inhibitor of the disclosure, for example, can inhibit the activity of a protein that is encoded by a gene either directly or indirectly. Direct inhibition can be accomplished, for example, by binding to a protein and thereby preventing the protein from binding an intended target, such as a receptor. Indirect inhibition can be accomplished, for example, by binding to a protein's intended target, such as a receptor or binding partner, thereby blocking or reducing activity of the protein. Furthermore, an inhibitor of the disclosure can inhibit a gene by reducing or inhibiting expression of the gene, inter alia by interfering with gene expression (transcription, processing, translation, post-translational modification), for example, by interfering with the gene's mRNA and blocking translation of the gene product or by post-translational modification of a gene product, or by causing changes in intracellular localization.

Isolated: An "isolated" biological component (such as a nucleic acid molecule, protein, or cell) has been substantially separated or purified away from other biological components in the cell of the organism, or the organism itself, in which the component naturally occurs, such as other chromosomal and extra-chromosomal DNA and RNA, proteins and cells. Nucleic acid molecules and proteins that have been "isolated" include nucleic acid molecules and proteins purified by standard purification methods. The term also embraces nucleic acid molecules and proteins prepared by recombinant expression in a host cell as well as chemically synthesized nucleic acid molecules and proteins. For example, an isolated cell is a renal epithelial cell that is substantially separated from other renal cell subtypes.

Label: An agent capable of detection, for example by ELISA, spectrophotometry, flow cytometry, or microscopy. For example, a label can be attached to a nucleic acid molecule or protein, thereby permitting detection of the nucleic acid molecule or protein. Examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (*Molecular Cloning: A Laboratory Manual*, Cold Spring Harbor, N.Y., 1989) and Ausubel et al. (In Current Protocols in Molecular Biology, John Wiley & Sons, New York, 1998).

Malignant: Cells that have the properties of anaplasia, invasion, and metastasis.

Mass spectrometry: A method wherein, a sample is analyzed by generating gas phase ions from the sample, which are then separated according to their mass-to-charge ratio (m/z) and detected. Methods of generating gas phase ions from a sample include electrospray ionization (ESI), matrix-assisted laser desorption-ionization (MALDI), surface-enhanced laser desorption-ionization (SELDI), chemical ionization, and electron-impact ionization (EI). Separation of ions according to their m/z ratio can be accomplished with any type of mass analyzer, including quadrupole mass analyzers (Q), time-of-flight (TOF) mass analyzers, magnetic sector mass analyzers, 3D and linear ion traps (IT), Fourier-transform ion cyclotron resonance (FT-ICR) analyzers, and combinations thereof (for example, a quadrupole-time-of-flight analyzer, or Q-TOF analyzer). Prior to separation, the sample may be subjected to one or more dimensions of chromatographic separation, for example, one or more dimensions of liquid or size exclusion chromatography or gel-electrophoretic separation.

MicroRNA (miRNA, miR): Single-stranded RNA molecules that regulate gene expression. MicroRNAs are generally 21-23 nucleotides in length. MicroRNAs are processed from primary transcripts known as pri-miRNA to short stem-loop structures called precursor (pre)-miRNA and finally to functional, mature microRNA. Mature microRNA molecules are partially complementary to one or more messenger RNA molecules, and their primary function is to down-regulate gene expression. MicroRNAs regulate gene expression through the RNAi pathway.

Nuclear receptor coactivator 6 (NCOA6): A transcriptional coactivator that can interact with nuclear hormone receptors to enhance their transcriptional activator functions. The encoded protein has been shown to be involved in hormone-dependent coactivation of several receptors, including prostanoid, retinoid, vitamin D3, thyroid hormone, and steroid receptors. The encoded protein may also act as a general coactivator since it has been shown to interact with some basal transcription factors, histone acetyltransferases, and methyltransferases.

In particular examples, expression of NCOA6 is increased in RCC. The term NCOA6 includes NCOA6 genes, cDNAs, mRNAs, proteins or protein PTMs that are expressed at elevated levels in a RCC biological sample relative to a control (such as a non-tumor sample or a standard value).

Nuclear receptor coactivator 6 protein and nucleic acid sequence for NCOA6 gene are publicly available. For example, UniProtKB/Swiss-Prot Accession No. Q14686 (NCOA6_HUMAN) discloses nuclear receptor coactivator 6 protein sequence, GenBank Accession Nos.: NM_014071 and NM_014071.2 disclose NCOA6 nucleic acid sequences, GenPept Accession Nos.: NP_054790 and NP_054790.2 also disclose protein sequences, all of which are incorporated by reference as listed on UniProtKB/Swiss-Prot, GenBank and GenPept on Mar. 20, 2009.

In one example, NCOA6 includes a full-length wild-type (or native) sequence, as well as NCOA6 allelic variants that retain NCOA6 activity. In certain examples, NCOA6 has at least 80% sequence identity, for example at least 85%, 90%, 95%, or 98% sequence identity to NCOA6 and retains NCOA6 activity.

Nucleic acid molecules representing genes: Any nucleic acid, for example DNA (intron or exon or both), cDNA, or RNA (such as mRNA), of any length suitable for use as a probe or other indicator molecule, and that is informative about the corresponding gene.

Nucleic acid molecules: A deoxyribonucleotide or ribonucleotide polymer including, without limitation, cDNA, mRNA, genomic DNA, and synthetic (such as chemically synthesized) DNA. The nucleic acid molecule can be double-stranded or single-stranded. Where single-stranded, the nucleic acid molecule can be the sense strand or the antisense strand. In addition, nucleic acid molecule can be circular or linear.

The disclosure includes isolated nucleic acid molecules that include specified lengths of a RCC biomarker nucleotide sequence, for genes that encode RCC biomarkers listed in Table 1. Such molecules can include at least 10, at least 15, at least 20, at least 25, at least 30, at least 35, at least 40, at least 45 or at least 50 consecutive nucleotides of these sequences or more, and can be obtained from any region of the RCC biomarker molecule.

Oligonucleotide: A plurality of joined nucleotides joined by native phosphodiester bonds, between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide.

Particular oligonucleotides and oligonucleotide analogs can include linear sequences up to about 200 nucleotides in length, for example a sequence (such as DNA or RNA) that is at least 6 nucleotides, for example at least 8, at least 10, at least 15, at least 20, at least 21, at least 25, at least 30, at least 35, at least 40, at least 45, at least 50, at least 100 or even at least 200 nucleotides long, or from about 6 to about 50 nucleotides, for example about 10-25 nucleotides, such as 12, 15 or 20 nucleotides.

An oligonucleotide probe is a short sequence of nucleotides, such as at least 8, at least 10, at least 15, at least 20, at least 21, at least 25, or at least 30 nucleotides in length, used to detect the presence of a complementary sequence by molecular hybridization. In particular examples, oligonucleotide probes include a label that permits detection of oligonucleotide probe:target sequence hybridization complexes.

Primers: Short nucleic acid molecules, for instance DNA oligonucleotides 10-100 nucleotides in length, such as about 15, 20, 25, 30 or 50 nucleotides or more in length. Primers can be annealed to a complementary target DNA strand by nucleic acid hybridization to form a hybrid between the primer and the target DNA strand. Primer pairs can be used for amplification of a nucleic acid sequence, such as by PCR or other nucleic acid amplification methods known in the art.

Methods for preparing and using nucleic acid primers are described, for example, in Sambrook et al. (In *Molecular Cloning: A Laboratory Manual*, CSHL, New York, 1989), Ausubel et al. (ed.) (In *Current Protocols in Molecular Biology*, John Wiley & Sons, New York, 1998), and Innis et al. (*PCR Protocols, A Guide to Methods and Applications*, Academic Press, Inc., San Diego, Calif., 1990). PCR primer pairs can be derived from a known sequence, for example, by using computer programs intended for that purpose such as Primer (Version 0.5, © 1991, Whitehead Institute for Biomedical Research, Cambridge, Mass.). One of ordinary skill in the art will appreciate that the specificity of a particular primer increases with its length. Thus, for example, a primer including 30 consecutive nucleotides will anneal to a target sequence, such as another homolog of the designated tumor biomarker protein, with a higher specificity than a corresponding primer of only 15 nucleotides. Thus, in order to obtain greater specificity, primers can be selected that include at least 20, at least 25, at least 30, at least 35, at least 40, at least 45, at least 50 or more consecutive nucleotides of a nucleotide sequence that encodes a disclosed RCC biomarker.

Probable ATP-dependent RNA helicase (DDX23): A member of the DEAD box protein family. DEAD box proteins are putative RNA helicases. They are implicated in a number of cellular processes involving alteration of RNA secondary structure, such as translation initiation, nuclear and mitochondrial splicing, and ribosome and spliceosome assembly. Based on their distribution patterns, some members of this family are believed to be involved in embryogenesis, spermatogenesis, and cellular growth and division. The protein encoded by the DDX23 gene is a component of the US snRNP complex; it may facilitate conformational changes in the spliceosome during nuclear pre-mRNA splicing.

In particular examples, expression of DDX23 is increased in RCC. The term DDX23 includes DDX23 genes, cDNAs, mRNAs, proteins or protein PTMs that are expressed at elevated levels in a RCC biological sample relative to a control (such as a non-tumor sample or a standard value).

Probable ATP-dependent RNA helicase protein amino acid sequence and nucleic acid sequence for DDX23 gene are publicly available. For example, UniProtKB/Swiss-Prot Accession No. Q9BUQ8 (DDX23_HUMAN) discloses probable ATP-dependent RNA helicase protein sequence, GenBank Accession Nos.: NM_004818 and NM_004818.2 disclose DDX23 nucleic acid sequences, GenPept Accession Nos.: NP_004809 and NP_004809.2 also disclose protein sequences, all of which are incorporated by reference as listed on UniProtKB/Swiss-Prot, GenBank and GenPept on Mar. 20, 2009.

In one example, DDX23 includes a full-length wild-type (or native) sequence, as well as DDX23 allelic variants that retain DDX23 activity (e.g., RNA helicase activity or elevated expression in an RCC sample). In certain examples, DDX23 has at least 80% sequence identity, for example at least 85%, 90%, 95%, or 98% sequence identity to DDX23 and retains DDX23 activity.

Prognosis: A prediction of the course of a disease, such as cancer (for example, epithelial cancer, such as RCC). The prediction can include determining the likelihood of a subject to develop aggressive, recurrent disease, to develop one or more metastasis, to survive a particular amount of time (e.g., determine the likelihood that a subject will survive 1, 2, 3 or 5 years), to respond to a particular therapy (e.g., immunotherapy), or combinations thereof.

Purified: The term "purified" does not require absolute purity; rather, it is intended as a relative term. Thus, for example, a purified protein preparation is one in which the protein referred to is more pure than the protein in its natural environment within a cell. For example, a preparation of a protein is purified such that the protein represents at least 50% of the total protein content of the preparation. Similarly, a purified oligonucleotide preparation is one in which the oligonucleotide is more pure than in an environment including a complex mixture of oligonucleotides.

Pyruvate kinase isozymes M1/M2 (PKM2): Two of the four isozymes of pyruvate kinase. These isozymes catalyze the transfer of a phosphoryl group from phosphoenolpyruvate (PEP) to ADP, generating ATP.

In particular examples, expression of PKM2 is increased in RCC. The term PKM2 includes PKM2 genes, cDNAs, mRNAs, proteins or protein PTMs that are expressed at elevated levels in a RCC biological sample relative to a control (such as a non-tumor sample or a standard value).

Pyruvate kinase isozymes M1/M2 protein amino acid sequence and nucleic acid sequence for PKM2 gene are publicly available. For example, UniProtKB/Swiss-Prot Accession No. P14618 (KPYM_HUMAN) discloses pyruvate kinase isozymes M1/M2 protein sequence, GenBank Accession Nos.: NM_002654 and NM_002654.3 disclose PKM2 nucleic acid sequences, GenPept Accession Nos.: NP_002645 and NP_002645.3 also disclose protein sequences, all of which are incorporated by reference as listed on UniProtKB/Swiss-Prot, GenBank and GenPept on Mar. 20, 2009.

In one example, PKM2 includes a full-length wild-type (or native) sequence, as well as PKM2 allelic variants that retain PKM2 activity (e.g., elevated expression in an RCC sample). In certain examples, PKM2 has at least 80% sequence identity, for example at least 85%, 90%, 95%, or 98% sequence identity to PKM2 and retains PKM2 activity.

Recombinant: A recombinant nucleic acid molecule is one that has a sequence that is not naturally occurring or has a sequence that is made by an artificial combination of two otherwise separated segments of sequence. This artificial combination can be accomplished by chemical synthesis or by the artificial manipulation of isolated segments of nucleic acid molecules, such as by genetic engineering techniques.

Renal cell carcinoma (RCC): The most common form of kidney cancer arising from the proximal renal tubule. RCC is also known as hypernephroma. Initial treatment is most commonly a radical or partial nephrectomy and remains the mainstay of curative treatment. Where the tumor is confined to the renal parenchyma, the 5-year survival rate is 60-70%, but this is lowered considerably where metastases have spread. RCC is generally resistant to radiation therapy and chemotherapy, although some cases respond to immunotherapy. Targeted cancer therapies such as sunitinib, temsirolimus, bevacizumab, interferon-alpha, and possibly sorafenib have improved the outlook for RCC (progression-free survival), although they have not yet demonstrated improved survival Sample (or biological sample): A biological specimen containing genomic DNA, RNA (including mRNA), protein, or combinations thereof, obtained from a subject. Examples include, but are not limited to, peripheral blood, urine, saliva, tissue biopsy, needle aspirates, surgical specimen, amniocentesis samples and autopsy material. In one example, a sample includes a tissue biopsy obtained from a subject with a tumor, such as RCC. In another example, a sample includes a peripheral blood sample obtained from a subject with a tumor, such as RCC.

Sensitivity: A measurement of activity, such as biological activity, of a molecule or collection of molecules in a given condition. In an example, sensitivity refers to the activity of any tumor biomarker molecule, such as the tumor biomarker proteins listed in Table 1 in the presence of therapeutic agent, such as an agent that targets one or more tumor biomarker proteins. In other examples, sensitivity refers to the activity of an agent (such as a therapeutic agent) on the growth, development or progression of a disease, such as RCC. For example, a decreased sensitivity refers to a state in which a tumor is less responsive to a given therapeutic agent as compared to a tumor that is responsive to the treatment.

In certain examples, sensitivity or responsiveness can be assessed using any endpoint indicating a benefit to the subject, including, without limitation, (1) inhibition, to some extent, of tumor growth, including slowing down and complete growth arrest; (2) reduction in the number of tumor cells; (3) reduction in tumor size; (4) inhibition (such as reduction, slowing down or complete stopping) of tumor cell infiltration into adjacent peripheral organs and/or tissues; (5) inhibition (such as reduction, slowing down or complete stopping) of metastasis; (6) enhancement of anti-tumor immune response, which may, but does not have to, result in the regression or rejection of the tumor; (7) relief, to some extent, of one or more symptoms associated with the tumor; (8) increase in the length of survival following treatment; and/or (9) decreased mortality at a given point of time following treatment.

In some examples, sensitivity of an assay describes the ability of the assay to accurately predict whether one has RCC using the disclosed biomarkers as compared to another assay method. For example, a marker with a sensitivity of at least 70%, including 75%, 80%, 90%, 95% or greater sensitivity is one that is capable of accurately predicting RCC.

In contrast, "specificity" refers to the ability of a marker to detect RCC as compared to other types of cancers.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215: 403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1154 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (that is, 15÷20*100=75).

For comparisons of amino acid sequences of greater than about 30 amino acids, the Blast 2 sequences function is employed using the default BLOSUM62 matrix set to default parameters, (gap existence cost of 11, and a per residue gap cost of 1). Homologs are typically characterized by possession of at least 70% sequence identity counted over the full-length alignment with an amino acid sequence using the NCBI Basic Blast 2.0, gapped blastp with databases such as the nr or swissprot database. Queries searched with the blastn program are filtered with DUST (Hancock and Armstrong, 1994, *Comput. Appl. Biosci.* 10:67-70). Other programs use SEG. In addition, a manual alignment can be performed. Proteins with even greater similarity will show increasing percentage identities when assessed by this method, such as at least about 75%, 80%, 85%, 90%, 95%, 98%, or 99% sequence identity to a protein listed in Table 1.

When aligning short peptides (fewer than around 30 amino acids), the alignment is be performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least about 60%, 70%, 75%, 80%, 85%, 90%, 95%, 98%, or 99% sequence identity to a protein listed in Table 1. When less than the entire sequence is being compared for sequence identity, homologs will typically possess at least 75% sequence identity over short windows of 10-20 amino acids, and can possess sequence identities of at least 85%, 90%, 95% or 98% depending on their identity to the reference sequence. Methods for determining sequence identity over such short windows are described at the NCBI web site.

One indication that two nucleic acid molecules are closely related is that the two molecules hybridize to each other under stringent conditions, as described above. Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. Such homologous nucleic acid sequences can, for example, possess at least about 60%, 70%, 80%, 90%, 95%, 98%, or 99% sequence identity to a nucleic acid that encodes a protein listed in Table 1 determined by this method. An alternative (and not necessarily cumulative) indication that two nucleic acid sequences are substantially identical is that the polypeptide which the first nucleic acid encodes is immunologically cross reactive with the polypeptide encoded by the second nucleic acid.

One of skill in the art will appreciate that the particular sequence identity ranges are provided for guidance only; it is possible that strongly significant homologs could be obtained that fall outside the ranges provided.

Short hairpin RNA (shRNA): A sequence of RNA that makes a tight hairpin turn and can be used to silence gene expression via the RNAi pathway. The shRNA hairpin structure is cleaved by the cellular machinery into siRNA.

Short interfering RNA (siRNA): A double stranded nucleic acid molecule capable of RNA interference or "RNAi." (See, for example, *Bass Nature* 411: 428-429, 2001; Elbashir et al., *Nature* 411: 494-498, 2001; and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914.) As used herein, siRNA molecules need not be limited to those molecules containing only RNA, but further encompasses chemically modified nucleotides and non-nucleotides having RNAi capacity or activity. In an example, a siRNA molecule is one that reduces or interferes with the biological activity of one or more molecules that is altered with cancer, such as one or more of the disclosed RCC biomarkers including CDH5, CDH11, DDX23, WWC1, CHD4, NCOA6, PKM2, and/or VCAM1.

Specific Binding Agent: An agent that binds substantially or preferentially only to a defined target such as a protein, enzyme, polysaccharide, oligonucleotide, DNA, RNA, recombinant vector or a small molecule. In an example, a "specific binding agent" is capable of binding to at least one of the disclosed RCC biomarkers (such as those listed in Table 1). In other examples, the specific binding agent is capable of binding to a downstream factor regulated by at least one of the disclosed RCC biomarkers (such as those listed in Table 1). Thus, a nucleic acid-specific binding agent binds substantially only to the defined nucleic acid, such as RNA, or to a specific region within the nucleic acid. For example, a "specific binding agent" includes an antisense compound (such as an antisense oligonucleotide, siRNA, miRNA, shRNA or ribozyme) that binds substantially to a specified RNA.

A protein-specific binding agent binds substantially only the defined protein, or to a specific region within the protein. For example, a "specific binding agent" includes antibodies and other agents that bind substantially to a specified polypeptide. Antibodies can be monoclonal or polyclonal antibodies that are specific for the polypeptide, as well as immunologically effective portions ("fragments") thereof. The determination that a particular agent binds substantially only to a specific polypeptide may readily be made by using or adapting routine procedures. One suitable in vitro assay makes use of the Western blotting procedure (described in many standard texts, including Harlow and Lane, *Using Antibodies: A Laboratory Manual*, CSHL, New York, 1999).

Standard: A substance or solution of a substance of known amount, purity or concentration. A standard can be compared (such as by spectrometric, chromatographic, or spectrophotometric analysis) to an unknown sample (of the same or similar substance) to determine the presence of the substance in the sample and/or determine the amount, purity or concentration of the unknown sample. In one embodiment, a standard is a peptide standard. An internal standard is a compound that is added in a known amount to a sample prior to sample preparation and/or analysis and serves as a reference for calculating the concentrations of the components of the sample. In one example, nucleic acid standards serve as reference values for tumor or non-tumor expression levels of specific nucleic acids. In some examples, peptide standards serve as reference values for tumor or non-tumor expression levels of specific peptides. Isotopically-labeled peptides are particularly useful as internal standards for peptide analysis since the chemical properties of the labeled peptide standards are almost identical to their non-labeled counterparts. Thus, during chemical sample preparation steps (such as chromatography, for example, HPLC) any loss of the non-labeled peptides is reflected in a similar loss of the labeled peptides.

Subject: Living multi-cellular vertebrate organisms, a category that includes human and non-human mammals, such as veterinary subjects.

Subtractive proteomics: A method of identifying proteins of interest, such as tumor proteins from proteomics datasets. As used herein, subtractive proteomics is a method used to identify a tumorous tissue proteome that relies on differences between normal and tumorous tissue proteome to depict a subset of proteins identified exclusively in tumorous-tissue. Proteomic analysis is used herein to reveal identities of tumorous tissue-derived proteins in peripheral blood plasma of a subject diagnosed with a tumor by overlapping tumorous tissue proteome and plasma proteome followed by subtracting proteins identified in parallel exclusively in tumorous tissue and those identified in peripheral blood plasma. In one example, proteins exhibiting higher peptide count in tumorous tissue versus plasma were considered genuine tumor marker proteins.

Target sequence: A sequence of nucleotides located in a particular region in the human genome that corresponds to a desired sequence, such as a tumor biomarker sequence, including a RCC biomarker sequence. The target can be for instance a coding sequence; it can also be the non-coding strand that corresponds to a coding sequence. Examples of target sequences include those sequences associated with RCC, such as any of those listed in Table 1.

Test agent: Any substance, including, but not limited to, a protein (such as an antibody or peptide), nucleic acid molecule (such as a siRNA), organic compound, inorganic compound, or other molecule of interest. In particular examples, a test agent can permeate a cell membrane (alone or in the presence of a carrier).

Therapeutically effective amount: An amount of a pharmaceutical preparation that alone, or together with a pharmaceutically acceptable carrier or one or more additional therapeutic agents, induces the desired response. A therapeutic agent, such as an agent including one or more inhibitors of the disclosed RCC biomarkers, is administered in therapeutically effective amounts.

Effective amounts a therapeutic agent can be determined in many different ways, such as assaying for a reduction in tumor size or improvement of physiological condition of a subject having cancer, such as RCC. Effective amounts also can be determined through various in vitro, in vivo or in situ assays.

Therapeutic agents can be administered in a single dose, or in several doses, for example daily, during a course of treatment. However, the effective amount can be dependent on the source applied, the subject being treated, the severity and type of the condition being treated, and the manner of administration.

In one example, it is an amount sufficient to partially or completely alleviate one or more symptoms associated with the cancer, such as one or more symptoms associated with RCC. Treatment can involve only slowing the progression of the cancer, but can also include halting or reversing the cancer progression permanently. For example, a pharmaceutical preparation can decrease one or more symptoms associated with cancer, such as RCC, by at least 20%, at least 50%, at least 70%, at least 90%, at least 98%, or even at least 100%, as compared to RCC observed in the absence of the pharmaceutical preparation. In other examples, a pharmaceutical preparation can increase the sensitivity of the cancer, such as RCC, to a primary mode of treatment, such as immunotherapy.

Tissue: A plurality of functionally related cells. A tissue can be a suspension, a semi-solid, or solid. Tissue includes cells collected from a subject such as the kidneys or a portion thereof.

Treating a disease: "Treatment" refers to a therapeutic intervention that ameliorates a sign or symptom of a disease or pathological condition, such as a sign or symptom of a particular type of cancer, including RCC. Treatment can also induce remission or cure of a condition, such as cancer, including RCC. In particular examples, treatment includes preventing a disease, for example by inhibiting the full development of a disease. Prevention of a disease does not require a total absence of disease. For example, a decrease of at least 50% can be sufficient.

Tumor: All neoplastic cell growth and proliferation, whether malignant or benign, and all pre-cancerous and cancerous cells and tissues.

Under conditions sufficient for: A phrase that is used to describe any environment that permits the desired activity. In one example, includes administering a test agent to an RCC or a subject having RCC sufficient to allow the desired activity. In particular examples, the desired activity is altering the activity (such as increasing or decreasing the expression or biological activity) of a RCC tumor biomarker molecule.

Upregulated or activation: When used in reference to the expression of a nucleic acid molecule, such as a gene, refers to any process which results in an increase in production of a gene product. A gene product can be RNA (such as mRNA, rRNA, tRNA, and structural RNA) or protein. Therefore, gene upregulation or activation includes processes that increase transcription of a gene or translation of mRNA.

Examples of processes that increase transcription include those that facilitate formation of a transcription initiation complex, those that increase transcription initiation rate, those that increase transcription elongation rate, those that increase processivity of transcription and those that relieve transcriptional repression (for example by blocking the binding of a transcriptional repressor). Gene upregulation can include inhibition of repression as well as stimulation of expression above an existing level. Examples of processes that increase translation include those that increase translational initiation, those that increase translational elongation and those that increase mRNA stability.

Gene upregulation includes any detectable increase in the production of a gene product. In certain examples, production of a gene product increases by at least 2-fold, for example at least 3-fold or at least 4-fold, as compared to a control (such an amount of gene expression in a normal cell or a reference value). In one example, a control is a relative amount of gene expression in a biological sample, such as a tissue biopsy obtained from a subject that does not have RCC or a reference value.

Vascular cell adhesion protein 1 (VCAM1): A member of the Ig superfamily and encodes a cell surface sialoglycoprotein expressed by cytokine-activated endothelium. This type I membrane protein mediates leukocyte-endothelial cell adhesion and signal transduction, and may play a role in the development of atherosclerosis and rheumatoid arthritis. Two alternatively spliced transcripts encoding different isoforms have been described for this gene.

In particular examples, expression of VCAM1 is increased in RCC. The term VCAM1 includes VCAM1 genes, cDNAs, mRNAs, proteins or protein PTMs that are expressed at elevated levels in a RCC biological sample relative to a control (such as a non-tumor sample or a standard value).

Vascular cell adhesion protein 1 amino acid sequence and nucleic acid sequence for VCAM1 gene are publicly available. For example, UniProtKB/Swiss-Prot Accession No. P19320 (VCAM1_HUMAN) discloses vascular cell adhesion protein 1 sequence, GenBank Accession Nos.: NM_001078 and NM_001078.2 disclose VCAM1 nucleic acid sequences. GenPept Accession Nos.: NP_001069 and NP_001069.1 also disclose protein sequence, all of which are incorporated by reference as listed on UniProtKB/Swiss-Prot, GenBank and GenPept on Mar. 20, 2009.

In one example, VCAM1 includes a full-length wild-type (or native) sequence, as well as VCAM1 allelic variants that retain VCAM1 activity (e.g., cell adhesive activity or elevated expression in an RCC sample). In certain examples, VCAM1 has at least 80% sequence identity, for example at least 85%, 90%, 95%, or 98% sequence identity to VCAM1 and retains VCAM1 activity.

WW and C2 domain containing 1 (WWC1): A member of the WWC family. Protein WWC1 contains 1 C2 domain and 2 WW domains. It is approximately 1113 amino acids and 125.3 kDa. This protein may interact with DDN and is located in the cytoplasm. WWC1 is also known as kidney and brain protein.

In particular examples, expression of WWC1 is increased in RCC. The term WWC1 includes WWC1 genes, cDNAs, mRNAs, proteins or protein PTMs that are expressed at elevated levels in a RCC biological sample relative to a control (such as a non-tumor sample or a standard value).

WW domain-containing protein 1 amino acid sequence and nucleic acid sequence for WWC1 gene are publicly available. For example, UniProtKB/Swiss-Prot Accession No. P19320 (VCAM1_HUMAN) discloses WW domain-containing protein 1 sequence, GenBank Accession Nos.: NM_015238 and NM_015238.1 disclose WWC1 nucleic acid sequences, GenPept Accession Nos.: NP_056053 and NP_056053.1 also disclose protein sequences, all of which are incorporated by reference as listed on UniProtKB/Swiss-Prot, GenBank and GenPept on Mar. 20, 2009.

In one example, WWC1 includes a full-length wild-type (or native) sequence, as well as WWC1 allelic variants that retain WWC1 activity. In certain examples, WWC1 has at least 80% sequence identity, for example at least 85%, 90%, 95%, or 98% sequence identity to WWC1 and retains WWC1 activity (e.g., elevated expression in RCC).

Additional terms commonly used in molecular genetics can be found in Benjamin Lewin, Genes V published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

II. Methods of Identifying Tumor Biomarkers

Disclosed herein are methods of identifying one or more tumor biomarkers. In one example, a tumor biomarker is identified by obtaining a peripheral biological fluid sample (such as serum or plasma) from a subject with a tumor as well as a tumor sample and an adjacent non-tumor sample from such subject. In some examples, the subject is pre-screened to determine if they have the tumor of interest. A protein expression profile is detected in the peripheral biological fluid sample, tumor sample and adjacent non-tumor sample, such as by mass spectrometry. The protein expression profiles of the peripheral biological fluid sample, tumor sample and adjacent non-tumor sample are then compared, wherein an alteration (such as increase or decrease) in expression of a specific protein in the tumor sample and peripheral biological fluid sample, but not in the adjacent non-tumor sample, indicates that the specific protein is a biomarker of the tumor.

Exemplary Tumors

The disclosed methods can be used to detect tumor biomarkers from various types of cancers. Examples of hematological cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, and myelodysplasia.

Examples of solid cancers, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, RCC, hepatoma, bile duct carcinoma, choriocarcinoma, Wilms' tumor, cervical cancer, testicular tumor, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

In a particular example, cancer includes renal cancer, such as RCC, for example, clear cell carcinoma, papillary carcinoma, chromophobe renal carcinoma and collecting duct carcinoma.

Biological Samples

Tumor biomarkers can be identified in different types of biological samples. For example, biological samples include a solid biological sample obtained from a subject, such as a tissue sample, or a fluid sample obtained from a subject. In particular examples, a biological sample is a peripheral biological fluid sample, a tumor sample or a non-tumor sample, such as an adjacent non-tumor sample. Peripheral biological fluid samples include those which are obtained by a non-invasive technique, such as salvia, urine, or blood. Examples of such samples include blood or fractions thereof, for example serum or plasma. In one example, a peripheral biological fluid sample is obtained prior to surgery. In other examples, it is obtained during the surgical procedure. In other examples, it is obtained after the surgical procedure.

Tumor samples include those samples obtained from the tumor, such as cancer. In one example, a tumor sample is a RCC sample. Adjacent non-tumor samples include those obtained from a region of the same tissue that the tumor is located in, but is free of tumor cells. For example, if the tumor of interest is an epithelial cancer, such as RCC, the tumor samples will include epithelial cancer tissue, while the normal adjacent tissue will include normal epithelial tissue (but not cancerous tissue) from the same subject. In some examples, the tumor sample is a RCC sample and the adjacent non-tumor sample is a sample of the kidney that does not have renal carcinoma cells. It will appreciated that any method of obtaining tissue from a subject can be utilized, and that the selection of the method used will depend upon various factors such as the type of tissue, age of the subject, or procedures available to the practitioner. For example, the tissue sample can be obtained by a variety of procedures including, but not limited to, surgical excision, aspiration, or biopsy.

Protein Expression Profiling

The disclosed methods of identifying tumor biomarkers also include purifying proteins within the biological sample and digesting them prior to detecting a protein expression profile. In some examples, proteins from the biological samples obtained from the subject are isolated or purified prior to detecting a protein expression profile. In a certain example, tumor biomarkers are identified by mass spectrometry. For example, proteins within the biological sample(s) can be obtained or purified and exposed to proteolytic cleavage in the biological sample with a protein cleavage agent, resulting in a protein digest. The intact protein and its post-translationally modified form can be in some instances also used. The fragment peptides are excised from the full length protein. Fragment peptides include peptides produced by treatment of a protein with one or more endoproteases such as trypsin, chymotrypsin, endoprotease argC, endoprotease aspN, endoprotease gluC, and endoprotease lysC, as well as peptides produced by chemical cleavage reactions, such as those that employ cyanogen bromide, formic acid, and thiotrifluoroacetic acid as is well known to those of ordinary skill in the art. In some embodiments, the proteolytic cleavage agent is serine protease. In one embodiment, the proteolytic cleavage agent is trypsin, and the resulting digest is a trypsin digest. Endogenous proteases can cleavage peptides in vivo, these peptides can also be used in the assay.

Fragment peptides of the protein products can be uniquely associated with the full length protein sequence from which they are excised. Thus, these peptides can be used to determine the presence of the full length protein in a biological sample, such as a biological sample obtained from a subject. Identification of the peptide sequence that is uniquely associated with the larger peptide sequence in a sample identifies the larger peptide sequence in the sample. In other words, a fragment peptide that is uniquely associated with a full length protein is a mass identifier that contains enough sequence information to discriminate between the protein and other proteins in the sample.

Mass identifiers are peptides (or a set of peptides) having a particular sequence(s) that is (are) uniquely generated from a protein of interest by treatment with a particular protein cleavage agent. Detection of a mass identifier for a protein of interest in a sample unambiguously identifies the presence of the protein of interest in a sample treated with the protein cleavage agent, and determination of the concentration or amount of the mass identifier in a sample also determines the concentration or amount of the protein of interest in the sample either directly or after multiplying the concentration of the mass identifier by the number of such mass identifier generated per protein of interest. Mass identifiers can be identified by treating proteins with a protein cleavage agent in vivo, in vitro or in silico. Various methods and algorithms for determining a mass identifier for a protein of interest are known, but all have in common that peptide sequences obtained by digestion (actual or theoretical) of a protein of interest with a protein cleavage agent (such as an endoprotease or a model of an endoprotease's cleavage specificity) are compared to peptide sequences obtained by digestion of other known proteins with the same cleavage agent to determine one or more peptide sequences that are uniquely produced from the protein of interest.

The fragment peptides useful in the disclosed examples are from about 6 to about 45 amino acid residues in length, such as about 6 amino acids, about 7 amino acids, about 8 amino acids, about 9 amino acids, about 10 amino acids, about 11 amino acids, about 12 amino acids, about 13 amino acids, about 14 amino acids, about 15 amino acids, about 16 amino acids, about 17 amino acids, about 18 amino acids, about 19 amino acids, about 20 amino acids, about 21 amino acids, about 22 amino acids, about 25 amino acids, about 30 amino acids, about 35 amino acids, about 40 amino acids, or about 45 amino acids in length. In some embodiments, the fragment peptide is a RCC fragment peptide (for example, cadherin-5, cadherin-11, chromodomain-helicase-DNA-binding protein 4, nuclear receptor coactivator 6, probable ATP-dependent RNA helicase, pyruvate kinase isozymes M1/M2, vascular cell adhesion protein 1 precursor and WW and C2 domain containing 1) fragment peptides as provided in Table 2.

Fragment peptides can be detected by any method that allows for the detection and identification of peptides. Methods particularly suited for the detection and identification of peptides, are mass spectrometric methods. In certain embodiments, fragment peptides are detected with mass spectrometry. In certain embodiments, the fragment peptides are detected with tandem mass spectrometry. In some embodiments, the fragment peptides are detected by detection of ion fragments generated from fragment peptides (for example, by collision using tandem mass spectrometry). Exemplary mass spectrometric methods that can be used in the disclosed methods are found below, although it is contemplated that any mass spectrometric technique that identifies peptides could be used.

Enzymatic digestion of complex mixtures of proteins followed by mass spectrometric based analysis of the digest is well known in the art (see for example, U.S. Pat. No. 6,940, 065 and Yates et al., *J. Protein Chem.*, 16: 495-497, 1997). Prior to mass spectrometric analysis, it can be advantageous to fractionate the protein digest, for example by chromatographing the protein digest. Methods of fractionation of a protein sample are well known in the art, and include without limitation chromatographic methods, such as gas chromatography, paper chromatography, thin layer chromatography (TLC), liquid chromatography, column chromatography, fast protein liquid chromatography (FPLC), ion exchange chromatography, size exclusion chromatography, affinity chromatography, high performance liquid chromatography (HPLC), poly acrylamide gel electrophoresis (PAGE), capillary electrophoresis (CE) and reverse phase high performance liquid chromatography (RP-HPLC) amongst others. In some examples of the disclosed methods, the fragment peptides generated from a protein digest are labeled with a mass identifier, for example using iTRAQ® regents (Applied Biosystems). Using iTRAQ® regents multiple samples can be run simultaneously using different iTRAQ® reagents that label the individual samples with different mass identifiers. By way of example, sample one can be labeled with a mass identifier or mass tag that has a molecular weight of 114 amu, while sample two mass identifier or mass tag with a molecular weight of 117. The sample can be combined and subjected to mass spectrometric analysis the fragment peptides from sample two will have a predictable mass difference of three amu for the same peptide. In other words, a peptide of identical sequence in sample one and sample two will be three amu heavier. This predictable mass difference can be used both to identify the peptide fragments (and hence the protein from which they were excised) and the relative quantities of each peptide in the samples.

Aspects of the disclosed methods relate to quantitating the amount of the fragment peptides present in the biological sample. The quantity of a fragment peptide present in the biological sample is proportional to the amount of the full length protein that the fragment peptide is excised from present in the sample prior to digestion, thus the disclosed method allows for the quantification the full length protein in the biological sample.

Protein expression levels can be quantified by mass spectrometry if peptide standards of known concentration are available. Methods for quantifying a fragment peptide include comparing an amount of the fragment peptide to a peptide standard of known amount. Typically, the peptide standards are isotopically labeled peptides, and these are added in known amounts to a non-labeled protein digest. However, non-isotopically labeled peptide standards also can be used. By way of example, the change in relative peak intensity before and after the addition of a peptide standard can be used to calculate the amount of a fragment peptide present in a biological sample, thus providing quantification of the full length protein in the sample. When a non-isotopically labeled peptide standard is used, a mass spectrum of the protein digest is obtained without addition of the non-isotopically labeled peptide standard and mass spectrum of the protein digest is obtained with the addition of the non-isotopically labeled peptide standard. The ratio of the intensity of the signals with and without the addition of the non-isotopically labeled peptide standard reflects the relative amounts (or concentrations) of the fragment peptide present in a biological sample, and thus the amount of the full length protein present in the sample. It is understood that the spectra with and without the peptide standard can be obtained in any order.

When isotopically-labeled peptides are used, typically the combined sample (peptide standard plus protein digest) is analyzed by mass spectrometry, and the ratios of the mass spectral signal intensities for the peptide standard and the sample peptides are measured. In some examples, the peptide standard is isotopically-labeled and the peptides in the digest are not labeled. In some examples, the peptides in the digest reaction are isotopically-labeled and the peptide standard is not labeled. In other examples, the peptide standard is labeled with a different mass identifier or mass tag than the mass identifier or mass tag that labels the peptides in the digest, such that both the peptide standard and the peptides in the digest are labeled.

Typically, the peptide standard is added to the biological sample prior to the protein digest, however in some circumstances it may be advantageous to add the peptide standard after proteolytic digest. A mass spectrum of a sample containing both sample peptides and the added peptide standard typically includes one or more pairs of separated signals that are due to a sample peptide and its corresponding peptide standard. The ratio of the intensity of the signals in each pair reflects the relative amounts (or concentrations) of each peptide present in the sample. Since the amount (or concentration) of the peptide standard is known, the amount (or concentration) of the sample peptide can be calculated by multiplying the ratio of the intensity of the signal for the sample peptide to the intensity of the signal for the peptide standard by the known amount (or concentration) of the peptide standard. Furthermore, since the sample peptides are present in amounts (or concentrations) that are the same as (or related by a known ratio to) the amounts (or concentrations) of the proteins originally in the sample, a determination of the amounts (or concentrations) of the sample peptides also permits a determination of the amounts (or concentrations) of the proteins in the sample. Since the concentrations of the peptide standards are known, the concentration of the sample peptides (and the proteins they are derived from) can be calculated using the ratios. However, external calibrants and standards can be used instead to the internal standard. External standards are run in between samples that are being quantified. The number of standards and their frequency depends on the reproducibility of the MS platform.

Peptide standards useful in the disclosed method correspond to an amino acid sequence of about 6 to about 45 amino acid residues of the specified protein, such as about 6 amino acids, about 7 amino acids, about 8 amino acids, about 9 amino acids, about 10 amino acids, about 11 amino acids, about 12 amino acids, about 13 amino acids, about 14 amino acids, about 15 amino acids, about 16 amino acids, about 17 amino acids, about 18 amino acids, about 19 amino acids, about 20 amino acids, about 21 amino acids, about 22 amino acids, about 25 amino acids, about 30 amino acids, about 35 amino acids, about 40 amino acids, or about 45 amino acids in length. In some embodiments, the peptide standard is labeled with an isotope, such as a heavy stable isotope. Exemplary heavy stable isotopes include but are not limited to $^{18}O$, $^{17}O$, $^{34}S$, $^{15}N$, $^{13}C$, and $^2H$. Peptide standards can be labeled with one or more isotopes, for example a labeled peptide can contain $^{18}O$, $^{17}O$, $^{15}N$, $^{34}S$, $^{13}C$, and $^2H$ or any combination thereof. Methods of labeling peptides with heavy isotopes are well known in the art.

Once the proteins have been identified within each of the samples, those which are relevant to diagnosis can be determine by any methods known to those of skill in the art to be useful to identifying proteins specific for various conditions or diseases, such as RCC, including subtractive proteomics. For example, proteins relevant for diagnosis can be identified by comparing the protein expression profiles of the peripheral biological fluid sample, tumor sample and adjacent non-tumor sample, wherein an increase in expression of a specific protein in the tumor sample and peripheral biological fluid sample but not in the adjacent non-tumor sample indicates that the specific protein is a biomarker of the tumor.

Exemplary Embodiment

FIG. 1 provides an exemplary embodiment of the disclosed method of identifying a tumor marker. The method includes specimen collection 102 in which tumor, normal adjacent tissue (e.g., tissue of the same type as where the tumor occurs, but does not have tumor cells) and peripheral blood plasma are collected prospectively from a subject diagnosed with a particular type of tumor, such as a cancer of interest. A peripheral blood plasma sample can be collected either prior to, concurrent with or following surgery. In one example, the sample is collected prior to surgery to eliminate potential biases caused by leaking of tissue proteins into the vascular system during surgery. All tumor and non-tumor samples are collected concurrent with surgery. The disclosed method also includes extracting proteins from the samples 104. Proteins may be extracted by any method known to those of ordinary skill in the art (as previously described). In the present embodiment, proteins are extracted by placing tissue samples into lysis buffer followed by protein extraction using homogenization and sonication. In this embodiment, the method includes protein depletion 106, such as by use of an antibody-based multiple affinity removal system (MARS). Following protein depletion 106, samples are subjected to digestion 108, for example by subjecting the samples to treatment with trypsin in buffered methanol solution. The peptide digests are then fractionated 110 by off-line SCX-LC and analyzed by LC-MS/MS analysis 112. Nano-flow reversed phase liquid chromatography (nfRPLC) coupled to a hybrid linear ion trap (LIT)-Fourier transform ion cyclotron resonance (FTICR) MS can be used to analyze each SCX fraction. Tandem mass spectra are analyzed 114 by SEQUEST against normal and reverse human database allowing a maximum estimated peptide false discovery rate (FDR) of 1%. The identities of specific tumor proteins are elicited by subtractive proteomics 116. Set-based analysis of tumor versus normal tissue identifies a tumor specific subset of proteins. This subset can then be mapped into plasma, thus identifying specific proteins by intersecting both tumor and plasma species.

III. Methods of Diagnosing RCC

Using the method described above, RCC biomarkers were identified. The disclosed RCC gene signature can be used for diagnosing a subject with RCC. Thus, provided herein is a method of determining whether a subject has RCC.

In particular examples, the method includes detecting expression of one or more RCC biomarkers, such as two or more RCC biomarkers, wherein the RCC biomarkers include, consist essentially or, or consist of those disclosed in Table 1 (for example, CDH5, CDH11, DDX23, WWC1, CHD4, NCOA6, PKM2, or VCAM1), and comparing expression of the RCC biomarkers in the tumor sample to a control. Expression of the RCC biomarkers and housekeeping genes can be detected using any suitable means known in the art. For example, detection of gene expression can be accomplished by detecting nucleic acid molecules (such as RNA) using nucleic acid amplification methods (such as RT-PCR) or array analysis. Detection of gene expression can also be accomplished using immunoassays that detect proteins (such as ELISA, Western blot, or RIA assay). Additional methods of detecting gene expression are well known in the art and are described in greater detail below.

In some embodiments, the method includes detecting expression of two or more (such as at least 3, at least 4, at least 5, at least 6, at least 7) RCC biomarkers. In one example, the method includes detecting expression of a plurality of RCC biomarkers in a tumor sample obtained from the subject, wherein the plurality of RCC biomarkers consist essentially of or even consist of CDH5, CDH11, DDX23, WWC1, CHD4, NCOA6, PKM2, and VCAM1. In some examples, housekeeping gene expression is also detected, such as 1 to 10, 1 to five, or one to two housekeeping genes.

In some embodiments of the method, an alteration in expression of two or more RCC biomarkers in the tumor sample relative to the control indicates a diagnosis of the subject with a malignant tumor, such as RCC. In particular examples, an increase in expression of two or more RCC biomarkers in the tumor sample selected from the group consisting of CDH5, CDH11, DDX23, WWC1, CHD4, NCOA6, PKM2, and VCAM1 relative to the control indicates a malignant tumor (e.g., RCC). In some examples, an increase in expression of three or more, four or more, five or more, or each of CDH5, CDH11, DDX23, WWC1, CHD4, NCOA6, PKM2, and VCAM1 in the tumor sample relative to the control indicates a malignant tumor (e.g., RCC). In other examples, no significant change in expression of two or more RCC biomarkers in the tumor sample (for example, CDH5, CDH11, DDX23, WWC1, CHD4, NCOA6, PKM2, and VCAM1) relative to the control indicates a benign (e.g., non-malignant) tumor. In a specific example, no significant change in expression of CDH5, CDH11, DDX23, WWC1, CHD4, NCOA6, PKM2, and VCAM1 relative to the control indicates a benign (e.g., non-malignant) tumor.

The control can be any suitable control against which to compare expression of a RCC biomarker in a tumor sample. In some embodiments, the control sample is non-tumor tissue. In some examples, the non-tumor tissue is obtained from the same subject, such as non-tumor tissue that is adjacent to the tumor. In other examples, the non-tumor tissue is obtained from a healthy control subject. In some embodiments, the control is a reference value or ranges of values. For example, the reference value can be derived from the average expression values obtained from a group of healthy control subjects or non-tumor tissue from a group of cancer patients.

In one example, an increase in expression of two or more of the RCC biomarkers is correlated with a poor prognosis. For example, if expression is compared to a a non-tumor adjacent control or reference value (level of expression known to be present in non-tumor tissues), an increase in expression of about 1.5-fold, about 2-fold, about 2.5-fold, about 3-fold, about 4-fold, about 5-fold, about 7-fold or about 10-fold relative to the control sample, indicates a poor prognosis. In some examples, an increase in expression of about 1.3-fold to about 4-fold, such as about 1.5-fold to 3.5-fold relative to the control sample indicates a poor prognosis. The relative increase in expression level amongst the RCC biomarkers can vary within a tumor and can also vary between tumor samples.

In particular examples, an increase in expression of two or more RCC biomarkers in the tumor sample selected from the group consisting of CDH5, CDH11, DDX23, WWC1, CHD4, NCOA6, PKM2, and VCAM1 relative to the control (e.g., expression level detected in a tissue sample from adjacent non-tumor tissue or a reference value known to be indicative of levels in non-tumorous samples) indicates a poor prognosis. In some examples, an increase in expression of three or more, four or more, five or more, or each of CDH5, CDH11, DDX23, WWC1, CHD4, NCOA6, PKM2, and VCAM1 in the tumor sample relative to the control indicates a poor prognosis. For example, an increase in the expression of CDH5, CDH11, DDX23, WWC1, CHD4, NCOA6, PKM2, or VCAM1 relative to a normal control sample or reference value (or range of values) indicates a poor prognosis, such as a decreased chance of survival (for example decreased overall survival, relapse-free survival, or metastasis-free survival). In an example, a decreased chance of survival includes a survival time of equal to or less than 60 months, such as 50 months, 40 months, 30 months, 20 months, 12 months, 6 months, or 3 months from time of diagnosis or first treatment.

In other examples, no significant change in expression of two or more RCC biomarkers in the tumor sample selected from the group consisting of CDH5, CDH11, DDX23, WWC1, CHD4, NCOA6, PKM2, and VCAM1 relative to the control (e.g., expression level detected in a tissue sample from adjacent non-tumor tissue or a reference value known to be indicative of levels in non-tumorous samples) indicates a good prognosis (such as increased chance of survival, for example increased overall survival, relapse-free survival, or metastasis-free survival). In a specific example, no significant change in expression of CDH5, CDH11, DDX23, WWC1, CHD4, NCOA6, PKM2, and VCAM1 relative to the control indicates a good prognosis (such as increased chance of survival, for example increased overall survival, relapse-free survival, or metastasis-free survival). In an example, an increased chance of survival includes a survival time of at least 50 months from time of diagnosis, such as 60 months, 80 months, 100 months, 120 months or 150 months from time of diagnosis or first treatment.

Poor prognosis can refer to any negative clinical outcome, such as, but not limited to, a decrease in likelihood of survival (such as overall survival, relapse-free survival, or metastasis-free survival), a decrease in the time of survival (e.g., less than 5 years, or less than one year), an increase in the severity of disease, a decrease in response to therapy, an increase in tumor recurrence, an increase in metastasis, or the like. In particular examples, a poor prognosis is a decreased chance of survival (for example, a survival time of equal to or less than 50 months, such as 40 months, 30 months, 20 months, 12 months, 6 months or 3 months from time of diagnosis or first treatment).

IV. Detecting Expression of RCC Biomarkers

As described below, expression of two or more biomarkers, such as RCC biomarkers identified by the method described above, can be detected using any one of a number of methods well known in the art. Expression of mRNA, cDNA or protein is contemplated herein.

A. Methods for Detection of mRNA or cDNA

Gene expression can be evaluated by detecting mRNA encoding the gene of interest. Thus, the disclosed methods can include evaluating mRNA encoding each of two or more of the genes that encode RCC biomarkers disclosed in Table 1. In particular examples, mRNA encoding CDH5, CDH11, DDX23, WWC1, CHD4, NCOA6, PKM2, or VCAM1 is detected. In some examples, the mRNA is quantified.

RNA can be isolated from a sample of a tumor (for example, RCC) from a subject, a sample of adjacent non-tumor tissue from the subject, a sample of tumor-free tissue from a normal (healthy) subject, a blood sample, or combinations thereof, using methods well known to one skilled in the art, including commercially available kits. General methods for mRNA extraction are well known in the art and are disclosed in standard textbooks of molecular biology, including Ausubel et al., *Current Protocols of Molecular Biology*, John Wiley and Sons (1997). Methods for RNA extraction from paraffin embedded tissues are disclosed, for example, in Rupp and Locker, *Biotechniques* 6:56-60 (1988), and De Andres et al., *Biotechniques* 18:42-44 (1995). In one example, RNA isolation can be performed using purification kit, buffer set and protease from commercial manufacturers, such as QIAGEN® (Valencia, Calif.), according to the manufacturer's instructions. For example, total RNA from cells (such as those obtained from a subject) can be isolated using QIAGEN® RNeasy mini-columns Other commercially available RNA isolation kits include MASTERPURE® Complete DNA and RNA Purification Kit (EPICENTRE® Madison, Wis.), and Paraffin Block RNA Isolation Kit (Ambion, Inc.). Total RNA from tissue samples can be isolated using RNA Stat-60 (Tel-Test). RNA prepared from tumor or other biological sample can be isolated, for example, by cesium chloride density gradient centrifugation.

Methods of gene expression profiling include methods based on hybridization analysis of polynucleotides, methods based on sequencing of polynucleotides, and proteomics-based methods. In some examples, mRNA expression in a sample is quantified using Northern blotting or in situ hybridization (Parker & Barnes, *Methods in Molecular Biology* 106:247-283, 1999); RNAse protection assays (Hod, *Biotechniques* 13:852-4, 1992); and PCR-based methods, such as reverse transcription polymerase chain reaction (RT-PCR) (Weis et al., *Trends in Genetics* 8:263-4, 1992). Alternatively, antibodies can be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS). In one example, RT-PCR can be used to compare mRNA levels in different samples, in normal and tumor tissues, with or without drug treatment, to characterize patterns of gene expression, to discriminate between closely related mRNAs, and to analyze RNA structure.

Methods for quantifying mRNA are well known in the art. In some examples, the method utilizes RT-PCR. Generally, the first step in gene expression profiling by RT-PCR is the reverse transcription of the RNA template into cDNA, followed by its exponential amplification in a PCR reaction. Two commonly used reverse transcriptases are avian myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp® RNA PCR kit (Perkin Elmer, Calif.), following the manufacturer's instructions. The derived cDNA can then be used as a template in the subsequent PCR reaction.

Although the PCR step can use a variety of thermostable DNA-dependent DNA polymerases, it typically employs the Taq DNA polymerase. TaqMan® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendable by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments dissociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan® RT-PCR can be performed using commercially available equipment, such as, for example, ABI PRISM 7700® Sequence Detection System® (Perkin-Elmer-Applied Biosystems, Foster City, Calif.), or Lightcycler® (Roche Molecular Biochemicals, Mannheim, Germany). In one example, the 5' nuclease procedure is run on a real-time quantitative PCR device such as the ABI PRISM 7700® Sequence Detection System®.

To minimize errors and the effect of sample-to-sample variation, RT-PCR can be performed using an internal standard. The ideal internal standard is expressed at a constant level among different tissues, and is unaffected by an experimental treatment. RNAs commonly used to normalize patterns of gene expression are mRNAs for the housekeeping genes GAPDH, β-actin, and 18S ribosomal RNA.

A variation of RT-PCR is real time quantitative RT-PCR, which measures PCR product accumulation through a dual-labeled fluorogenic probe (e.g., TAQMAN® probe). Real time PCR is compatible both with quantitative competitive PCR, where internal competitor for each target sequence is used for normalization, and with quantitative comparative PCR using a normalization gene contained within the sample, or a housekeeping gene for RT-PCR (see Heid et al., *Genome Research* 6:986-994, 1996). Quantitative PCR is also described in U.S. Pat. No. 5,538,848. Related probes and quantitative amplification procedures are described in U.S. Pat. No. 5,716,784 and U.S. Pat. No. 5,723,591. Instruments for carrying out quantitative PCR in microtiter plates are available from PE Applied Biosystems (Foster City, Calif.).

The steps of a representative protocol for quantitating gene expression using fixed, paraffin-embedded tissues as the RNA source, including mRNA isolation, purification, primer extension and amplification are given in various published journal articles (see Godfrey et al., *J. Mol. Diag.* 2:84 91, 2000; Specht et al., *Am. J. Pathol.* 158:419-29, 2001). Briefly, a representative process starts with cutting about 10 μm thick sections of paraffin-embedded tumor tissue samples or adjacent non-cancerous tissue. The RNA is then extracted, and protein and DNA are removed. Alternatively, RNA is isolated directly from a tumor sample or other tissue sample. After analysis of the RNA concentration, RNA repair and/or amplification steps can be included, if necessary, and RNA is reverse transcribed using gene specific promoters followed by RT-PCR.

The primers used for the amplification are selected so as to amplify a unique segment of the gene of interest (such as mRNA encoding CDH5, CDH11, DDX23, WWC1, CHD4, NCOA6, PKM2, and/or VCAM1). In some embodiments, expression of other genes is also detected, such as the genes listed in Table 1. Primers that can be used to amplify CDH5, CDH11, DDX23, WWC1, CHD4, NCOA6, PKM2, and VCAM1, as well as housekeeping genes, are commercially available or can be designed and synthesized according to well known methods.

An alternative quantitative nucleic acid amplification procedure is described in U.S. Pat. No. 5,219,727. In this procedure, the amount of a target sequence in a sample is determined by simultaneously amplifying the target sequence and an internal standard nucleic acid segment. The amount of amplified DNA from each segment is determined and compared to a standard curve to determine the amount of the target nucleic acid segment that was present in the sample prior to amplification.

In some examples, gene expression is identified or confirmed using the microarray technique. Thus, the expression profile can be measured in either fresh or paraffin-embedded tumor tissue, using microarray technology. In this method, RCC biomarker nucleic acid sequences of interest (including cDNAs and oligonucleotides) are plated, or arrayed, on a microchip substrate. The arrayed sequences are then hybridized with isolated nucleic acids (such as cDNA or mRNA) from cells or tissues of interest. Just as in the RT-PCR method, the source of mRNA typically is total RNA isolated from human tumors, and optionally from corresponding noncancerous tissue and normal tissues or cell lines.

In particular embodiments provided herein, arrays can be used to evaluate RCC biomarker expression, for example to prognose or diagnose a patient with cancer (for example, RCC). When describing an array that consists essentially of probes or primers specific for the genes listed in Table 1, such an array includes probes or primers specific for these RCC biomarkers, and can further include control probes (for example to confirm the incubation conditions are sufficient). In some examples, the array may consist essentially of probes or primers specific for CDH5, CDH11, DDX23, WWC1, CHD4, NCOA6, PKM2, and/or VCAM1, and can further include control probes. In some examples, the array may further include additional, such as about 5, 10, 20, 30, 40, 50, 60, or 70 additional RCC biomarkers. In other examples, the array may include fewer, such as 1, 2, 3, or 4 fewer RCC biomarkers. Exemplary control probes include GAPDH, β-actin, and 18S RNA. In one example, an array is a multi-well plate (e.g., 98 or 364 well plate).

In one example, the array includes, consists essentially of, or consists of probes or primers (such as an oligonucleotide or antibody) that can recognize CDH5, CDH11, DDX23, WWC1, CHD4, NCOA6, PKM2, and VCAM1. The oligonucleotide probes or primers can further include one or more detectable labels, to permit detection of hybridization signals between the probe and target sequence (such as one of the RCC biomarkers disclosed herein).

In a specific embodiment of the microarray technique, PCR amplified inserts of cDNA clones are applied to a substrate in a dense array. In some examples, the array includes probes specific to at least two of the RCC biomarkers (such as those in Table 1), and in some examples further includes 1 to 10 probes specific for housekeeping genes. At least probes specific for two or more of CDH5, CDH11, DDX23, WWC1, CHD4, NCOA6, PKM2, and VCAM1 nucleotide sequences are applied to the substrate, and the array can consist essentially of, or consist of probes specific for these sequences. The microarrayed nucleic acids are suitable for hybridization under stringent conditions. Fluorescently labeled cDNA probes generated from the biological samples may be generated through incorporation of fluorescent nucleotides by reverse transcription of RNA extracted from tissues of interest. Labeled cDNA applied to the chip hybridize with specificity to each spot of DNA on the array. After stringent washing to remove non-specifically bound sample cDNA, the chip is scanned by confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for RCC biomarker, such as those in Table 1 (for example, CDH5, CDH11, DDX23, WWC1, CHD4, NCOA6, PKM2, and VCAM1). Such methods have been shown to have the sensitivity required to detect rare transcripts, which are expressed at a few copies per cell, and to reproducibly detect at least approximately two-fold differences in the expression levels (Schena et al., *Proc. Natl. Acad. Sci. USA* 93(2):10614-9, 1996). Microarray analysis can be performed by commercially available equipment, following manufacturer's protocols, such as are supplied with Affymetrix GeneChip® technology (Affymetrix, Santa Clara, Calif.), or Agilent's microarray technology (Agilent Technologies, Santa Clara, Calif.).

1. Array Substrates

The solid support of the array can be formed from an organic polymer. Suitable materials for the solid support include, but are not limited to: polypropylene, polyethylene, polybutylene, polyisobutylene, polybutadiene, polyisoprene, polyvinylpyrrolidine, polytetrafluroethylene, polyvinylidene difluroide, polyfluoroethylene-propylene, polyethylenevinyl alcohol, polymethylpentene, polycholorotrifluoroethylene, polysulfornes, hydroxylated biaxially oriented polypropylene, aminated biaxially oriented polypropylene, thiolated biaxially oriented polypropylene, ethyleneacrylic acid, thylene methacrylic acid, and blends of copolymers thereof (see U.S. Pat. No. 5,985,567).

In general, suitable characteristics of the material that can be used to form the solid support surface include: being amenable to surface activation such that upon activation, the surface of the support is capable of covalently attaching a biomolecule such as an oligonucleotide thereto; amenability to "in situ" synthesis of biomolecules; being chemically inert such that at the areas on the support not occupied by the oligonucleotides or proteins (such as antibodies) are not amenable to non-specific binding, or when non-specific binding occurs, such materials can be readily removed from the surface without removing the oligonucleotides or proteins (such as antibodies).

In one example, the solid support surface is polypropylene. Polypropylene is chemically inert and hydrophobic. Non-specific binding is generally avoidable, and detection sensitivity is improved. Polypropylene has good chemical resistance to a variety of organic acids (such as formic acid), organic agents (such as acetone or ethanol), bases (such as sodium hydroxide), salts (such as sodium chloride), oxidizing agents (such as peracetic acid), and mineral acids (such as hydrochloric acid). Polypropylene also provides a low fluorescence background, which minimizes background interference and increases the sensitivity of the signal of interest.

In another example, a surface activated organic polymer is used as the solid support surface. One example of a surface activated organic polymer is a polypropylene material aminated via radio frequency plasma discharge. Such materials are easily utilized for the attachment of nucleotide molecules. The amine groups on the activated organic polymers are reactive with nucleotide molecules such that the nucleotide molecules can be bound to the polymers. Other reactive groups can also be used, such as carboxylated, hydroxylated, thiolated, or active ester groups.

2. Array Formats

A wide variety of array formats can be employed in accordance with the present disclosure. One example includes a linear array of oligonucleotide bands, generally referred to in the art as a dipstick. Another suitable format includes a two-dimensional pattern of discrete cells (such as 4096 squares in a 64 by 64 array). As is appreciated by those skilled in the art, other array formats including, but not limited to slot (rectangular) and circular arrays are equally suitable for use (see U.S. Pat. No. 5,981,185). In some examples, the array is a multi-well plate. In one example, the array is formed on a polymer medium, which is a thread, membrane or film. An example of an organic polymer medium is a polypropylene sheet having a thickness on the order of about 1 mil. (0.001 inch) to about 20 mil., although the thickness of the film is not critical and can be varied over a fairly broad range. The array can include biaxially oriented polypropylene (BOPP) films, which in addition to their durability, exhibit low background fluorescence.

The array formats of the present disclosure can be included in a variety of different types of formats. A "format" includes any format to which the solid support can be affixed, such as microtiter plates (e.g., multi-well plates), test tubes, inorganic sheets, dipsticks, and the like. For example, when the solid support is a polypropylene thread, one or more polypropylene threads can be affixed to a plastic dipstick-type device; polypropylene membranes can be affixed to glass slides. The particular format is, in and of itself, unimportant. All that is necessary is that the solid support can be affixed thereto without affecting the functional behavior of the solid support or any biopolymer absorbed thereon, and that the format (such as the dipstick or slide) is stable to any materials into which the device is introduced (such as clinical samples and hybridization solutions).

The arrays of the present disclosure can be prepared by a variety of approaches. In one example, oligonucleotide or protein sequences are synthesized separately and then attached to a solid support (see U.S. Pat. No. 6,013,789). In another example, sequences are synthesized directly onto the support to provide the desired array (see U.S. Pat. No. 5,554,501). Suitable methods for covalently coupling oligonucleotides and proteins to a solid support and for directly synthesizing the oligonucleotides or proteins onto the support are known to those working in the field; a summary of suitable methods can be found in Matson et al., *Anal. Biochem.* 217: 306-10, 1994. In one example, the oligonucleotides are synthesized onto the support using conventional chemical techniques for preparing oligonucleotides on solid supports (such as PCT applications WO 85/01051 and WO 89/10977, or U.S. Pat. No. 5,554,501).

A suitable array can be produced using automated means to synthesize oligonucleotides in the cells of the array by laying down the precursors for the four bases in a predetermined pattern. Briefly, a multiple-channel automated chemical delivery system is employed to create oligonucleotide probe populations in parallel rows (corresponding in number to the number of channels in the delivery system) across the substrate. Following completion of oligonucleotide synthesis in a first direction, the substrate can then be rotated by 90° to permit synthesis to proceed within a second set of rows that are now perpendicular to the first set. This process creates a multiple-channel array whose intersection generates a plurality of discrete cells.

The oligonucleotides can be bound to the polypropylene support by either the 3' end of the oligonucleotide or by the 5' end of the oligonucleotide. In one example, the oligonucleotides are bound to the solid support by the 3' end. However, one of skill in the art can determine whether the use of the 3' end or the 5' end of the oligonucleotide is suitable for bonding to the solid support. In general, the internal complementarity of an oligonucleotide probe in the region of the 3' end and the 5' end determines binding to the support.

In particular examples, the oligonucleotide probes on the array include one or more labels, that permit detection of oligonucleotide probe:target sequence hybridization complexes.

Serial analysis of gene expression (SAGE) is another method that allows the simultaneous and quantitative analysis of a large number of gene transcripts, without the need of providing an individual hybridization probe for each transcript. First, a short sequence tag (about 10-14 base pairs) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag (see, for example, Velculescu et al., *Science* 270:484-7, 1995; and Velculescu et al., *Cell* 88:243-51, 1997).

In situ hybridization (ISH) is another method for detecting and comparing expression of genes of interest. ISH applies and extrapolates the technology of nucleic acid hybridization to the single cell level, and, in combination with the art of cytochemistry, immunocytochemistry and immunohistochemistry, permits the maintenance of morphology and the identification of cellular markers to be maintained and identified, and allows the localization of sequences to specific cells within populations, such as tissues and blood samples. ISH is a type of hybridization that uses a complementary nucleic acid to localize one or more specific nucleic acid sequences in a portion or section of tissue (in situ), or, if the tissue is small enough, in the entire tissue (whole mount ISH). RNA ISH can be used to assay expression patterns in a tissue, such as the expression of RCC biomarkers.

Sample cells or tissues are treated to increase their permeability to allow a probe, such as an RCC biomarker-specific probe, to enter the cells. The probe is added to the treated cells, allowed to hybridize at pertinent temperature, and excess probe is washed away. A complementary probe is labeled with a radioactive, fluorescent or antigenic tag, so that the probe's location and quantity in the tissue can be determined using autoradiography, fluorescence microscopy or immunoassay. The sample may be any sample as herein described, such as a non-cancerous kidney sample. Since the sequences of the RCC biomarkers of interest are known, probes can be designed accordingly such that the probes specifically bind the gene of interest.

In situ PCR is the PCR-based amplification of the target nucleic acid sequences prior to ISH. For detection of RNA, an intracellular reverse transcription step is introduced to generate complementary DNA from RNA templates prior to in situ PCR. This enables detection of low copy RNA sequences.

Prior to in situ PCR, cells or tissue samples are fixed and permeabilized to preserve morphology and permit access of the PCR reagents to the intracellular sequences to be amplified. PCR amplification of target sequences is next performed either in intact cells held in suspension or directly in cytocentrifuge preparations or tissue sections on glass slides. In the former approach, fixed cells suspended in the PCR reaction mixture are thermally cycled using conventional thermal cyclers. After PCR, the cells are cytocentrifuged onto glass slides with visualization of intracellular PCR products by ISH or immunohistochemistry. In situ PCR on glass slides is performed by overlaying the samples with the PCR mixture under a coverslip which is then sealed to prevent evaporation of the reaction mixture. Thermal cycling is achieved by placing the glass slides either directly on top of the heating block of a conventional or specially designed thermal cycler or by using thermal cycling ovens.

Detection of intracellular PCR products is generally achieved by one of two different techniques, indirect in situ PCR by ISH with PCR-product specific probes, or direct in situ PCR without ISH through direct detection of labeled nucleotides (such as digoxigenin-11-dUTP, fluorescein-dUTP, 3H-CTP or biotin-16-dUTP), which have been incorporated into the PCR products during thermal cycling.

In some embodiments of the detection methods, the expression of one or more "housekeeping" genes or "internal controls" can also be evaluated. These terms include any constitutively or globally expressed gene (or protein, as discussed below) whose presence enables an assessment of RCC biomarker gene (or protein) levels. Such an assessment includes a determination of the overall constitutive level of gene transcription and a control for variations in RNA (or protein) recovery.

B. Detecting RCC Biomarker Proteins

In some examples, expression of two or more proteins disclosed in Table 1 is analyzed. In particular examples, CDH5, CDH11, DDX23, WWC1, CHD4, NCOA6, PKM2, and VCAM1 proteins are analyzed. Suitable biological samples include samples containing protein obtained from a tumor (such as RCC sample) of a subject, from non-tumor tissue of the subject, from a blood sample from the subject, and/or protein obtained from one or more samples of cancer-free tissue samples or subjects. An alteration in the amount of two or more proteins in Table 1 (such as CDH5, CDH11, DDX23, WWC1, CHD4, NCOA6, PKM2, or VCAM1) in a tumor from the subject relative to a control, such as an increase or decrease in expression, indicates the prognosis or diagnosis of the subject, as described above.

Antibodies specific for the disclosed proteins (for example, CDH5, CDH11, DDX23, WWC1, CHD4, NCOA6, PKM2, and VCAM1) can be used for detection and quantification of RCC biomarker proteins by one of a number of immunoassay methods that are well known in the art, such as those presented in Harlow and Lane (Antibodies, A Laboratory Manual, CSHL, New York, 1988). Methods of constructing such antibodies are known in the art. In addition, such antibodies may be commercially available. Exemplary commercially available antibodies include those that are available from Santa Cruz Biotechnologies (Santa Cruz, Calif.). Any standard immunoassay format (such as ELISA, Western blot, or RIA assay) can be used to measure protein levels. Thus, in one example, polypeptide levels of two or more of CDH5, CDH11, DDX23, WWC1, CHD4, NCOA6, PKM2, and VCAM1 in a tumor (for example, RCC) can readily be evaluated using these methods. Immunohistochemical techniques can also be utilized for RCC biomarker detection and quantification. General guidance regarding such techniques can be found in Bancroft and Stevens (*Theory and Practice of Histological Techniques*, Churchill Livingstone, 1982) and Ausubel et al. (*Current Protocols in Molecular Biology*, John Wiley & Sons, New York, 1998).

For the purposes of quantifying RCC biomarker proteins, a biological sample of the subject that includes cellular proteins can be used. Quantification of proteins (for example, CDH5, CDH11, DDX23, WWC1, CHD4, NCOA6, PKM2, or VCAM1) can be achieved by immunoassay. The amount of RCC biomarker proteins can be assessed in the tumor and optionally in the adjacent non-tumor tissue or in tissue from cancer-free subjects. The amounts of RCC biomarker protein in the tumor can be compared to levels of the protein found in cells from a cancer-free subject, tissue or other control (such as a standard value or reference value). A significant increase or decrease in the amount can be evaluated using statistical methods known in the art.

Quantitative spectroscopic methods, such as SELDI, can be used to analyze RCC biomarker protein expression in a sample (such as tumor tissue, non-cancerous tissue, and tissue from a cancer-free subject). In one example, surface-enhanced laser desorption-ionization time-of-flight (SELDI-TOF) mass spectrometry is used to detect protein expression, for example by using the ProteinChip™ (Ciphergen Biosystems, Palo Alto, Calif.). Such methods are well known in the art (for example see U.S. Pat. No. 5,719,060; U.S. Pat. No. 6,897,072; and U.S. Pat. No. 6,881,586). SELDI is a solid phase method for desorption in which the analyte is presented to the energy stream on a surface that enhances analyte capture or desorption.

Briefly, one version of SELDI uses a chromatographic surface with a chemistry that selectively captures analytes of interest, such as RCC biomarker proteins. Chromatographic surfaces can be composed of hydrophobic, hydrophilic, ion exchange, immobilized metal, or other chemistries. For example, the surface chemistry can include binding functionalities based on oxygen-dependent, carbon-dependent, sulfur-dependent, and/or nitrogen-dependent means of covalent or noncovalent immobilization of analytes. The activated surfaces are used to covalently immobilize specific "bait" molecules such as antibodies, receptors, or oligonucleotides often used for biomolecular interaction studies such as protein-protein and protein-DNA interactions.

The surface chemistry allows the bound analytes to be retained and unbound materials to be washed away. Subsequently, analytes bound to the surface (such as RCC biomarker proteins) can be desorbed and analyzed by any of several means, for example using mass spectrometry. When the analyte is ionized in the process of desorption, such as in laser desorption/ionization mass spectrometry, the detector can be an ion detector. Mass spectrometers generally include means for determining the time-of-flight of desorbed ions. This information is converted to mass. However, one need not determine the mass of desorbed ions to resolve and detect them: the fact that ionized analytes strike the detector at different times provides detection and resolution of them. Alternatively, the analyte can be detectably labeled (for example with a fluorophore or radioactive isotope). In these cases, the detector can be a fluorescence or radioactivity detector. A plurality of detection means can be implemented in series to fully interrogate the analyte components and function associated with retained molecules at each location in the array.

Therefore, in a particular example, the chromatographic surface includes antibodies that specifically bind CDH5, CDH11, DDX23, WWC1, CHD4, NCOA6, PKM2, and VCAM1. In other examples, the chromatographic surface consists essentially of, or consists of, antibodies that specifically bind CDH5, CDH11, DDX23, WWC1, CHD4, NCOA6, PKM2, and VCAM1. In some examples, the chromatographic surface includes antibodies that bind other molecules, such as housekeeping proteins (e.g., β-actin or myosin).

In another example, antibodies are immobilized onto the surface using a bacterial Fc binding support. The chromatographic surface is incubated with a sample, such as a sample of a tumor. The antigens present in the sample can recognize the antibodies on the chromatographic surface. The unbound proteins and mass spectrometric interfering compounds are washed away and the proteins that are retained on the chromatographic surface are analyzed and detected by SELDI-TOF. The MS profile from the sample can be then compared using differential protein expression mapping, whereby relative expression levels of proteins at specific molecular weights are compared by a variety of statistical techniques and bioinformatic software systems.

V. Methods of Identifying RCC Altering Agents

This disclosure has shown, among other things, that differential expression of RCC markers can be used to diagnose and prognose RCC. This discovery permits, for instance, methods for identifying agents that alter RCC marker expression. In specific examples, the method includes identifying an agent that alters activity (such as expression) of one or more of the RCC biomarkers listed in Table 1. For example, genes that encode RCC biomarkers that are upregulated in RCC (see Table 1) can be used to screen for agents that reduce or inhibit this expression or activity. Such identified agents can be used to treat RCC.

In one example, a RCC altering agent is identified by contacting a tumor cell, such as an RCC cell, with one or more test agents under conditions sufficient for the one or more test agents to alter the activity of one or more of the disclosed RCC biomarkers (such as those listed in Table 1). In some examples, multiple RCC biomarkers are screened, such as at least 3, at least 5, or at least 7 of those shown can be assayed in the presence of the test agents. For example, expression of at least 3 RCC biomarkers are detected in the presence and absence of one or more test agents, such as at least 3 test agents, and the expression levels are compared whereby the presence of differential expression of the RCC biomarkers in the presence/absence of the agents indicates that the test agents alter the activity (such as expression level) of such molecules. The one or more test agents can be any substance, including, but not limited to, a protein (such as an antibody), nucleic acid molecule (such as a siRNA), organic compound, inorganic compound, or other molecule of interest. In a particular example, the test agent is a siRNA or antibody specific for any of the disclosed RCC biomarkers that are overexpressed in RCC. In some examples, such siRNAs or antibodies decrease the expression or activity of these RCC biomarkers. The test agents can be contacted with an RCC cell in vitro or in vivo (e.g., by administering the test agent to a laboratory animal model for renal cancer, such as RCC). Agents that reverse the undesired expression or activity can be selected for further study.

In one specific example, the one or more test agent alters the activity (such as the expression level) of at least 1, at least 2, at least 4, at least 5, at least 6, or at least 7 (for example, 1, 2, 3, 4, 5, 6, 7, or 8) molecules associated with RCC listed in Table 1.

A. Agents

Any agent that has potential (whether or not ultimately realized) to alter RCC biomarker expression (for instance in RCC cells), affect RCC biomarker function (such as, decrease RCC biomarker biological activity), affect the interaction (in vivo or in vitro) between an RCC biomarker and one or more of its signal transduction pathway member molecules (such as, its specific binding partners) or otherwise be a RCC biomarker mimetic is contemplated for use in the methods of this disclosure. Such agents may include, but are not limited to, siRNAs, peptides such as for example, soluble peptides, including but not limited to members of random peptide libraries (see, e.g., Lam et al., Nature, 354:82-84, 1991; Houghten et al., Nature, 354:84-86, 1991), and combinatorial chemistry-derived molecular library made of D and/or L configuration amino acids, phosphopeptides (including, but not limited to, members of random or partially degenerate, directed phosphopeptide libraries; see, e.g., Songyang et al., Cell, 72:767-778, 1993), antibodies (including, but not limited to, polyclonal, monoclonal, humanized, anti idiotypic, chimeric or single chain antibodies, and Fab, F(ab')2 and Fab expression library fragments, and epitope-binding fragments thereof), and small organic or inorganic molecules (such as so called natural products or members of chemical combinatorial libraries).

Libraries (such as combinatorial chemical libraries) useful in the disclosed methods include, but are not limited to, peptide libraries (see, e.g., U.S. Pat. No. 5,010,175; Furka, Int. J. Pept. Prot. Res., 37:487 493, 1991; Houghton et al., Nature, 354:84-88, 1991; PCT Publication No. WO 91/19735), encoded peptides (e.g., PCT Publication WO 93/20242), random bio-oligomers (e.g., PCT Publication No. WO 92/00091), nucleic acid libraries (see Sambrook et al. Molecular Cloning, A Laboratory Manual, Cold Springs Harbor Press, N.Y., 1989; Ausubel et al., Current Protocols in Molecular Biology, Green Publishing Associates and Wiley Interscience, N.Y., 1989), peptide nucleic acid libraries (see, e.g., U.S. Pat. No. 5,539,083), antibody libraries (see, e.g., Vaughn et al., Nat. Biotechnol., 14:309-314, 1996; PCT App. No. PCT/US96/10287), carbohydrate libraries (see, e.g., Liang et al., Science, 274:1520-1522, 1996; U.S. Pat. No. 5,593,853), small organic molecule libraries and the like.

Libraries useful for the disclosed screening methods can be produced in a variety of manners including, but not limited to, spatially arrayed multi-pin peptide synthesis (Geysen, et al., Proc. Natl. Acad. Sci., 81(13):3998 4002, 1984), "tea bag" peptide synthesis (Houghten, Proc. Natl. Acad. Sci., 82(15): 5131 5135, 1985), phage display (Scott and Smith, Science, 249:386-390, 1990), spot or disc synthesis (Dittrich et al., Bioorg. Med. Chem. Lett., 8(17):2351 2356, 1998), or split and mix solid phase synthesis on beads (Furka et al., Int. J. Pept. Protein Res., 37(6):487 493, 1991; Lam et al., Chem. Rev., 97(2):411-448, 1997). Libraries may include a varying number of compositions (members), such as up to about 100 members, such as up to about 1000 members, such as up to about 5000 members, such as up to about 10,000 members, such as up to about 100,000 members, such as up to about 500,000 members, or even more than 500,000 members.

In one embodiment, high throughput screening methods involve providing a nucleic acid (e.g., RNAi) or antibody library containing a large number of potential therapeutic compounds (e.g., potential RCC biomarker altering agents, mimetics, or affectors of signal transduction molecule interaction). Such libraries are then screened in one or more assays as described herein to identify those library members (particularly chemical species or subclasses) that display a desired characteristic activity (such as decreasing RCC biomarker expression, affecting RCC biomarker signal transduction pathway, or specific binding to a RCC biomarker specific antibody). The compounds thus identified can serve as conventional "lead compounds" or can themselves be used as potential or actual therapeutics. In some instances, pools of candidate agents may be identified and further screened to determine which individual or subpools of agents in the collective have the desired activity.

B. Assays

Screening methods may include, but are not limited to, methods employing solid phase, liquid phase, cell based or virtual (in silico) screening assays. In some exemplary assays, compounds that affect the expression or a function of a RCC biomarker (such as decrease expression or activity of RCC biomarkers upregulated in RCC) are identified. For instance, certain assays may identify compounds that bind to a RCC biomarker gene regulatory sequence (e.g., promoter sequences) and which may modulate RCC biomarker gene expression (e.g., decrease expression or activity of such molecules that are overexpressed in RCC samples). Other representative assays identify compounds that interfere with or otherwise affect a protein-protein interaction between a RCC biomarker protein and one or more of its signal transduction pathway members (such as a specific binding partners), or compounds that are specifically recognized by an anti-RCC biomarker antibody. Compounds identified via assays such as those described herein may be useful, for example, for treating RCC or to design and/or further identify RCC treatments.

1. Agents that Modulate the Expression of a RCC Biomarker Gene, Transcript or Polypeptide Also disclosed herein are methods of identifying agents that modulate the expression of a RCC biomarker polypeptide or a nucleic acid molecule encoding it. Generally, such methods involve contacting (directly or indirectly) with a test agent an expression system comprising a nucleic acid sequence encoding a RCC biomarker polypeptide, or a reporter gene operably linked to a RCC biomarker transcription regulatory sequence, and detecting a change (e.g., a decrease or increase) in the expression of the RCC biomarker encoding nucleic acid or reporter gene. "Test agent" as used herein include all agents (and libraries of agents) described above.

Modulation of the expression of a RCC biomarker gene or gene product (e.g., transcript or protein) can be determined using any expression system capable of expressing a RCC biomarker polypeptide or transcript (such as a cell, tissue, or organism, or in vitro transcription or translation systems). In some embodiments, cell based assays are performed. Non limiting exemplary cell based assays may involve test cells such as cells (including cell lines) that normally express a RCC biomarker gene, its corresponding transcript(s) and/or RCC biomarker protein(s), or cells (including cell lines) that have been transiently transfected or stably transformed with a reporter construct driven by a regulatory sequence of a RCC biomarker gene.

As mentioned above, some disclosed methods involve cells (including cell lines) that have been transiently transfected or stably transformed with a reporter construct driven by a regulatory sequence of a RCC biomarker gene. A "regulatory sequence" as used herein can include some or all of the regulatory elements that regulate the expression of a particular nucleic acid sequence (such as a RCC biomarker gene) under normal circumstances. In particular examples, a regulatory region includes the contiguous nucleotides located at least 100, at least 500, at least 1000, at least 2500, at least 5000, or at least 7500 nucleotides upstream of the transcriptional start site of the regulated nucleic acid sequence (such as a RCC biomarker gene).

In method embodiments involving a cell transiently or stably transfected with a reporter construct operably linked to a RCC biomarker gene regulatory region, the level of the reporter gene product can be measured. Reporter genes are nucleic acid sequences that encode readily assayed proteins. Numerous reporter genes are commonly known and methods of their use are standard in the art. Non limiting representative reporter genes are luciferase, β galactosidase, chloramphenicol acetyl transferase, alkaline phosphatase, green fluorescent protein, and others. In the applicable methods, the reporter gene product is detected using standard techniques for that particular reporter gene product (see, for example, manufacturer's directions for human placental alkaline phosphatase (SEAP), luciferase, or enhance green fluorescent protein (EGPF) available from BDBiosciences (Clontech); or galactosidase/luciferase, luciferase, or galactosidase available from Applied Biosystems (Foster City, Calif., USA); or available from various other commercial manufacturers of reporter gene products). A difference in the level and/or activity of reporter gene measure in cells in the presence or absence of a test agent indicates that the test agent modulates the activity of the RCC biomarker regulatory region driving the reporter gene.

A change in the expression of a RCC biomarker gene (or a reporter gene), transcript or protein can be determined by any method known in the art. For example, the levels of a RCC biomarker (or reporter gene) transcript or protein can be measured by standard techniques, such as for RNA, Northern blot, PCR (including RT PCR or q PCR), in situ hybridization, or nucleic acid microarray, or, for protein, Western blot, antibody array, or immunohistochemistry. Alternatively, test cells can be examined to determine whether one or more cellular phenotypes have been altered in a manner consistent with modulation of expression of RCC biomarker.

2. Agents that Affect the Interaction Between RCC Biomarkers and their Signal Transduction Pathway Members Differential expression of one or more of the disclosed RCC biomarkers may result in alterations of the signal transduction pathway member molecules regulated by the RCC biomarkers. Agents that affect an interaction between RCC biomarker and one or more of its signal transduction family members can be identified by a variety of assays, including solid phase or solution based assays. In a solid phase assay, a RCC biomarker polypeptide (as described in detail elsewhere in this specification) and one or more RCC biomarker signal transduction molecules are mixed under conditions in which RCC biomarker and its signaling molecule(s) normally interact. One of the molecules (e.g., a RCC biomarker polypeptide or its specific signaling transduction molecule(s)) is labeled with a marker such as biotin, fluoroscein, EGFP, or enzymes to allow easy detection of the labeled component. The unlabeled binding partner is adsorbed to a support, such as a microtiter well or beads. Then, the labeled binding partner is added to the environment where the unlabeled molecule is immobilized under conditions suitable for interaction between the two molecules. One or more test compounds, such as compounds in one or more of the above described libraries, are separately added to individual microenvironments containing the interacting molecules. Agents capable of affecting the interaction between such molecules are identified, for instance, as those that enhance or reduce retention or binding of the signal (i.e., labeled molecule) in the reaction microenvironment, for example, in a microtiter well or on a bead for example. As discussed previously, combinations of agents can be evaluated in an initial screen to identify pools of agents to be tested individually, and this process is easily automated with currently available technology.

In still other methods, solution phase selection can be used to screen large complex libraries for agents that specifically affect protein-protein interactions (see, e.g., Boger et al., Bioorg. Med. Chem. Lett., 8(17):2339 2344, 1998); Berg et al., Proc. Natl. Acad. Sci., 99(6):3830 3835, 2002). In this example, each of two proteins that are capable of physical interaction (for example, RCC biomarker and one of its respective signal transduction molecules) is labeled with fluorescent dye molecule tags with different emission spectra and overlapping adsorption spectra. When these protein components are separate, the emission spectrum for each component is distinct and can be measured. When the protein components interact, fluorescence resonance energy transfer (FRET) occurs resulting in the transfer of energy from a donor dye molecule to an acceptor dye molecule without emission of a photon. The acceptor dye molecule alone emits photons (light) of a characteristic wavelength. Therefore, FRET allows one to determine the kinetics of two interacting molecules based on the emission spectra of the sample. Using this system, two labeled protein components are added under conditions where their interaction resulting in FRET emission spectra. Then, one or more test compounds, such as compounds in one or more of the above described libraries, are added to the environment of the two labeled protein component mixture and emission spectra are measured. An increase in the FRET emission, with a concurrent decrease in the emission spectra of the separated components indicates that an agent (or pool of candidate agents) has affected (e.g., enhanced) the interaction between the protein components.

Interactions between RCC biomarker and one or more of its specific signal transduction family members also can be determined (e.g., quantitatively or qualitatively) by co immunoprecipitation of the relevant component polypeptides (e.g., from cellular extracts), by GST pull down assay (e.g., using purified GST tagged bacterial proteins), and/or by yeast two hybrid assay, each of which methods is standard in the art. Conducting any one or more such assays in the presence and, optionally, absence of a test compound can be used to identify agents that affect the RCC biomarker:specific signal transduction member interaction in the presence of the test compound as compared to in the absence of the test compound or as compared to some other standard or control. In particular methods, the formation of a RCC biomarker:specific-signal transduction member complex is decreased or inhibited when the amount of such complex is at least 20%, at least 30%, at least 50%, at least 100% less than a control measurement (e.g., in the same test system prior to addition of a test agent, or in a comparable test system in the absence of a test agent). In some methods, inhibition of a RCC biomarker:specific signal transduction member interaction may be nearly complete such that substantially no protein protein complex involving RCC biomarker and that particular specific binding partner is detected using traditional detection methods. In other methods, the formation of a RCC biomarker:specific-signal transduction member complex is increased or enhanced when the amount of such complex is at least 20%, at least 30%, at least 50%, at least 100% or at least 250% higher than a control measurement (e.g., in the same test system prior to addition of a test agent, or in a comparable test system in the absence of a test agent).

3. Identifying Agents that Affects a RCC Biomarker Function/Activity

RCC biomarker differential expression can regulate RCC. Accordingly, it is desirable to identify agents having the potential to alter one or more of these RCC biomarker functions/activities (e.g., inhibit biological activity of up-regulated RCC biomarkers in RCC), at least, because such agents are candidates for RCC therapeutics. As previously described, an alteration in the activity of one or more of the disclosed RCC biomarkers includes an increase or decrease in production of a gene product, such as RNA or protein. For example, an alteration can include processes that downregulate or decrease transcription of a gene or translation of mRNA. Agents that downregulate or inhibit expression or biological activity any of the genes listed in Table 1 are candidate agents for treating RCC. Gene downregulation includes any detectable decrease in the production of a gene product. In certain examples, production/expression of a gene product decreases by at least 2-fold, for example at least 3-fold or at least 4-fold, as compared to a control (such an amount of gene expression in a normal cell or an amount of expression in absence of the test agent). In one example, a control is a relative amount of gene expression or protein expression in a biological sample (e.g., kidney sample) obtained from a subject who does not have RCC. Exemplary assays to identify such agents can involve detecting a RCC biomarker dependent functional (e.g., phenotypic) difference in an in vitro or in vivo assay system. In these embodiments, the assay system is capable of undergoing the desired phenotypic change, e.g., decreasing or inhibiting the progression of RCC. Accordingly, certain cell based systems are suitable for conducting such assays. In particular embodiments, the same type of cell is used for test and control assay systems.

To ensure that an observed phenotype is attributable to a RCC biomarker polypeptide that is upregulated in RCC (such as those listed in Table 1), a control assay system will express substantially no RCC biomarker (e.g., undetectable by Western blot) or substantially less RCC biomarker as compared to a non control assay system. In this context, substantially less means at least 25% less, at least 50% less, at least 75%, or at least 90% less RCC biomarker in the control versus non control assay system. A non control assay system expresses or overexpresses RCC biomarker (or otherwise is treated to have more RCC biomarker) as compared to control (e.g., at least 10%, at least 25%, at least 50%, at least 75%, or at least 90% more RCC biomarker expression than control). In some examples, such expression or overexpression is achieved by transfecting one or more cells with an expression vector encoding the RCC biomarker polypeptide. In some examples, a GST RCC biomarker fusion protein can be expressed either in a transfected cell or transgenic animal. The GST module of such fusion protein permits rapid identification of RCC biomarker expressing cells.

One or more test agents are contacted to the control and non control assay systems (e.g., cells of such assay systems), and a RCC biomarker dependent phenotype (such as responsiveness to immunotherapy) is detected. An agent having potential to reduce or inhibit RCC progression is one for which responsiveness to immunotherapy is greater in the non control, RCC biomarker expressing or overexpressing system. For instance, in one specific non limiting example, GFP positive RCC biomarker overexpressing RCC cells are isolated from transgenic mice (e.g., expressing a heterologous GFP RCC biomarker fusion protein) are cultured on in the presence of test compounds or vehicle. Compounds are identified that attenuate RCC biomarker activity or expression in cells when compared to control cells (cells receiving only vehicle). The GFP marker permits this assay to be used in a high throughput automatic screening format using an imaging system.

In some cell based method embodiments described here and throughout the specification, test cells or test agents can be presented in a manner suitable for high throughput screening; for example, one or a plurality of test cells can be seeded into wells of a microtitre plate, and one or a plurality of test agents can be added to the wells of the microtitre plate. Alternatively, one or a plurality of test agents can be presented in a high throughput format, such as in wells of microtitre plate (either in solution or adhered to the surface of the plate), and contacted with one or a plurality of test cells under conditions that, at least, sustain the test cells. Test agents can be added to test cells at any concentration that is not lethal to the cells. It is expected that different test agents will have different effective concentrations. Thus, in some methods, it is advantageous to test a range of test agent concentrations.

In particular methods, a function of a RCC biomarker polypeptide that is upregulated in RCC is reduced or inhibited when a quantitative or qualitative measure of such function is at least 20%, at least 30%, at least 50%, at least 100% or at least 250% less than a control measurement (e.g., in the same test system prior to addition of a test agent, in a comparable test system in the absence of a test agent or in test system treated with vehicle alone).

VI. Application of a Gene Signature for Treatment of Cancer

It is disclosed herein that expression of the proteins disclosed in Table 1 correlate with clinical outcome of cancer patients (such as RCC patients). In a particular example, an increase in expression or activity of two or more of (such as all of) CDH5, CDH11, DDX23, WWC1, CHD4, NCOA6, PKM2, and VCAM1 indicates a diagnosis of a malignant tumor, such as RCC. Based on these observations, methods of treatment of RCC are disclosed, for example by decreasing expression or activity of one or more of the genes listed in Table 1.

A. Methods of Treatment

Provided herein is a method of treating cancer (for example, epithelial cancer, such as RCC) in a subject, including administering to the subject a therapeutically effective amount of one or more agents that alter (increases or decreases) expression or activity of at least one RCC biomarker, for example, CDH5, CDH11, DDX23, WWC1, CHD4, NCOA6, PKM2, or VCAM1. In certain examples, the one or more agents decrease expression of CDH5, CDH11, DDX23, WWC1, CHD4, NCOA6, PKM2, and/or VCAM1. Such agents can alter the expression of nucleic acid sequences (such as DNA, cDNA, or mRNAs) or proteins. In other examples, the one or more agents decrease the biological activity of CDH5, CDH11, DDX23, WWC1, CHD4, NCOA6, PKM2, and/or VCAM1. An alteration in the expression or activity can be any detectable increase or decrease that results in a biological effect. For example, an agent can increase or decrease the expression or activity by a desired amount, for example by at least about 1.5-fold, at least about 2-fold, at least about 2.5-fold, at least about 3-fold, at least about 4-fold, at least about 5-fold, at least about 7-fold, or at least about 10-fold relative to activity or expression in a control (for example, the relative amount of expression in the absence of treatment).

Treatment of cancer by altering the expression or activity of one or more of the disclosed RCC biomarkers (such as decreasing the expression or activity of one or more of CDH5, CDH11, DDX23, WWC1, CHD4, NCOA6, PKM2, and VCAM1 by a desired amount, such as at least 10%, at least 20%, at least 50%, at least 70% or even at least 90%) can include delaying the development of the tumor in a subject (such as preventing metastasis of a tumor), increasing survival (for example, overall survival, relapse-free survival, or metastasis-free survival, such as increased survival time compared to in the absence of treatment), or combinations thereof. Treatment of a tumor also includes reducing signs or symptoms associated with the presence of such a tumor (for example by reducing the size or volume of the tumor or a metastasis thereof). Such reduced growth can in some examples decrease or slow metastasis of the tumor, or reduce the size or volume of the tumor by at least 10%, at least 20%, at least 50%, or at least 75%. Increased survival can include e.g., survival time of at least about 50 months from time of diagnosis, such as about 60 months, about 80 months, about 100 months, about 120 months or about 150 months from time of diagnosis or first treatment.

In some embodiments, a subject is screened to determine if they would benefit from treatment with an agent that alters (increases or decreases) expression or activity of at least one RCC biomarker, for example, decreasing the expression or activity of one or more of CDH5, CDH11, DDX23, WWC1, CHD4, NCOA6, PKM2, or VCAM1. In some examples, expression of at least one RCC biomarker (such as CADH5, CADH11, DDX23, WWC1, CHD4, NCOA6, PKM2, or VCAM1) is determined in a sample from the subject. If the expression of at least one RCC biomarker is altered (for example, increased) relative to a normal control sample, the subject may be treated with an agent that alters (e.g., decreases) expression or activity of the at least one RCC biomarker. In other examples, expression of at least one RCC biomarker (such as CADH5, CADH11, DDX23, WWC1, CHD4, NCOA6, PKM2, or VCAM1) is determined in a sample from the subject, and if the expression of at least one RCC biomarker is increased, the subject is determined to have a malignant tumor and may be treated with an agent that decreases expression or activity of the at least one RCC biomarker.

In some embodiments, the agent is a specific binding agent, such as an antibody, antisense compound or small molecule inhibitor, that decreases the activity or expression of a target gene. Methods of preparing antibodies against a specific target protein are well known in the art. An RCC biomarker protein or a fragment or conservative variant thereof can be used to produce antibodies which are immunoreactive or specifically bind to an epitope of the RCC biomarker protein. Polyclonal antibodies, antibodies which consist essentially of pooled monoclonal antibodies with different epitopic specificities, as well as distinct monoclonal antibody preparations and chimeric antibodies are included. The preparation of polyclonal antibodies is well known to those skilled in the art. See, for example, Green et al., "Production of Polyclonal Antisera," in: *Immunochemical Protocols*, pages 1-5, Manson, ed., Humana Press, 1992; Coligan et al., "Production of Polyclonal Antisera in Rabbits, Rats, Mice and Hamsters," in: Current Protocols in Immunology, section 2.4.1, 1992. The preparation of monoclonal antibodies likewise is conventional (see, for example, Kohler & Milstein, *Nature* 256:495, 1975; Coligan et al., sections 2.5.1-2.6.7; and Harlow et al. in: *Antibodies: a Laboratory Manual*, page 726, Cold Spring Harbor Pub., 1988).

Any type of antisense compound that specifically targets and regulates expression of target nucleic acid (such as a RCC biomarker gene or downstream target thereof) is contemplated for use. In some examples, the agent is an antisense compound selected from an antisense oligonucleotide, a siRNA, a miRNA, a shRNA or a ribozyme. Methods of designing, preparing and using antisense compounds are within the abilities of one of skill in the art. Furthermore, sequences for the disclosed RCC biomarker genes disclosed herein are publicly available. Antisense compounds specifically targeting a RCC biomarker gene (or other target nucleic acid) can be prepared by designing compounds that are complementary to the target nucleotide sequence, such as a mRNA sequence. Antisense compounds need not be 100% complementary to the target nucleic acid molecule to specifically hybridize and regulate expression the target gene. For example, the antisense compound, or antisense strand of the compound if a double-stranded compound, can be at least 75%, at least 80%, at least 85%, at least 90%, at least 95%, at least 99% or 100% complementary to the selected target nucleic acid sequence. Methods of screening antisense compounds for specificity are well known in the art (see, for example, U.S. Pre-Grant Publication No. 2003-0228689).

B. Therapeutic Agents

Therapeutic agents are agents that when administered in therapeutically effective amounts induce the desired response (e.g., treatment of RCC). In one example, therapeutic agents are specific binding agents that bind with higher affinity to a molecule of interest, than to other molecules. For example, a specific binding agent can be one that binds with high affinity to one or more RCC biomarker genes, or a downstream factor that is regulated by one or more of the disclosed RCC tumor biomarker genes, but does not substantially bind to another gene or gene product. For example, the agent can interfere with gene expression (transcription, processing, translation, post-translational modification), such as, by interfering with the gene's mRNA and blocking translation of the gene product or by post-translational modification of a gene product, or by causing changes in intracellular localization. In another example, a specific binding agent binds to a protein encoded by one or more RCC biomarker genes, or a downstream target of a RCC biomarker gene, with a binding affinity in the range of 0.1 to 20 nM and reduces or inhibits the activity of such protein.

Contemplated herein is the use of specific binding agents to decrease expression or activity of one or more RCC biomarker genes, such as the genes shown in Table 1 (for example, CDH5, CDH11, DDX23, WWC I, CHD4, NCOA6, PKM2, or VCAM1).

Examples of specific binding agents include antisense compounds (such as antisense oligonucleotides, siRNAs, miRNAs, shRNAs and ribozymes), antibodies, ligands, recombinant proteins, peptide mimetics, and soluble receptor fragments. Methods of making antisense compounds that can be used clinically are known in the art. In addition, antisense compounds may be commercially available. Exemplary commercially available antisense compounds are available from Santa Cruz Biotechnology, Inc. (Santa Cruz, Calif. 95060).

Further examples of specific binding agents include antibodies. Methods of making antibodies that can be used clinically are known in the art. In addition, antibodies may be commercially available, such as those discussed above.

Specific binding agents can be therapeutic, for example by altering the biological activity of a RCC biomarker nucleic acid or protein, or a nucleic acid or protein that is negatively regulated by a RCC biomarker gene. For example, a specific binding agent that binds with high affinity to a RCC biomarker gene, or a downstream target of a RCC biomarker gene, may substantially reduce the biological function of the gene or gene product. In other examples, a specific binding agent that binds with high affinity to one of the proteins encoded by a RCC biomarker gene, or a downstream target of a RCC biomarker gene, may substantially reduce the biological function of the protein. Such agents can be administered in therapeutically effective amounts to subjects in need thereof, such as a subject having cancer.

C. Administration of Therapeutic Agents

Therapeutic agents can be administered to a subject in need of treatment using any suitable means known in the art. Methods of administration include, but are not limited to, intradermal, intramuscular, intraperitoneal, parenteral, intravenous, subcutaneous, vaginal, rectal, intranasal, inhalation, oral, or by gene gun. Intranasal administration refers to delivery of the compositions into the nose and nasal passages through one or both of the nares and can include delivery by a spraying mechanism or droplet mechanism, or through aerosolization of the therapeutic agent.

Administration of the compositions by inhalant can be through the nose or mouth via delivery by spraying or droplet mechanisms. Delivery can be directly to any area of the respiratory system via intubation. Parenteral administration is generally achieved by injection. Injectables can be prepared in conventional forms, either as liquid solutions or suspensions, solid forms suitable for solution of suspension in liquid prior to injection, or as emulsions. Injection solutions and suspensions can be prepared from sterile powders, granules, and tablets. Administration can be systemic or local.

Therapeutic agents can be administered in any suitable manner, preferably with pharmaceutically acceptable carriers. Pharmaceutically acceptable carriers are determined in part by the particular composition being administered, as well as by the particular method used to administer the composition. Accordingly, there is a wide variety of suitable formulations of pharmaceutical compositions of the present disclosure.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Administration can be accomplished by single or multiple doses. The dose required will vary from subject to subject depending on the species, age, weight and general condition of the subject, the particular therapeutic agent being used and its mode of administration. In some examples, the dose of antisense compound (such as siRNA, shRNA, or miRNA) is about 1 mg to about 1000 mg, about 10 mg to about 500 mg, or about 50 mg to about 100 mg. In some examples, the dose of antisense compound is about 1 mg, about 10 mg, about 50 mg, about 100 mg, about 250 mg, about 500 mg or about 1000 mg. In some embodiments, the dose of antisense compound is about 1.0 mg/kg to about 100 mg/kg, or about 5.0 mg/kg to about 500 mg/kg, about 10 mg/kg to about 100 mg/kg, or about 25 to about 50 mg/kg. In some examples, the dose of antisense compound is about 1.0 mg/kg, about 5 mg/kg, about 10 mg/kg, about 12.5 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg or about 100 mg/kg. In some embodiments, the dose of antibody is about 1 mg/kg to about 25 mg/kg, such as about 2 mg/kg to about 15 mg/kg, about 2 mg/kg to about 10 mg/kg, or about 2 mg/kg to about 8 mg/kg. In some examples, the dose of antibody is about 1 mg/kg, about 2 mg/kg, about 4 mg/kg, about 5 mg/kg, about 6 mg/kg, about 8 mg/kg, about 10 mg/kg, about 15 mg/kg, about 20 mg/kg, or about 25 mg/kg. In other embodiments, the dose of antibody is about 50 mg/m2 to about 500 mg/m2, such as about 50 mg/m2 to about 400 mg/m2, about 100 mg/m2 to about 400 mg/m2, or about 250 mg/m2 to about 400 mg/m2. In some examples, the dose is about 50 mg/m2, about 100 mg/m2, about 150 mg/m2, about 200 mg/m2, about 250 mg/m2, about 300 mg/m2, about 400 mg/m2, or about 500 mg/m2. It will be appreciated that these dosages are examples only, and an appropriate dose can be determined by one of ordinary skill in the art using only routine experimentation. In particular examples, additional therapeutic agents include FDA approved treatment regimens for RCC such as high-dose IL-2 (Yang J C et al., *JCO* 2003; 21: 3127-32), subcutaneous low-dose IL-2, interferon alpha-2A (Negrier S et al.; *NEJM* 1998; 338:1272-78), Fluorouracil+Gemcitabine (Rini et al., *JCO* 2000; 18:2419-26), sorafenib (Escudier B et al., (abstract LBA4510) *Proceedings Am Soc Clin Onc,* 2005; 23 (16S, Part I), 380S or Sunitinib (Motzer R J et al., (abstract 4508) *Proceedings Am Soc Clin Onc,* 2005, 23 (16S, Part I) 380S)

Prior to, during, or following administration of a therapeutic amount of an agent that reduces or inhibits RCC due to the interaction of a binding agent with one or more of the disclosed RCC biomarkers, the subject can receive one or more other therapies. In one example, the subject receives one or more treatments to remove or reduce the RCC prior to administration of a therapeutic amount of a composition including a binding agent specific for one or more of the disclosed RCC biomarkers. Examples of such therapies include, but are not limited to, surgical treatment for removal or reduction of the tumor (such as surgical resection, cryotherapy, or chemoembolization), as well as anti-tumor pharmaceutical treatments which can include radiotherapeutic agents, anti-neoplastic chemotherapeutic agents, antibiotics, alkylating agents and antioxidants, kinase inhibitors, and other agents.

Particular examples of additional therapeutic agents that can be used include microtubule binding agents (such as paclitaxel, docetaxel, vinblastine, vindesine, vinorelbine (navelbine), the epothilones, colchicine, dolastatin 15, nocodazole, podophyllotoxin, rhizoxin, and derivatives and analogs thereof), DNA intercalators or cross-linkers (such as cisplatin, carboplatin, oxaliplatin, mitomycins, such as mitomycin C, bleomycin, chlorambucil, cyclophosphamide, and derivatives and analogs thereof), DNA synthesis inhibitors (such as methotrexate, 5-fluoro-5'-deoxyuridine, 5-fluorouracil and analogs thereof), DNA and/or RNA transcription inhibitors (such as actinomycin D, daunorubicin, doxorubicin and derivatives and analogs thereof), antibodies (such as trastuzumab, bevacizumab, cetuximab, panitumumab), enzymes, enzyme inhibitors (such as camptothecin, etoposide, formestane, trichostatin and derivatives and analogs thereof), kinase inhibitors (such as imatinib, gefitinib, and erolitinib), and gene regulators (such as raloxifene, 5-azacytidine, 5-aza-2'-deoxycytidine, tamoxifen, 4-hydroxytamoxifen, mifepristone and derivatives and analogs thereof). Methods and therapeutic dosages of such agents are known to those skilled in the art, and can be determined by a skilled clinician.

Other therapeutic agents, for example anti-tumor agents, that may or may not fall under one or more of the classifications above, also are suitable for administration in combination with the described specific binding agents. By way of example, such agents include adriamycin, apigenin, zebularine, cimetidine, and derivatives and analogs thereof.

In some examples, the subject receiving the therapeutic composition (such as one including a binding agent specific for one or more of the disclosed RCC biomarkers) is also administered interleukin-2 (IL-2), for example via intravenous administration. In particular examples, IL-2 (Chiron Corp., Emeryville, Calif.) is administered at a dose of at least 500,000 IU/kg as an intravenous bolus over a 15 minute period every eight hours beginning on the day after administration of the peptides and continuing for up to 5 days. Doses can be skipped depending on subject tolerance.

In some examples, the disclosed compositions can be co-administered with a fully human antibody to cytotoxic T-lymphocyte antigen-4 (anti-CTLA-4). In some example subjects receive at least 1 mg/kg anti-CTLA-4 (such as 3 mg/kg every 3 weeks or 3 mg/kg as the initial dose with subsequent doses reduced to 1 mg/kg every 3 weeks).

In one example, at least a portion of the tumor (such as a metastatic tumor) is surgically removed (for example via cryotherapy), irradiated, chemically treated (for example via chemoembolization) or combinations thereof, prior to administration of the disclosed therapies (such as administration of a binding agent specific for one or more of the disclosed RCC biomarkers). For example, a subject having a metastatic tumor can have all or part of the tumor surgically excised prior to administration of the disclosed therapies (such as one including a binding agent specific for one or more of the disclosed RCC biomarkers). In an example, one or more chemotherapeutic agents is administered following treatment with a binding agent specific for one or more of the disclosed RCC biomarkers. In another particular example, the subject has RCC and is administered radiation therapy, immunotherapy, or both concurrently with the administration of the disclosed therapies (such as one including a binding agent specific for one or more of the disclosed RCC biomarkers).

VII. Kits

Provided by this disclosure are kits that can be used to diagnose, prognose, or treat RCC that differentially expresses one or more of the disclosed RCC biomarkers. The disclosed kits can include instructional materials disclosing means of use of the compositions in the kit. The instructional materials can be written, in an electronic form (such as a computer diskette or compact disk) or can be visual (such as video files).

Kits are provided that can be used in the therapies and diagnostic assays disclosed herein. For example, kits can include one or more of the disclosed therapeutic compositions (such as a composition including one or more of the siRNAs or antibodies directed to one or more RCC biomarkers upregulated in RCC, such as those in Table 1), one or more of the disclosed gene profile signatures, or combinations thereof. One skilled in the art will appreciate that the kits can include other agents to facilitate the particular application for which the kit is designed.

In some example, a kit is provided for detecting one or more of the disclosed RCC biomarkers in a biological sample, such as serum. Kits for detecting RCC biomarkers can include one or more nucleic acid or antibody probes that specifically bind to the molecules. In an example, a kit includes an array with one or more RCC biomarker molecules (e.g., two or more of those listed in Table 1, such as 2, 3, 4, 5, 6, 7 or 8 of such molecules) and controls, such as positive and negative controls. In other examples, kits include antibodies that specifically bind to one of the RCC biomarkers disclosed herein. In some examples, the antibody is labeled (for example, with a fluorescent, radioactive, or an enzymatic label). Such a diagnostic kit can additionally contain means of detecting a label (such as enzyme substrates for enzymatic labels, filter sets to detect fluorescent labels, appropriate secondary labels such as a secondary antibody, or the like), as well as buffers and other reagents routinely used for the practice of a particular diagnostic method.

The disclosure is further illustrated by the following non-limiting Examples.

Example 1

Materials and Methods

Materials and Reagents.

MARS columns and MARS reagents were purchased from Agilent Technologies (Palo Alto, Calif.). SDS-PAGE materials and reagents were obtained from Invitrogen Life Technologies (Carlsbad, Calif.). Methanol and acetonitrile (HPLC-grade) were purchased from EMD Chemicals (Gibbstown, N.J.). All other chemicals and reagents, except for disclosed ones, were obtained from Sigma-Aldrich (St. Louis, Mo.).

Specimen Collection and Processing.

Clinical specimens were procured by the National Cancer Institute Cooperative Human Tissue Network in accordance with current regulations and guidance issued by the Office of Human Subjects Review. Tumorous fresh frozen tissue, adjacent non-tumor fresh frozen tissue and plasma specimens were collected prospectively from a single patient diagnosed with the RCC using standard clinical procedures and stored at −80° C. Tissue specimens were procured during the surgery while peripheral blood plasma was collected before the surgical procedure.

Each tissue specimen was thawed in ice-cold lysis buffer (1.5 mM NaF, 1.5 mM $Na_3VO_4$, 1.5 mM PMSF, 1.5 mM EDTA and 50 mM $NH_4HCO_3$, final concentration and pH 7.9), homogenized and then incubated for 10 minutes at 95° C. in a water bath. The homogenate was cooled on ice for 20 minutes and centrifuged at 10,000×g to remove tissue debris. The supernatants were collected and protein content determined using a BCA assay (Pierce, Rockford, Ill.). All samples were reduced by adding 1 mM TCEP (final concentration) at 37° C. for 0.5 hours followed by alkylation using 3 mM iodoacetamide (final concentration) at 37° C. for 0.5 hours. High abundant protein depletion was carried out using MARS cartridges (Agilent Technologies, Palo Alto, Calif.). Low abundant flow-through fractions were pooled, desalted, concentrated using Agilent's 5 kDa MWCO Spin Concentrators (Agilent Technologies, Palo Alto, Calif.), and lyophilized. The efficiency of depletion was assessed by comparing the flow through and eluate refraction using 4-12% Bis Tris gel SDS-PAGE (Invitrogen Life Technologies, Carlesbad, Calif.). Plasma sample was depleted using identical procedure and lyophilized. A total of 200 µg of protein from each specimen was resolubilized and subjected to two-step digestion in buffered methanol. The first digestion was carried out in 20% MeOH/50 mM $NH_4HCO_3$ (v/v) using sequencing grade modified trypsin (Promega, Madison, Wis.) at 37° C. overnight and the second digestion in 60% MeOH/50 mM $NH_4HCO_3$ (v/v). Tissue and plasma digestates were then desalted using 3M™ Empore™ C18 High Performance Extraction Disk Cartridges (3M Bioanalytical Technologies, St. Paul, Minn.), lyophilized and stored at −80° C.

2D-LC/MS/MS Analysis.

The tryptic digestates of normal adjacent tissue, tumorous tissue and patient's serum were solubilized and resolved in the first dimension by SCX column (1 mm×150 mm, polysulfoethyl A; PolyLC, Columbia, Md., USA) using microcapillary HPLC system (Model 1100, Agilent Technologies Inc., Palo Alto, Calif.) equipped by UV laser-induced fluorescence detector. Solvent A was 25% (v/v) $CH_3CN$ while solvent B was 25% (v/v) $CH_3CN$ containing 0.5 M ammonium formate, pH 3. Peptide fractions were eluted with an ammonium formate multistep gradient as follows: 1% B/0-2 mM, 10% B/62 mM, 62% B/82 mM, 100% B/85 mM, at a flow rate of 50 µL/min. All collected peptide fractions (n=36) were then individually analyzed in duplicate (2 technical replicates per peptide fraction) using nano-flow RPLC-MS/MS. In-house constructed 75 µm inner diameter×100 mm long fused-silica capillary ESI columns (Polymicro Technologies, Phoenix, Ariz.), slurry-packed with 5 µm, 300 Å pore sized Jupiter C18 RP particles (Phenomenex, Torrence, Calif.) were used to separate/analyze peptide fractions during a 90-mM LC gradient employing an Agilent nanoLC system (Model 1100, Agilent Technologies Inc., Palo Alto, Calif.) coupled online to a 7 T hybrid two-dimensional linear ion-trap—Fourier transform ion cyclotron resonance MS (LTQ-FT, Thermo Electron, San Jose, Calif.). The mass spectrometer was operated in a data-dependent mode to automatically switch between MS and MS/MS. The Fourier transform ion cyclotron resonance MS survey scan (m/z range: 350-1800; nominal resolution setting: $5×10^4$) was followed by linear ion trap MS/MS scans, in which the most abundant seven peptide molecular ions detected in the preceding MS survey scan were dynamically selected for collision induced dissociation (CID). The threshold of 200 ion counts was used for triggering an MS/MS scan. The normalized CID energy was 36%; the electrospray voltage was set at 1.6 kV, and the voltage and temperature for the ion source capillary were set at 45 V and 160° C., respectively.

Data Processing.

All MS/MS spectra from the three distinct clinical specimens were searched independently against the normal and the reversed human protein database (UniProt Human, release September 2007), using the SEQUEST (Thermo Finnigan, San Jose, Calif.). The searches were carried out on a Beowulf 18-node parallel virtual machine computer-cluster, against the normal and the sequence-reversed human proteome database. Dynamic modifications were added for the detection of the following: carboxyamidomethylated cysteine (+57 Da), oxidized methionine (+16 Da). For the FTICR-MS spectra the monoisotopic precursor ion mass tolerance was set at 5 ppm and for the LIT-MS/MS spectra the fragment ion tolerance was set at 0.5 Da. In this investigation sequence-reversed human database was created and used to assess the peptide FDR and establish threshold criteria that permitted a maximum estimated peptide FDR of 1%. Peptides exhibiting tryptic specificity and possessing up to two missed cleavages were considered legitimately identified. Data were further analyzed through the use of Ingenuity Pathways Analysis (Ingenuity® Systems, www.ingenuity.com).

Electrophoretic and Immunoblot Analysis.

SKOV-3 (ovary cancer cell line) and LNCap (prostate cancer cell line) cells were purchased from American Type Culture Association (ATCC, Manassas, Va.). Cells were cultured in McCoy's 5A medium (SKOV-3 cells) or RPMI 1640 medium (LNCap cells) supplemented with 10% fetal bovine serum and 1× mixture of penicillin G sodium, streptomycin sulfate, and L-glutamine (Invitrogen, Life Technologies, Carlesbad, Calif.). Cells were lysed in 1× Cell Lysis Buffer (Cell Signaling Technology, Inc. Danvers, Mass.) for 20 minutes at 4° C. Cell lysates were centrifuged at 13,000 g for 5 minutes to remove cellular debris. Clarified cell lysates were stored at −80° C. HUVEC (Human Umbilical Vein Endothelial Cells) lysate was purchased from Santa Cruz Biotechnology, Inc. Santa Cruz, Calif. Depleted peripheral blood plasma samples from patient and healthy donor along with cellular lysates were separated on 4-20% Tris-Glycine gradient gels (Invitrogen, Life Technologies, Carlesbad, Calif.) and transferred to Immun-Blot PVDF membranes (Bio-Rad Laboratories, Hercules, Calif.). The membranes were blocked in 3% bovine serum albumin for 2 hours at room temperature. The membrane was then probed overnight at 4° C. with anti-cadherin-5 MAb (BD Biosciences, San Jose, Calif.) followed by peroxidase conjugated goat anti-mouse IgG secondary antibody (Jackson ImmunoResearch Laboratories, Inc. West Grove, Pa.) for 1 hour at room temperature. The antibody reactivity was detected using ECL Western Blotting Detection Reagent (Amersham Biosciences, Piscataway, N.J.).

Example 2

Method of Identifying Tumor Biomarkers Including RCC Biomarkers

This example describes a method of identifying tumor biomarkers using RCC as a model. This example also provides an RCC gene signature that can be used to diagnosis a subject with RCC. One skilled in the art will appreciate that similar methods can be used to identify biomarkers for other cancers, such as breast, lung, colon, or liver cancer.

Tumorous (0.57 grams) and non-tumorous tissue (normal adjacent kidney tissue, 0.56 grams) was obtained from a single patient and freshly frozen in liquid nitrogen along with 0.6 mL of patient's peripheral blood plasma. Since the plasma content of kidney tissue represents up to 22% of its weight the abundant protein depletion was applied to both tissue and plasma specimens. This step significantly contributed to dynamic range reduction and increased overall detection rate of low-abundant proteins. Subsequent tryptic digestion was performed in buffered methanol. The use of organic solvent provided improved solubilization and denaturation, while the absence of detergents and chaotropes assured optimal separation and ionization of peptides that resulted in optimal identification of both, cytosolic and membrane proteins.

A total of 200 µg of tryptic peptides from each specimen was resolved by off-line SCX-LC into 36 peptide fractions.

The use of the ultraviolet (UV) laser-induced fluorescence detector greatly improved sensitivity of SCX separations, allowing minimal peptide overlap resulting in improved dynamic range of subsequent MS analysis. Finally, in-depth analysis of tissue and plasma peptide fractions was carried out using high resolution and high mass accuracy nfRPLC-ESI-LIT-FTICR-MS. To increase the sequencing capacity and amplify the rate of peptide/protein identification in the discovery phase, each peptide fraction was analyzed twice. Following initial data analysis, a final list of protein identifications for each specimen was created by including only unique and protein-specific peptides, eliminating ambiguities caused by inclusion of peptides identifying multiple protein species. The analysis resulted in the identification of 1,281 proteins in the normal-adjacent tumorous tissue, 1,275 proteins in the tumorous tissue and 420 proteins in the peripheral blood plasma.

Proteins specific to tumor tissue were then identified by subtractive proteomic analysis. By using a criteria of two protein specific peptides, authentic tumor-derived proteins were identified in any of the peptide fractions from tumor tissue but not in any of the technical replicates from normal adjacent tissue specimens. Results showed a subset of 209 proteins identified exclusively in normal-adjacent tissue and 202 proteins identified exclusively in tumor tissue (FIG. 2A). It was hypothesized that the majority of 202 proteins identified exclusively in tumor tissue should play a role in RCC biology. It was also hypothesized that any of these 202 proteins identified in peripheral blood plasma, showing higher total peptide count in tumor tissue, should be considered as genuine tumor-derived proteins and potential RCC cancer biomarkers.

Figure 2B:
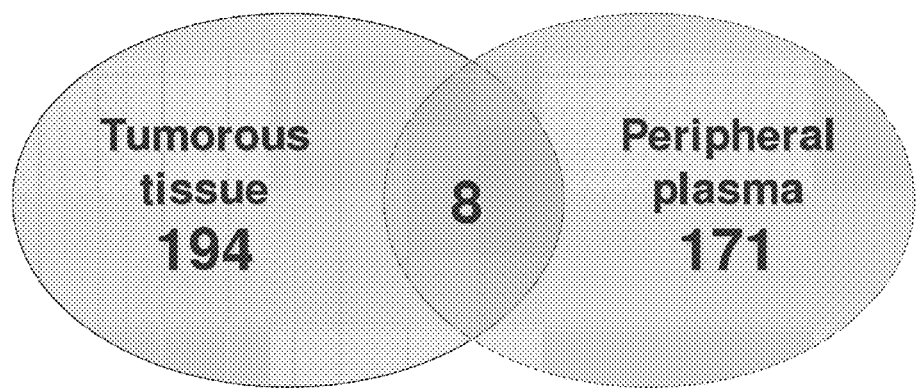

A goal of these studies was to identify tumor-derived proteins in a preoperative plasma specimen. To achieve this objective, the list of 202 proteins identified exclusively in tumor tissue were compared with the list of 171 proteins identified in plasma, using the same subtractive proteomic approach. By applying stringent statistical criteria the reliable tumor-derived proteins were then mapped into the more complex plasma space. Tumor-derived protein identified in plasma should meet the same statistical criteria and display lower spectral count/relative abundance in the plasma specimen. This analysis revealed a total of 8 proteins meeting these criteria (FIG. 2B; Table 1). Ingenuity Pathway Analysis revealed that all of 8 identified proteins were found to be expressed in kidney tissue while three of them were characterized as membrane proteins (Table 1). Overall, these findings identified proteins that are a genuine RCC-derived set, representing a biomarker panel specific to the tumor phenotype of this particular patient Importantly these results show that the identification of these marker proteins was not incidental but a direct outcome of described method.

TABLE 1

Tumor-derived proteins identified by subtractive proteomics in plasma of a patient diagnosed with RCC.

| Protein[1] | Gene[2] | Location[3] | Accession[4] |
|---|---|---|---|
| Cadherin-5 | CDH5 | membrane | P33151 |
| Cadherin-11 | CDH11 | membrane | P55287 |
| Probable ATP-dependent RNA helicase | DDX23 | nucleus | Q9BUQ8 |
| WW and C2 domain containing 1 | WWC1 | cytoplasm | Q8IX03 |
| Chromodomain-helicase-DNA-binding protein 4 | CHD4 | nucleus | Q14839 |
| Nuclear receptor coactivator 6 | NCOA6 | nucleus | Q14686 |
| Pyruvate kinase 2/3 | PKM2 | cytoplasm | P14618 |
| Vascular cell adhesion protein 1 | VCAM1 | membrane | P19320 |

[1]Protein name (UniProtKB/Swiss-Prot),
[2]Gene name (UniProtKB/Swiss-Prot),
[3]Subcellular location (Ingenuity Pathway Analysis),
[4]Accession number (UniProtKB/Swiss-Prot).

Eight peptides identified in tumor tissue and plasma are shown in Table 2.

TABLE 2

Peptides identified by LC-MS/MS in tumor and plasma specimens.

| Protein Identified in Tumor* | Gene* | MH+ | Charge | Xcorr | DelCN | Peptide (SEQ ID NO.) | Acc No* |
|---|---|---|---|---|---|---|---|
| Cadherin-5 precursor | CDH5 | 966.48909 | 2 | 2.8634 | 0.3334 | K.KGDIYNEK.E (1) | P33151 |
| Cadherin-5 precursor | CDH5 | 1085.5374 | 2 | 3.1009 | 0.4432 | R.TSDKGQFFR.V (2) | P33151 |
| Cadherin-5 precursor | CDH5 | 1105.5372 | 1 | 2.7441 | 0.4692 | K.ELDSTGTPTGK.E (3) | P33151 |
| Cadherin-5 precursor | CDH5 | 1105.5372 | 2 | 2.7275 | 0.7069 | K.ELDSTGTPTGK.E (3) | P33151 |
| Cadherin-5 precursor | CDH5 | 1105.5372 | 1 | 2.2155 | 0.5139 | K.ELDSTGTPTGK.E (3) | P33151 |
| Cadherin-5 precursor | CDH5 | 1105.5372 | 2 | 2.7013 | 0.6224 | K.ELDSTGTPTGK.E (3) | P33151 |
| Cadherin-5 precursor | CDH5 | 1085.5374 | 2 | 3.1732 | 0.5031 | R.TSDKGQFFR.V (2) | P33151 |
| Cadherin-5 precursor | CDH5 | 1667.9149 | 3 | 4.4553 | 0.5157 | K.KPLIGTVLAMDPDAAR.H (4) | P33151 |
| Cadherin-5 precursor | CDH5 | 966.48909 | 2 | 3.0493 | 0.2333 | K.KGDIYNEK.E (1) | P33151 |
| Cadherin-5 precursor | CDH5 | 1667.9149 | 2 | 4.188 | 0.6923 | K.KPLIGTVLAMDPDAAR.H (4) | P33151 |
| Cadherin-5 precursor | CDH5 | 1667.9149 | 3 | 4.5346 | 0.671 | K.KPLIGTVLAMDPDAAR.H (4) | P33151 |
| Cadherin-5 precursor | CDH5 | 1667.9149 | 2 | 4.0874 | 0.7237 | K.KPLIGTVLAMDPDAAR.H (4) | P33151 |

TABLE 2-continued

Peptides identified by LC-MS/MS in tumor and plasma specimens.

| Protein Identified in Plasma | Gene | MH+ | Charge | Xcorr | DelCN | Peptide | Acc No |
|---|---|---|---|---|---|---|---|
| Cadherin-5 precursor | CDH5 | 1105.5372 | 2 | 2.9475 | 0.5093 | K.ELDSTGTPTGK.E (3) | P33151 |
| Cadherin-5 precursor | CDH5 | 1667.9149 | 2 | 3.5155 | 0.6865 | K.KPLIGTVLAMDPDAAR.H (4) | P33151 |

| Protein Identified in Tumor | Gene | MH+ | Charge | Xcorr | DelCN | Peptide | Acc No |
|---|---|---|---|---|---|---|---|
| Cadherin-11 precursor | CDH11 | 2165.0662 | 3 | 4.5038 | 0.5838 | R.HTDLDREFTINPEDGFIK.T (5) | P55287 |
| Cadherin-11 precursor | CDH11 | 2165.0662 | 3 | 3.7203 | 0.5971 | R.HTDLDRFFTINPEDGFIK.T (5) | P55287 |
| Cadherin-11 precursor | CDH11 | 1490.771 | 3 | 3.802 | 0.6285 | R.VHAKDPDAANSPIR.Y (6) K.EDIRDNIVSYNDEGGGEED (7) | P55287 |
| Cadherin-11 precursor | CDH11 | 3228.4564 | 3 | 4.8952 | 0.7665 | TQAFDIGTLR.N (8) | P55287 |

| Protein Identified in Plasma | Gene | MH+ | Charge | Xcorr | DelCN | Peptide | Acc No |
|---|---|---|---|---|---|---|---|
| Cadherin-11 precursor | CDH11 | 1490.771 | 3 | 3.885 | 0.4324 | R.VHAKDPDAANSPIR.Y (6) | P55287 |
| Cadherin-11 precursor | CDH11 | 1084.5633 | 2 | 2.8856 | 0.5846 | R.VLDVNDNAPK.F (9) | P55287 |

| Protein Identified in Tumor | Gene | MH+ | Charge | Xcorr | DelCN | Peptide | Acc No |
|---|---|---|---|---|---|---|---|
| Chromodomain-helicase-DNA-binding protein 4 | CHD4 | 1586.7883 | 2 | 2.9277 | 0.2588 | R.AYHLVC*LDPELEK.A (10) | Q14839 |
| Chromodomain-helicase-DNA-binding protein 4 | CHD4 | 1875.9672 | 2 | 3.1726 | 0.5154 | R.LANRAPEPTPQQVAQQQ. (11) | Q14839 |
| Chromodomain-helicase-DNA-binding protein 4 | CHD4 | 1875.9672 | 2 | 4.5646 | 0.5639 | R.LANRAPEPTPQQVAQQQ. (11)- | Q14839 |
| Chromodomain-helicase-DNA-binding protein 4 | CHD4 | 1586.7883 | 2 | 2.7225 | 0.1661 | R.AYHLVC*LDPELEK.A (10) | Q14839 |

| Protein Identified in Plasma | Gene | MH+ | Charge | Xcorr | DelCN | Peptide | Acc No |
|---|---|---|---|---|---|---|---|
| Chromodomain-helicase-DNA-binding protein 4 | CHD4 | 1975.9277 | 2 | 2.8574 | 0.0822 | K.EVM#LQNGETPKDLNDEK.Q (12) | Q14839 |
| Chromodomain-helicase-DNA-binding protein 4 | CHD4 | 1875.9672 | 2 | 2.6594 | 0.5154 | R.LANRAPEPTPQQVAQQQ.(11) | Q14839 |

| Protein Identified in Tumor | Gene | MH+ | Charge | Xcorr | DelCN | Peptide | Acc No |
|---|---|---|---|---|---|---|---|
| Nuclear receptor coactivator 6 | NCOA6 | 1418.7274 | 2 | 3.123 | 0.3984 | R.GFDQQGLNPTTLK.A (13) | Q14686 |
| Nuclear receptor coactivator 6 | NCOA6 | 1418.7274 | 2 | 3.035 | 0.2543 | R.GFDQQGLNPTTLK.A (13) | Q14686 |
| Nuclear receptor coactivator 6 | NCOA6 | 1956.1263 | 2 | 2.7369 | 0.6595 | R.SIVTTLVPSELISAVPTTK.S (14) | Q14686 |
| Nuclear receptor coactivator 6 | NCOA6 | 1575.7748 | 2 | 3.4736 | 0.6709 | R.VLSSTSEEDEPGVVK.F (15) | Q14686 |

| Protein Identified in Plasma | Gene | MH+ | Charge | Xcorr | DelCN | Peptide | Acc No |
|---|---|---|---|---|---|---|---|
| Nuclear receptor coactivator 6 | NCOA6 | 672.42905 | 1 | 2.1036 | 0.0845 | K.LDAILK.N (16) | Q14686 |
| Nuclear receptor coactivator 6 | NCOA6 | 1418.7274 | 2 | 2.7001 | 0.2543 | R.GFDQQGLNPTTLK.A (13) | Q14686 |

TABLE 2-continued

Peptides identified by LC-MS/MS in tumor and plasma specimens.

| Protein Identified in Tumor | Gene | MH+ | Charge | Xcorr | DelCN | Peptide | Acc No |
|---|---|---|---|---|---|---|---|
| Probable ATP-dependent RNA helicase | DDX23 | 1229.6372 | 3 | 3.8524 | 0.3521 | K.KAEEEAEAKPK.F (17) | Q9BUQ8 |
| Probable ATP-dependent RNA helicase | DDX23 | 1229.6372 | 3 | 3.9042 | 0.3663 | K.KAEEEAEAKPK.F (17) | Q9BUQ8 |
| Probable ATP-dependent RNA helicase | DDX23 | 1921.8305 | 3 | 5.0899 | 0.5256 | R.MERETNGNEDEEGRQK.I (18) | Q9BUQ8 |
| Probable ATP-dependent RNA helicase | DDX23 | 1921.8305 | 3 | 4.6987 | 0.4908 | R.MERETNGNEDEEGRQK.I (18) | Q9BUQ8 |

| Protein Identified in Plasma | Gene | MH+ | Charge | Xcorr | DelCN | Peptide | Acc No |
|---|---|---|---|---|---|---|---|
| Probable ATP-dependent RNA helicase | DDX23 | 1004.4895 | 2 | 2.8763 | 0.4104 | K.KAEEEAEAK.P (19) | Q9BUQ8 |
| Probable ATP-dependent RNA helicase | DDX23 | 1921.8305 | 3 | 3.6812 | 0.4908 | R.MERETNGNEDEEGRQK.I (18) | Q9BUQ8 |

| Protein Identified in Tumor | Gene | MH+ | Charge | Xcorr | DelCN | Peptide | Acc No |
|---|---|---|---|---|---|---|---|
| Pyruvate kinase isozymes M1/M2 | PKM2 | 1302.6835 | 2 | 2.8432 | 0.3985 | R.NTGIICTIGPASR.S (20) | P14618 |
| Pyruvate kinase isozymes M1/M2 | PKM2 | 1462.8152 | 2 | 3.6427 | 0.7347 | K.IYVDDGLISLQVK.Q (21) | P14618 |
| Pyruvate kinase isozymes M1/M2 | PKM2 | 1197.6474 | 2 | 3.6093 | 0.5596 | R.LDIDSPPITAR.N (22) | P14618 |
| Pyruvate kinase isozymes M1/M2 | PKM2 | 1197.6474 | 2 | 3.95 | 0.5973 | R.LDIDSPPITAR.N (22) | P14618 |
| Pyruvate kinase isozymes M1/M2 | PKM2 | 1197.6474 | 2 | 3.1929 | 0.5873 | R.LDIDSPPITAR.N (22) | P14618 |
| Pyruvate kinase isozymes M1/M2 | PKM2 | 1197.6474 | 2 | 3.3787 | 0.4949 | R.LDIDSPPITAR.N (22) | P14618 |
| Pyruvate kinase isozymes M1/M2 | PKM2 | 1197.6474 | 2 | 3.0381 | 0.5901 | R.LDIDSPPITAR.N (22) | P14618 |

| Protein Identified in Plasma | Gene | MH+ | Charge | Xcorr | DelCN | Peptide | Acc No |
|---|---|---|---|---|---|---|---|
| Pyruvate kinase isozymes M1/M2 | PKM2 | 1197.6474 | 2 | 3.3278 | 0.4355 | R.LDIDSPPITAR.N (22) | P14618 |
| Pyruvate kinase isozymes M1/M2 | PKM2 | 1462.8152 | 2 | 2.7512 | 0.7347 | K.IYVDDGLISLQVK.Q (21) | P14618 |

| Protein Identified in Tumor | Gene | MH+ | Charge | Xcorr | DelCN | Peptide | Acc No |
|---|---|---|---|---|---|---|---|
| Vascular cell adhesion protein 1 precursor | VCAM1 | 1159.6317 | 2 | 2.9966 | 0.4313 | K.NTVISVNPSTK.L (23) | P19320 |
| Vascular cell adhesion protein 1 precursor | VCAM1 | 1159.6317 | 1 | 2.5145 | 0.4686 | K.NTVISVNPSTK.L (23) | P19320 |
| Vascular cell adhesion protein 1 precursor | VCAM1 | 1476.7805 | 2 | 3.3776 | 0.5713 | R.QSTQTLYVNVAPR.D (24) | P19320 |

TABLE 2-continued

Peptides identified by LC-MS/MS in tumor and plasma specimens.

| Protein Identified in Tumor | Gene | MH+ | Charge | Xcorr | DelCN | Peptide | Acc No |
|---|---|---|---|---|---|---|---|
| Vascular cell adhesion protein 1 precursor | VCAM1 | 1159.6317 | 1 | 2.6741 | 0.47 | K.NTVISVNPSTK.L (23) | P19320 |
| Vascular cell adhesion protein 1 precursor | VCAM1 | 2267.2282 | 3 | 4.6982 | 0.7343 | K.EVELIVQEKPFTVEISPGPR.I (25) | P19320 |
| Vascular cell adhesion protein 1 precursor | VCAM1 | 1337.6332 | 2 | 3.536 | 0.5115 | K.SQEFLEDADRK.S (26) | P19320 |
| Vascular cell adhesion protein 1 precursor | VCAM1 | 1647.884 | 2 | 4.6728 | 0.6674 | K.SLEVTFTPVIEDIGK.V (27) | P19320 |
| Vascular cell adhesion protein 1 precursor | VCAM1 | 1647.884 | 2 | 4.7374 | 0.6658 | K.SLEVTFTPVIEDIGK.V (27) | P19320 |
| Vascular cell adhesion protein 1 precursor | VCAM1 | 1476.7805 | 2 | 2.9011 | 0.5289 | R.QSTQTLYVNVAPR.D (24) | P19320 |

| Protein Identified in Plasma | Gene | MH+ | Charge | Xcorr | DelCN | Peptide | Acc No |
|---|---|---|---|---|---|---|---|
| Vascular cell adhesion protein 1 precursor | VCAM1 | 1373.6406 | 2 | 2.9889 | 0.656 | K.LHIDDMEFEPK.Q (28) | P19320 |
| Vascular cell adhesion protein 1 precursor | VCAM1 | 1373.6406 | 2 | 2.7529 | 0.5545 | K.LHIDDMEFEPK.Q (28) | P19320 |
| Vascular cell adhesion protein 1 precursor | VCAM1 | 1647.884 | 2 | 3.0018 | 0.5692 | K.SLEVTFTPVIEDIGK.V (27) | P19320 |
| Vascular cell adhesion protein 1 precursor | VCAM1 | 1476.7805 | 2 | 3.1744 | 0.5882 | R.QSTQTLYVNVAPR.D (24) | P19320 |

| Protein Identified in Tumor | Gene | MH+ | Charge | Xcorr | DelCN | Peptide | Acc No |
|---|---|---|---|---|---|---|---|
| WW and C2 domain containing 1 | WWC1 | 1026.4586 | 2 | 2.9838 | 0.5614 | R.SDSDSSTLSK.K (29) | Q8IX03 |
| WW and C2 domain containing 1 | WWC1 | 1026.4586 | 2 | 2.8358 | 0.5619 | R.SDSDSSTLSK.K (29) | Q8IX03 |
| WW and C2 domain containing 1 | WWC1 | 1026.4586 | 2 | 3.1708 | 0.5316 | R.SDSDSSTLSK.K (29) | Q8IX03 |
| WW and C2 domain containing 1 | WWC1 | 1262.6488 | 2 | 3.2256 | 0.5435 | R.RGDSQPYQALK.Y (30) | Q8IX03 |

| Protein Identified in Plasma | Gene | MH+ | Charge | Xcorr | DelCN | Peptide | Acc No |
|---|---|---|---|---|---|---|---|
| WW and C2 domain containing 1 | WWC1 | 1218.6875 | 1 | 2.3264 | 0.0861 | K.AIKKAITC*GEK.E (31) | Q8IX03 |
| WW and C2 domain containing 1 | WWC1 | 1026.4586 | 2 | 2.5832 | 0.5619 | R.SDSDSSTLSK.K (29) | Q8IX03 |

*Gene or Accession number according to the UniProtKB/Swiss-Prot database as of Mar. 20, 2009

Figure 3A:
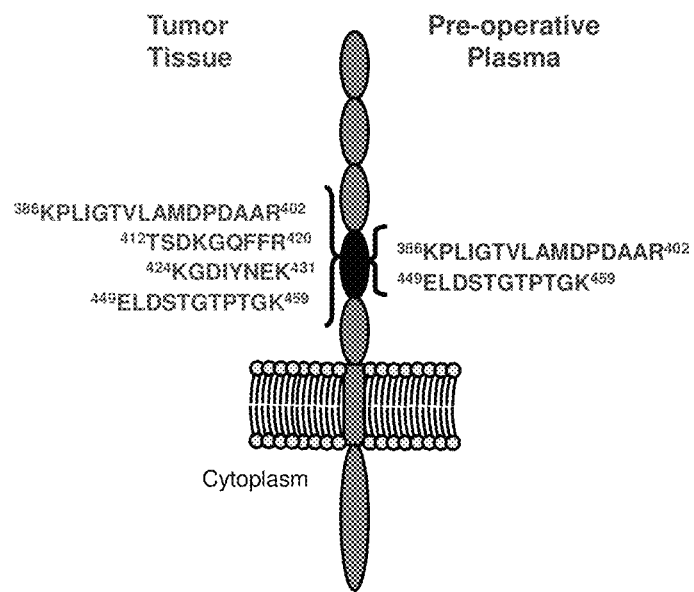
FIG. 3A is a schematic representation of the secondary structure of cadherin-5 depicting the location of identified peptides. Peptides with amino acid sequences provided by SEQ ID NOs: 4, 2, 1 and 3 respectively (on the left) were identified in tumor while peptides with amino acid sequences provided by SEQ ID NOs: 4 and 3, respectively (on the right) were identified in plasma. All identified peptides reside in extracellular domain of this integral plasma membrane protein.

Cadherin-5 peptides with amino acid sequences provided by SEQ ID NOs: 1-4 were identified in tumor while peptides with amino acid sequences provided by SEQ ID NOs:3 and 4 were identified in plasma (FIG. 3A). All identified peptides resided in the extracellular domain of this integral plasma membrane protein.

Figure 3B:
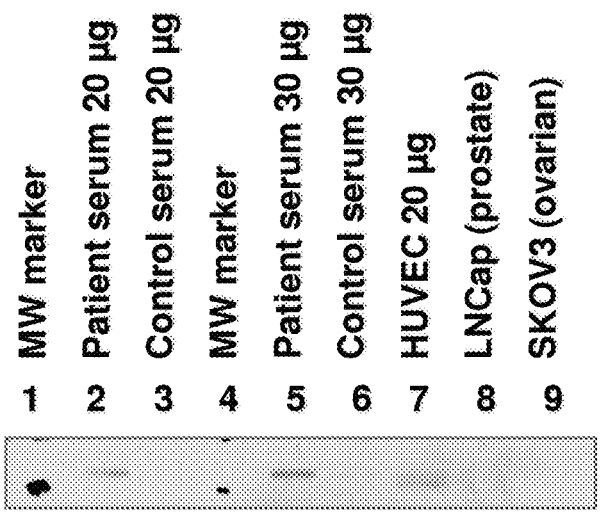
FIG. 3B is a digital image of a Western blot analysis of cadherin-5. A total of 20 μg of depleted plasma protein from the patient (lane 2) and a total of 20 μg depleted plasma protein from a healthy donor (lane 3) along with 30 μg of depleted plasma protein from the same patient (lane 5) and 30 μg depleted plasma protein from a healthy donor (lane 6) were separated on 4-20% Tris-Glycine gradient gels. Also, a total of 20 μg of cellular lysates: HUVEC (lane 7), LNCap (lane 8) and SKOV3 (lane 9) were separated using the same 4-20% Tris-Glycine gradient gels and transferred to Immun-Blot PVDF membranes. The membranes were blocked by 3% bovine serum albumin and then probed overnight at 4° C. with anti-cadherin-5 MAb followed by peroxidase conjugated goat anti-mouse IgG secondary antibody. The analysis confirmed the presence of cadherin-5 in plasma of the patient diagnosed with RCC (lanes 2 and 5) while the plasma of healthy donor (lanes 3 and 6) showed negative results for cadherin-5 as well as immuno-blots of prostate cancer cell (lane 8) and ovary cancer cell lysates (lane 9), respectively. The Western blot analysis of the positive control, HUVEC lysate (lane 7), confirmed the presence of cadherin-5.
Figure 4A:
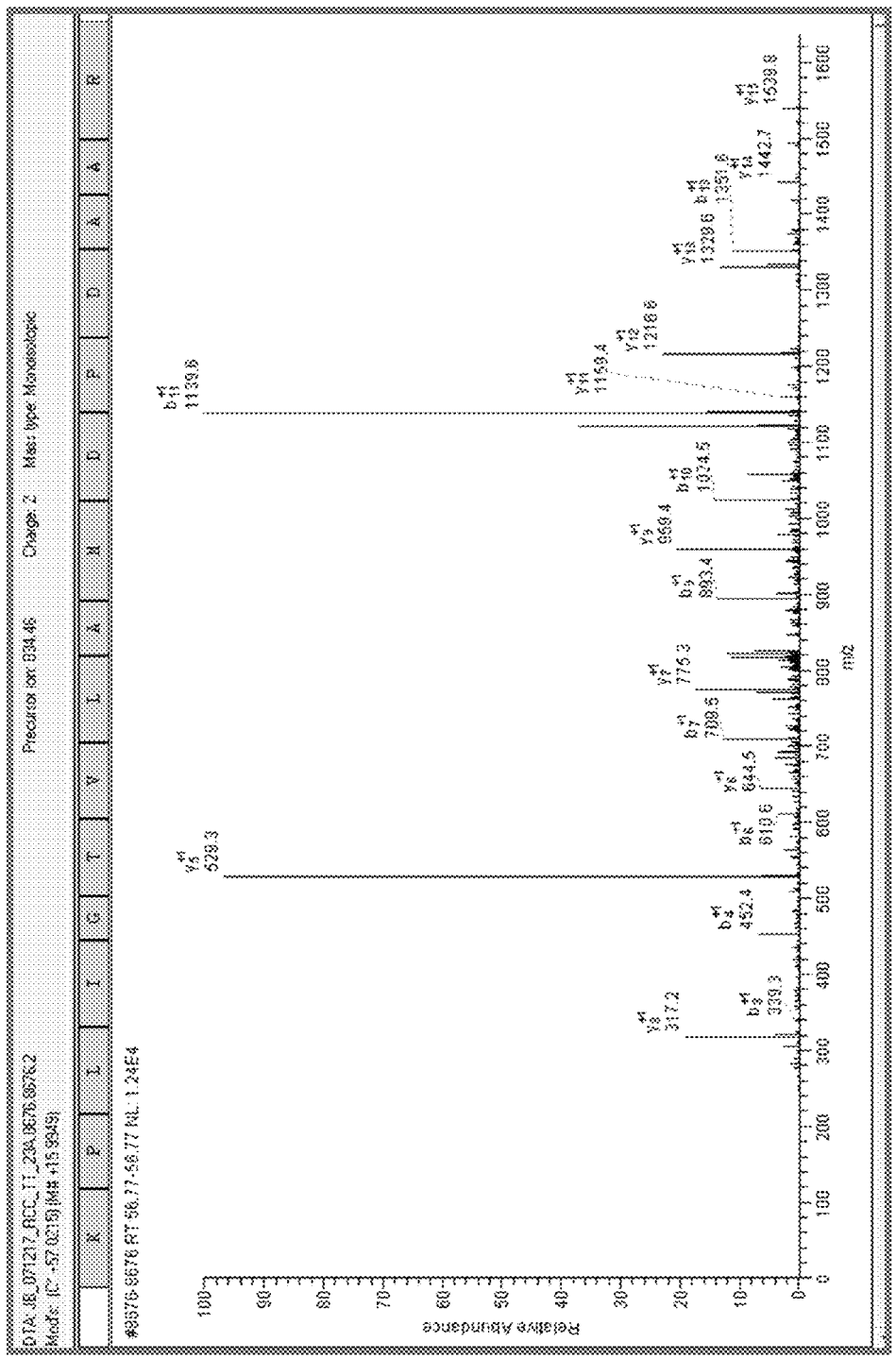
FIGS. 4A and 4B are MS/MS spectra of the KPLIGTVLAMDPDAAR peptide (SEQ ID NO: 4) identifying cadherin-5 in tumor (FIG. 4A) and peripheral plasma (FIG. 4B).
Figure 4B:
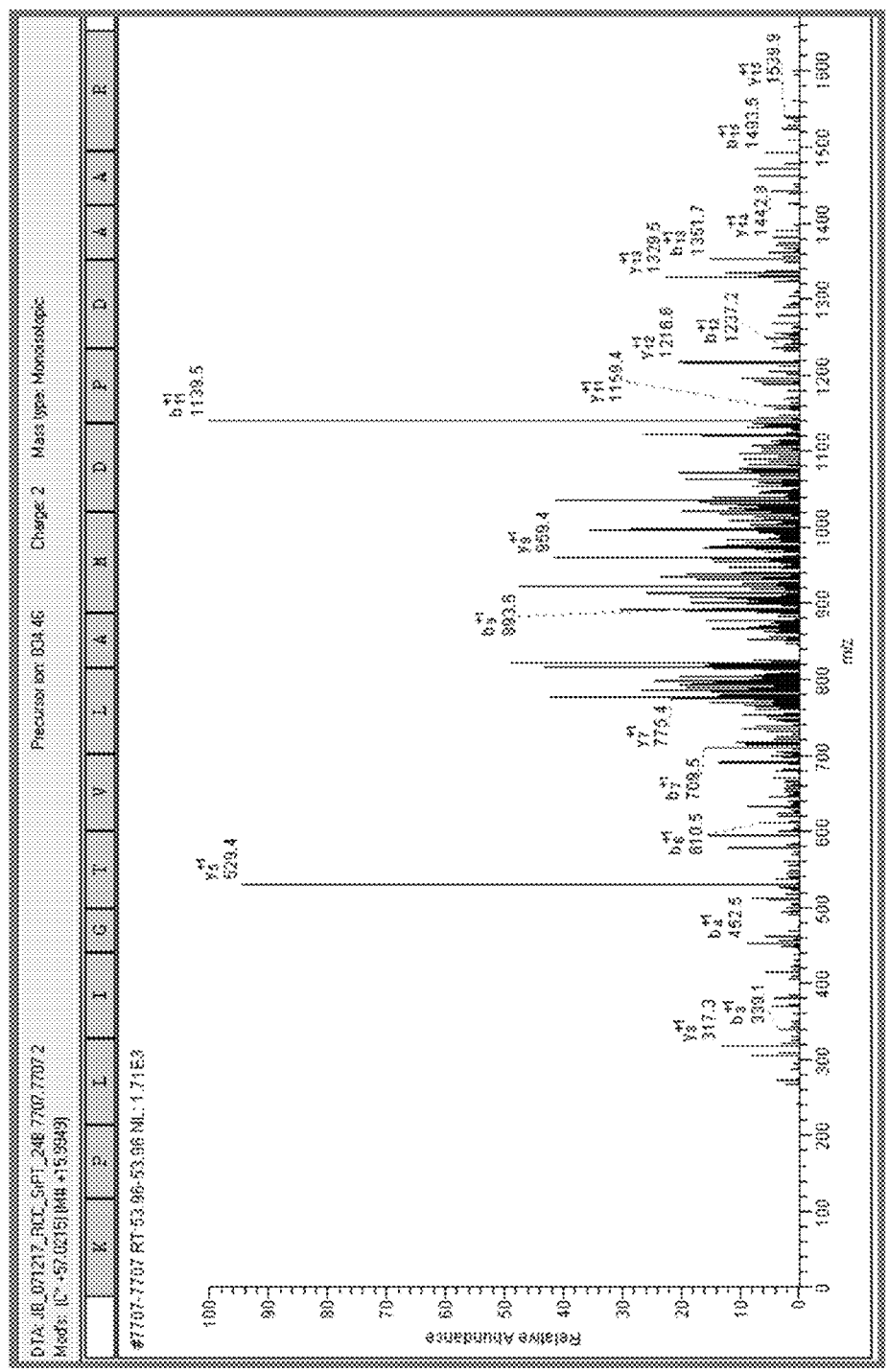
Figure 5:
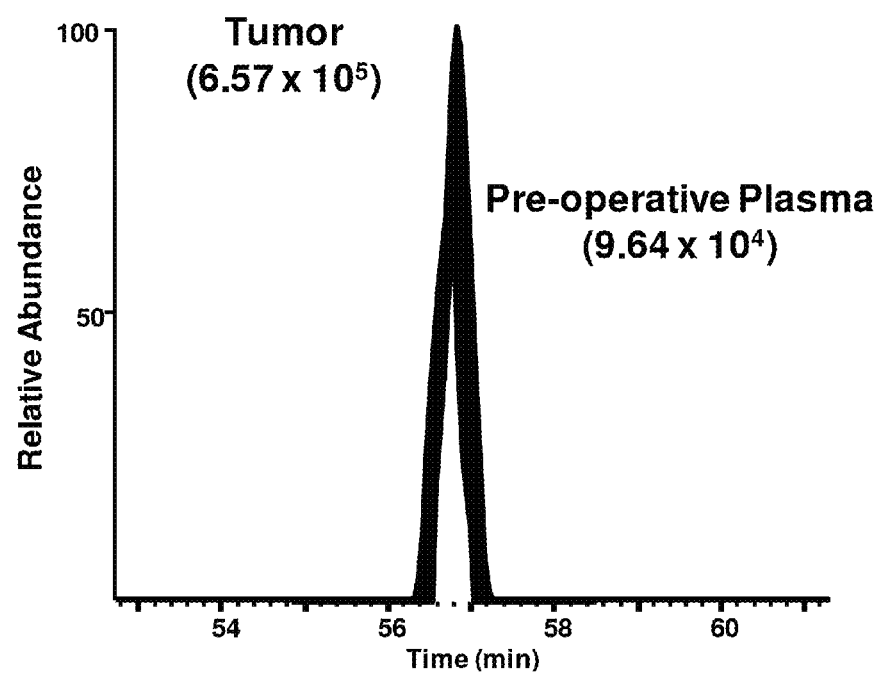
FIG. 5 provides extracted ion chromatograms of the KPLIGTVLAMDPDAAR (SEQ ID NO: 4) peptide identifying cadherin-5 in tumor (black) and peripheral plasma (white) indicating higher concentration level of this peptide/protein in tumor.

For cross validation purposes Western blot was employed. The Western blot analysis confirmed the presence of CDH5 in the plasma of the RCC patient while the presence of cadherin-5 was not detectable in the plasma of a matched healthy donor (FIG. 3B). The same analysis confirmed the presence of CDH5 in HUVEC lysate (positive control) and revealed its absence in ovarian (SKOV-3) and prostate cancer (LNCap) cell lysates (FIG. 3B). The presence of cadherin-5 in tumor and peripheral plasma was confirmed by mass spectrometry studies (See FIGS. 4A and 4B, respectively). Extracted ion chromatograms indicated higher concentration levels of cadherin-5 peptide KPLIGTVLAMDPDAAR (SEQ ID NO: 4) in tumor (black) than peripheral plasma (white) indicating this peptide/protein in tumor. These findings suggest an active role of CDH5 in the RCC phenotype/biology of the patient from whom these clinical specimens were obtained. These findings also suggest CDH5 as a potential anti-angiogenic target.

These results demonstrate that tumor-derived proteins are released into the peripheral blood of this patient diagnosed with RCC, at the levels detectable by high resolution MS. Biomarkers identified from a single patient can be cross-validated using suitable immunoassays and used for profiling of larger patient cohorts. This approach may be amenable to profiling of other solid tumors and may serve as a foundation for a new type of onco-theurapeutic strategy based on a detailed proteomic profile of multiple salient tissue specimens from an individual patient with a newly diagnosed cancer. Such analyses may yield protein molecules germane to the specific cancer in question. These results may then serve as key therapeutic targets thus allowing customized care based on particular molecular aspects of the patient's tumor. Notably, this described strategy offers a reversal of current paradigm where physicians make categorical treatment assignments based on population averages, rather than individual profiles.

Example 3

Diagnosing RCC

This example describes methods that can be used to diagnose a subject with RCC.

According to the teachings herein, whether a subject has RCC can be determined by detecting differential expression of at least two RCC biomarkers in a sample obtained from the subject believed to have RCC or at risk of developing RCC. In an example, a peripheral biological sample, such as serum, is obtained from the subject who is believed to have RCC or at risk of developing RCC. The polypeptide levels of two or more of (such as all of) CDH5, CDH11, DDX23, WWC1, CHD4, NCOA6, PKM2, and VCAM1 in the biological sample is then evaluated using a protein array that includes different capture agents, most frequently monoclonal antibodies, each of which is capable of binding to one or more of the disclosed RCC biomarkers and controls, such as positive and negative controls. The amount of RCC biomarker protein measured in the biological sample is then compared to a reference value reflective of the value of protein present in a non-tumor tissue or in tissue from cancer-free subjects. A significant increase, including at least a 2-fold increase in expression, in one or more of the RCC biomarker proteins, indicates that the subject has RCC.

Example 4

Treatment of RCC

This example describes methods that can be used to treat RCC.

Based upon the teaching disclosed herein, RCC can be reduced or inhibited by administering a therapeutically effective amount of a composition, wherein the composition includes one or more agents that decrease the activity or expression of one or more RCC biomarkers provided in Table 1 that are up-regulated in RCC, thereby treating RCC in the subject.

In an example, a subject who has been diagnosed with RCC is identified by any of the methods disclosed herein. Following subject selection, a therapeutic effective dose of the composition including one or more therapeutic agent is administered to the subject. For example, a therapeutically effective dose of a therapeutic agent to one or more of the disclosed RCC biomarkers is administered to the subject to inhibit RCC. In an example, the agent is a siRNA. In a further example, the agent is an antibody. The amount of the composition administered to prevent, reduce, inhibit, and/or treat RCC or a condition associated with it depends on the subject being treated, the severity of the disorder, and the manner of administration of the therapeutic composition. Ideally, a therapeutically effective amount of an agent is the amount sufficient to prevent, reduce, and/or inhibit, and/or treat the condition (e.g., RCC) in a subject without causing a substantial cytotoxic effect in the subject.

In one specific example, siRNAs are administered at according to the teachings of Soutschek et al. (*Nature* Vol. 432: 173-178, 2004) or Karpilow et al. (*Pharma Genomics* 32-40, 2004) both of which are herein incorporated by reference in their entireties. In one example, siRNAs are incorporated into neutral liposomes, such as DOPC, and injected intraperitoneal or intravenously. For example, a siRNA is administered at 150 µg/kg twice weekly for 2 to 3 weeks.

In another specific example, naked antibodies are administered at 5 mg per kg every two weeks or 10 mg per kg every two weeks depending upon the RCC. In an example, the antibodies are administered continuously. In another example, antibodies or antibody fragments conjugated to cytotoxic agents (immunotoxins) are administered at 50 µg per kg given twice a week for 2 to 3 weeks.

In other examples, the subject is administered the therapeutic composition daily for a period of at least 30 days, such as at least 2 months, at least 4 months, at least 6 months, at least 12 months, at least 24 months, or at least 36 months.

Subjects will monitored by methods known to those skilled in the art to determine tumor responsiveness to the siRNA or antibody treatment. The subject will be monitored by non invasive techniques such as CT or MRI imaging to assess tumor response. It is contemplated that additional agents can be administered, such as antineoplastic agents in combination with or following treatment with the siRNA or antibodies.

While this disclosure has been described with an emphasis upon particular embodiments, it will be obvious to those of ordinary skill in the art that variations of the particular embodiments may be used, and it is intended that the disclosure may be practiced otherwise than as specifically described herein. Features, characteristics, compounds, or examples described in conjunction with a particular aspect, embodiment, or example of the invention are to be understood

We claim:

1. A method of identifying a renal tumor biomarker, comprising:
obtaining a peripheral biological fluid sample from a subject with a renal tumor;
obtaining a renal tumor tissue sample and an adjacent non-tumor tissue sample from the subject with the renal tumor;
extracting proteins from the peripheral biological fluid sample, renal tumor tissue sample and the adjacent non-tumor tissue sample generating a peripheral biological fluid sample protein extract, a renal tumor tissue sample protein extract and an adjacent non-tumor tissue sample protein extract;
depleting proteins from the peripheral biological fluid sample protein extract, the renal tumor tissue sample protein extract and the adjacent non-tumor tissue sample protein extract generating a depleted biological fluid protein sample, a depleted renal tumor tissue protein sample and a depleted adjacent non-tumor tissue protein sample;
digesting the depleted biological fluid protein sample, the depleted renal tumor tissue protein sample and the depleted adjacent non-tumor tissue protein sample generating a digested biological fluid protein sample, a digested depleted renal tumor tissue protein sample and a digested adjacent non-tumor tissue protein sample;
fractionating the digested biological fluid protein sample, the digested depleted renal tumor tissue protein sample and the digested adjacent non-tumor tissue protein sample generating a fractionated biological fluid protein sample, a fractionated depleted renal tumor tissue protein sample and a fractionated adjacent non-tumor tissue protein sample;
detecting a protein expression profile in the fractioned peripheral biological fluid protein sample, the fractioned renal tumor tissue protein sample and the fractionated adjacent non-tumor tissue protein sample by performing high mass accuracy nano-flow reversed phase liquid chromatography-electrospray ionization-linear ion trap-Fourier transform ion cyclotron resonance-mass spectrometry (nfRPLC-ESI-LIT-FTICR-MS) mass spectrometry generating a peripheral biological fluid mass spectra, a renal tumor tissue mass spectra and an adjacent non-tumor tissue mass spectra; and by a computer, analyzing the peripheral biological fluid mass spectra, the renal tumor tissue mass spectra and the adjacent non-tumor tissue mass spectra, generating a peripheral biological fluid protein profile, a renal tumor tissue protein profile and an adjacent non-tumor tissue protein profile;
identifying a renal tumor marker by performing subtractive proteomics comprising identifying a renal tumor tissue specific subset of proteins by comparing the renal tumor tissue protein profile to the adjacent non-tumor tissue protein profile; and comparing the renal tumor tissue specific subset of proteins with proteins within the peripheral biological fluid protein profile, wherein a renal tumor marker is a protein detected in both the renal tumor tissue specific subset of proteins and the peripheral biological fluid profile.

2. The method of claim 1, further comprising developing a consensus protein profile for diagnosing the tumor.

3. The method of claim 1, wherein the peripheral biological fluid sample comprises serum or plasma.

4. The method of claim 1, wherein the peripheral biological fluid sample is obtained prior to surgery.

5. The method of claim 1, wherein analyzing the peripheral biological fluid mass spectra, the renal tumor tissue mass spectra and the adjacent non-tumor tissue mass spectra comprises analyzing the peripheral biological fluid mass spectra, the renal tumor tissue mass spectra and the adjacent non-tumor tissue mass spectra to allow a maximum estimated peptide false discovery rate (FDR) of 1%.

6. The method of claim 1, wherein digesting the depleted biological fluid protein sample, the depleted renal tumor tissue protein sample and the depleted adjacent non-tumor tissue protein sample comprises contacting the depleted biological fluid protein sample, the depleted renal tumor tissue protein sample and the depleted adjacent non-tumor tissue protein sample with trypsin buffered with methanol.

7. The method of claim 6, wherein the digestion is performed in the absence of detergents and chaotropes.

8. A method of identifying a tumor biomarker, comprising:
obtaining a peripheral biological fluid sample from a subject with a tumor;
obtaining a tumor tissue sample and an adjacent non-tumor tissue sample from the subject with the tumor;
extracting proteins from the peripheral biological fluid sample, the tumor tissue sample and the adjacent non-tumor tissue sample generating a peripheral biological fluid sample protein extract, a tumor tissue sample protein extract and an adjacent non-tumor tissue sample protein extract;
depleting proteins from the peripheral biological fluid sample protein extract, the tumor tissue sample protein extract and the adjacent non-tumor tissue sample protein extract generating a depleted biological fluid protein sample, a depleted tumor tissue protein sample and a depleted adjacent non-tumor tissue protein sample;
digesting the depleted biological fluid protein sample, the depleted tumor tissue protein sample and the depleted adjacent non-tumor tissue protein sample generating a digested biological fluid protein sample, a digested depleted tumor tissue protein sample and a digested adjacent non-tumor tissue protein sample; fractionating the digested biological fluid protein sample, the digested depleted tumor tissue protein sample and the digested adjacent non-tumor tissue protein sample generating a fractionated biological fluid protein sample, a fractionated depleted tumor tissue protein sample and a fractionated adjacent non-tumor tissue protein sample;
detecting a protein expression profile in the fractioned peripheral biological fluid protein sample, the fractioned tumor tissue protein sample and the fractionated adjacent non-tumor tissue protein sample by performing high mass accuracy nano-flow reversed phase liquid chromatography-electrospray ionization-linear ion trap-Fourier transform ion cyclotron resonance-mass spectrometry (nfRPLC-ESI-LIT-FTICR-MS) mass spectrometry generating a peripheral biological fluid mass spectra, a renal tumor tissue mass spectra and an adjacent non-tumor tissue mass spectra; and by a computer, analyzing the peripheral biological fluid mass spectra, the tumor tissue mass spectra and the adjacent non-tumor tissue mass spectra, generating a peripheral biological fluid protein profile, a tumor tissue protein profile and an adjacent non-tumor tissue protein profile;
identifying a tumor marker by performing subtractive proteomics comprising identifying a tumor tissue specific subset of proteins by comparing the tumor tissue protein profile to the adjacent non-tumor tissue protein profile; and comparing the tumor tissue specific subset of proteins with proteins within the peripheral biological fluid protein profile, wherein a tumor marker is a protein detected in both the tumor tissue specific subset of proteins and the peripheral biological fluid profile.

9. The method of claim 8, wherein analyzing the peripheral biological fluid mass spectra, the tumor tissue mass spectra and the adjacent non-tumor tissue mass spectra comprises analyzing the peripheral biological fluid mass spectra, the tumor tissue mass spectra and the adjacent non-tumor mass tissue spectra to allow a maximum estimated peptide false discovery rate (FDR) of 1%.

10. The method of claim 9, wherein digesting the depleted biological fluid protein sample, the depleted tumor tissue protein sample and the depleted adjacent non-tumor tissue protein sample comprises contacting the depleted biological fluid protein sample, the depleted tumor tissue protein sample and the depleted adjacent non-tumor tissue protein sample with trypsin buffered with methanol.

11. The method of claim 10, wherein the digestion is performed in the absence of detergents and chaotropes.

\* \* \* \* \*

SEQUENCE LISTING

```
<160> NUMBER OF SEQ ID NOS: 32

<210> SEQ ID NO 1
<211> LENGTH: 10
<212> TYPE: PRT
<213> ORGANISM: Homo sapiens

<400> SEQUENCE: 1

Lys Lys Gly Asp Ile Tyr Asn Glu Lys Glu
1               5                   10

<210> SEQ ID NO 2
<211> LENGTH: 11
<212> TYPE: PRT
<213> ORGANISM: Homo sapiens

<400> SEQUENCE: 2

Arg Thr Ser Asp Lys Gly Gln Phe Phe Arg Val
1               5                   10

<210> SEQ ID NO 3
<211> LENGTH: 13
<212> TYPE: PRT
<213> ORGANISM: Homo sapiens

<400> SEQUENCE: 3

Lys Glu Leu Asp Ser Thr Gly Thr Pro Thr Gly Lys Glu
1               5                   10

<210> SEQ ID NO 4
<211> LENGTH: 18
<212> TYPE: PRT
<213> ORGANISM: Homo sapiens

<400> SEQUENCE: 4

Lys Lys Pro Leu Ile Gly Thr Val Leu Ala Met Asp Pro Asp Ala Ala
1               5                   10                  15

Arg His

<210> SEQ ID NO 5
<211> LENGTH: 20
<212> TYPE: PRT
<213> ORGANISM: Homo sapiens

<400> SEQUENCE: 5

Arg His Thr Asp Leu Asp Arg Phe Phe Thr Ile Asn Pro Glu Asp Gly
1               5                   10                  15

Phe Ile Lys Thr
            20

<210> SEQ ID NO 6
<211> LENGTH: 16
<212> TYPE: PRT
<213> ORGANISM: Homo sapiens

<400> SEQUENCE: 6

Arg Val His Ala Lys Asp Pro Asp Ala Ala Asn Ser Pro Ile Arg Tyr
1               5                   10                  15
```

```
<210> SEQ ID NO 7
<211> LENGTH: 20
<212> TYPE: PRT
<213> ORGANISM: Homo sapiens

<400> SEQUENCE: 7

Lys Glu Asp Ile Arg Asp Asn Ile Val Ser Tyr Asn Asp Glu Gly Gly
1               5                   10                  15

Gly Glu Glu Asp
            20

<210> SEQ ID NO 8
<211> LENGTH: 11
<212> TYPE: PRT
<213> ORGANISM: Homo sapiens

<400> SEQUENCE: 8

Thr Gln Ala Phe Asp Ile Gly Thr Leu Arg Asn
1               5                   10

<210> SEQ ID NO 9
<211> LENGTH: 12
<212> TYPE: PRT
<213> ORGANISM: Homo sapiens

<400> SEQUENCE: 9

Arg Val Leu Asp Val Asn Asp Asn Ala Pro Lys Phe
1               5                   10

<210> SEQ ID NO 10
<211> LENGTH: 15
<212> TYPE: PRT
<213> ORGANISM: Homo sapiens

<400> SEQUENCE: 10

Arg Ala Tyr His Leu Val Cys Leu Asp Pro Glu Leu Glu Lys Ala
1               5                   10                  15

<210> SEQ ID NO 11
<211> LENGTH: 18
<212> TYPE: PRT
<213> ORGANISM: Homo sapiens

<400> SEQUENCE: 11

Arg Leu Ala Asn Arg Ala Pro Glu Pro Thr Pro Gln Gln Val Ala Gln
1               5                   10                  15

Gln Gln

<210> SEQ ID NO 12
<211> LENGTH: 19
<212> TYPE: PRT
<213> ORGANISM: Homo sapiens

<400> SEQUENCE: 12

Lys Glu Val Met Leu Gln Asn Gly Glu Thr Pro Lys Asp Leu Asn Asp
1               5                   10                  15

Glu Lys Gln

<210> SEQ ID NO 13
<211> LENGTH: 15
<212> TYPE: PRT
<213> ORGANISM: Homo sapiens

<400> SEQUENCE: 13
```

```
Arg Gly Phe Asp Gln Gln Gly Leu Asn Pro Thr Thr Leu Lys Ala
1               5                   10                  15
```

<210> SEQ ID NO 14
<211> LENGTH: 21
<212> TYPE: PRT
<213> ORGANISM: Homo sapiens

<400> SEQUENCE: 14

```
Arg Ser Ile Val Thr Thr Leu Val Pro Ser Glu Leu Ile Ser Ala Val
1               5                   10                  15

Pro Thr Thr Lys Ser
            20
```

<210> SEQ ID NO 15
<211> LENGTH: 17
<212> TYPE: PRT
<213> ORGANISM: Homo sapiens

<400> SEQUENCE: 15

```
Arg Val Leu Ser Ser Thr Ser Glu Glu Asp Glu Pro Gly Val Val Lys
1               5                   10                  15

Phe
```

<210> SEQ ID NO 16
<211> LENGTH: 8
<212> TYPE: PRT
<213> ORGANISM: Homo sapiens

<400> SEQUENCE: 16

```
Lys Leu Asp Ala Ile Leu Lys Asn
1               5
```

<210> SEQ ID NO 17
<211> LENGTH: 13
<212> TYPE: PRT
<213> ORGANISM: Homo sapiens

<400> SEQUENCE: 17

```
Lys Lys Ala Glu Glu Glu Ala Glu Ala Lys Pro Lys Phe
1               5                   10
```

<210> SEQ ID NO 18
<211> LENGTH: 18
<212> TYPE: PRT
<213> ORGANISM: Homo sapiens

<400> SEQUENCE: 18

```
Arg Met Glu Arg Glu Thr Asn Gly Asn Glu Asp Glu Glu Gly Arg Gln
1               5                   10                  15

Lys Ile
```

<210> SEQ ID NO 19
<211> LENGTH: 11
<212> TYPE: PRT
<213> ORGANISM: Homo sapiens

<400> SEQUENCE: 19

```
Lys Lys Ala Glu Glu Glu Ala Glu Ala Lys Pro
1               5                   10
```

<210> SEQ ID NO 20

```
<211> LENGTH: 15
<212> TYPE: PRT
<213> ORGANISM: Homo sapiens

<400> SEQUENCE: 20

Arg Asn Thr Gly Ile Ile Cys Thr Ile Gly Pro Ala Ser Arg Ser
1               5                   10                  15

<210> SEQ ID NO 21
<211> LENGTH: 15
<212> TYPE: PRT
<213> ORGANISM: Homo sapiens

<400> SEQUENCE: 21

Lys Ile Tyr Val Asp Asp Gly Leu Ile Ser Leu Gln Val Lys Gln
1               5                   10                  15

<210> SEQ ID NO 22
<211> LENGTH: 13
<212> TYPE: PRT
<213> ORGANISM: Homo sapiens

<400> SEQUENCE: 22

Arg Leu Asp Ile Asp Ser Pro Pro Ile Thr Ala Arg Asn
1               5                   10

<210> SEQ ID NO 23
<211> LENGTH: 13
<212> TYPE: PRT
<213> ORGANISM: Homo sapiens

<400> SEQUENCE: 23

Lys Asn Thr Val Ile Ser Val Asn Pro Ser Thr Lys Leu
1               5                   10

<210> SEQ ID NO 24
<211> LENGTH: 15
<212> TYPE: PRT
<213> ORGANISM: Homo sapiens

<400> SEQUENCE: 24

Arg Gln Ser Thr Gln Thr Leu Tyr Val Asn Val Ala Pro Arg Asp
1               5                   10                  15

<210> SEQ ID NO 25
<211> LENGTH: 22
<212> TYPE: PRT
<213> ORGANISM: Homo sapiens

<400> SEQUENCE: 25

Lys Glu Val Glu Leu Ile Val Gln Glu Lys Pro Phe Thr Val Glu Ile
1               5                   10                  15

Ser Pro Gly Pro Arg Ile
            20

<210> SEQ ID NO 26
<211> LENGTH: 13
<212> TYPE: PRT
<213> ORGANISM: Homo sapiens

<400> SEQUENCE: 26

Lys Ser Gln Glu Phe Leu Glu Asp Ala Asp Arg Lys Ser
1               5                   10
```

```
<210> SEQ ID NO 27
<211> LENGTH: 17
<212> TYPE: PRT
<213> ORGANISM: Homo sapiens

<400> SEQUENCE: 27

Lys Ser Leu Glu Val Thr Phe Thr Pro Val Ile Glu Asp Ile Gly Lys
1               5                   10                  15

Val

<210> SEQ ID NO 28
<211> LENGTH: 13
<212> TYPE: PRT
<213> ORGANISM: Homo sapiens

<400> SEQUENCE: 28

Lys Leu His Ile Asp Asp Met Glu Phe Glu Pro Lys Gln
1               5                   10

<210> SEQ ID NO 29
<211> LENGTH: 12
<212> TYPE: PRT
<213> ORGANISM: Homo sapiens

<400> SEQUENCE: 29

Arg Ser Asp Ser Asp Ser Ser Thr Leu Ser Lys Lys
1               5                   10

<210> SEQ ID NO 30
<211> LENGTH: 13
<212> TYPE: PRT
<213> ORGANISM: Homo sapiens

<400> SEQUENCE: 30

Arg Arg Gly Asp Ser Gln Pro Tyr Gln Ala Leu Lys Tyr
1               5                   10

<210> SEQ ID NO 31
<211> LENGTH: 13
<212> TYPE: PRT
<213> ORGANISM: Homo sapiens

<400> SEQUENCE: 31

Lys Ala Ile Lys Lys Ala Ile Thr Cys Gly Glu Lys Glu
1               5                   10

<210> SEQ ID NO 32
<211> LENGTH: 12
<212> TYPE: PRT
<213> ORGANISM: Homo sapiens

<400> SEQUENCE: 32

Arg Ser Asp Ser Asp Ser Ser Thr Leu Ser Lys Lys
1               5                   10
```